United States Patent
Gruber

(12) 
(10) Patent No.: US 12,226,465 B2
(45) Date of Patent: *Feb. 18, 2025

(54) HUMANIZED MONOCLONAL ADVANCED GLYCATION END-PRODUCT ANTIBODY

(71) Applicant: Siwa Corporation, Chicago, IL (US)

(72) Inventor: Lewis S. Gruber, Chicago, IL (US)

(73) Assignee: Siwa Corporation, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/050,915

(22) Filed: Oct. 28, 2022

(65) Prior Publication Data

US 2023/0295282 A1  Sep. 21, 2023

(51) Int. Cl.
| | |
|---|---|
| A61K 39/00 | (2006.01) |
| A61K 47/68 | (2017.01) |
| A61K 47/69 | (2017.01) |
| C07K 16/18 | (2006.01) |
| C07K 16/44 | (2006.01) |
| G03G 21/16 | (2006.01) |

(52) U.S. Cl.
CPC .......... *A61K 39/00* (2013.01); *A61K 47/6843* (2017.08); *A61K 47/6923* (2017.08); *A61K 47/6929* (2017.08); *C07K 16/18* (2013.01); *C07K 16/44* (2013.01); *G03G 21/1685* (2013.01); *A61K 2039/572* (2013.01); *C07K 2317/24* (2013.01); *C07K 2317/41* (2013.01); *C07K 2317/52* (2013.01); *C07K 2317/56* (2013.01); *C07K 2317/565* (2013.01); *C07K 2317/732* (2013.01); *C07K 2317/734* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,217,344 A | 8/1980 | Vanlerberghe et al. |
| 4,900,747 A | 2/1990 | Vlassara et al. |
| 4,911,928 A | 3/1990 | Wallach |
| 4,917,951 A | 4/1990 | Wallach |
| 4,965,288 A | 10/1990 | Palfreyman |
| 5,494,791 A | 2/1996 | Cohen |
| 5,518,720 A | 5/1996 | Cohen |
| 5,601,526 A | 2/1997 | Chapelon et al. |
| 5,620,409 A | 4/1997 | Venuto |
| 5,620,479 A | 4/1997 | Diederich |
| 5,624,804 A | 4/1997 | Bucala |
| 5,664,570 A | 9/1997 | Bishop |
| 5,693,762 A | 12/1997 | Queen et al. |
| 5,702,704 A | 12/1997 | Bucala |
| 5,766,590 A | 6/1998 | Founds et al. |
| 5,811,075 A | 9/1998 | Vlassara et al. |
| 5,817,771 A | 10/1998 | Bayley et al. |
| 5,984,882 A | 11/1999 | Rosenschein et al. |
| 6,067,859 A | 5/2000 | Kas et al. |
| 6,090,382 A | 7/2000 | Salfeld et al. |
| 6,176,842 B1 | 1/2001 | Tachibana et al. |
| 6,245,318 B1 | 6/2001 | Klibanov et al. |
| 6,309,355 B1 | 10/2001 | Cain et al. |
| 6,380,165 B1 | 4/2002 | Al-Abed et al. |
| 6,387,373 B1 | 5/2002 | Wright et al. |
| 6,410,598 B1 | 6/2002 | Vitek |
| 6,670,136 B2 | 12/2003 | Schmidt et al. |
| 6,676,963 B1 | 1/2004 | Lanza et al. |
| 6,818,215 B2 | 11/2004 | Smith et al. |
| 6,821,274 B2 | 11/2004 | McHale et al. |
| 7,033,574 B1 | 4/2006 | Schneider et al. |
| 7,101,838 B2 | 9/2006 | Stern et al. |
| 7,256,273 B2 | 8/2007 | Basi et al. |
| 7,347,855 B2 | 3/2008 | Eshel et al. |
| 7,358,226 B2 | 4/2008 | Dayton et al. |
| 7,367,988 B1 | 5/2008 | Litovitz |
| 7,470,521 B2 | 12/2008 | O'Keefe |
| 7,751,057 B2 | 7/2010 | Oldenburg et al. |
| 7,815,570 B2 | 10/2010 | Eshel et al. |
| 8,318,164 B2 | 11/2012 | Warne |
| 8,323,651 B2 | 12/2012 | Gu et al. |
| 8,343,420 B2 | 1/2013 | Cioanta et al. |
| 8,398,977 B2 | 3/2013 | Bleck et al. |
| 8,721,571 B2 | 5/2014 | Gruber |
| 8,977,361 B2 | 3/2015 | Carpentier et al. |

(Continued)

FOREIGN PATENT DOCUMENTS

| | | |
|---|---|---|
| AU | 2009/248945 | 5/2014 |
| DE | 102008009461 | 8/2009 |

(Continued)

OTHER PUBLICATIONS

Zenner et al., Prostate. Feb. 2022;82(3):306-313 (Year: 2022).*

(Continued)

*Primary Examiner* — Daniel C Gamett
(74) *Attorney, Agent, or Firm* — EVAN LAW GROUP LLC

(57) ABSTRACT

A humanized monoclonal antibody that binds to an advanced glycation end-product-modified protein or peptide on a cell comprises a heavy chain and a light chain. The antibody binds a carboxymethyllysine-modified protein or peptide. A composition comprises a humanized monoclonal antibody that binds to an advanced glycation end-product-modified protein or peptide on a cell and a pharmaceutically acceptable carrier.

14 Claims, 4 Drawing Sheets
Specification includes a Sequence Listing.

(56) References Cited

U.S. PATENT DOCUMENTS

| | | |
|---|---|---|
| 8,981,112 B2 | 3/2015 | Bukhtiyarov et al. |
| 9,155,805 B2 | 10/2015 | Hamakubo |
| 9,161,810 B2 | 10/2015 | Gruber |
| 9,320,919 B2 | 4/2016 | Gruber |
| 9,493,566 B2 | 11/2016 | Ryan |
| 9,493,567 B2 | 11/2016 | Lieberburg |
| 9,649,376 B2 | 5/2017 | Gruber |
| 9,884,065 B2 | 2/2018 | Campisi et al. |
| 9,993,535 B2 | 6/2018 | Gruber |
| 10,172,684 B2 | 1/2019 | Conlon et al. |
| 10,226,531 B2 | 3/2019 | Gruber |
| 10,358,502 B2 | 7/2019 | Gruber |
| 10,584,180 B2 | 3/2020 | Gruber |
| 10,858,449 B1 | 12/2020 | Gruber |
| 10,889,634 B2 | 1/2021 | Gruber |
| 10,919,957 B2 | 2/2021 | Gruber |
| 10,925,937 B1 | 2/2021 | Gruber |
| 10,960,234 B2 | 3/2021 | Gruber |
| 10,961,321 B1 | 3/2021 | Gruber |
| 10,995,151 B1 | 5/2021 | Gruber |
| 11,213,585 B2 | 1/2022 | Gruber |
| 11,261,241 B2 | 3/2022 | Gruber |
| 11,518,801 B1 | 12/2022 | Gruber |
| 11,542,324 B2 | 1/2023 | Gruber |
| 11,833,202 B2 | 12/2023 | Gruber |
| 11,872,269 B2 | 1/2024 | Gruber |
| 11,873,345 B2 | 1/2024 | Gruber |
| 11,958,900 B2 | 4/2024 | Gruber |
| 12,134,660 B2 | 11/2024 | Gruber |
| 2002/0122799 A1 | 9/2002 | Stern et al. |
| 2002/0193784 A1 | 12/2002 | McHale et al. |
| 2003/0073138 A1 | 4/2003 | Kientsch-Engel et al. |
| 2003/0115614 A1 | 6/2003 | Kanda |
| 2003/0170173 A1 | 9/2003 | Klaveness et al. |
| 2003/0229283 A1 | 12/2003 | Craig et al. |
| 2004/0039416 A1 | 2/2004 | Myhr |
| 2004/0141922 A1 | 7/2004 | Klaveness et al. |
| 2004/0142391 A1 | 7/2004 | Schmidt |
| 2004/0208826 A1 | 10/2004 | Schneider et al. |
| 2004/0210042 A1 | 10/2004 | Tsuchida |
| 2004/0229830 A1 | 11/2004 | Tachibana et al. |
| 2005/0084538 A1 | 4/2005 | Dayton et al. |
| 2005/0283098 A1 | 12/2005 | Conston et al. |
| 2006/0078501 A1 | 4/2006 | Goertz et al. |
| 2006/0122543 A1 | 6/2006 | Mayer et al. |
| 2006/0188883 A1 | 8/2006 | Murray et al. |
| 2006/0222646 A1 | 10/2006 | Treacy |
| 2006/0241524 A1 | 10/2006 | Lee |
| 2007/0059247 A1 | 3/2007 | Lindner et al. |
| 2007/0065415 A1 | 3/2007 | Kleinsek et al. |
| 2007/0065443 A1 | 3/2007 | Tobia |
| 2007/0071675 A1 | 3/2007 | Wu et al. |
| 2007/0078290 A1 | 4/2007 | Esenaliev |
| 2007/0083120 A1 | 4/2007 | Cain et al. |
| 2007/0128117 A1 | 6/2007 | Bettinger et al. |
| 2007/0129633 A1 | 6/2007 | Lee et al. |
| 2007/0225242 A1 | 9/2007 | Erler |
| 2008/0019986 A1 | 1/2008 | Stern et al. |
| 2008/0051680 A1 | 2/2008 | Luebcke |
| 2008/0063603 A1 | 3/2008 | Schneider et al. |
| 2008/0139942 A1 | 6/2008 | Gaud et al. |
| 2008/0160506 A1 | 7/2008 | Liu et al. |
| 2009/0022659 A1 | 1/2009 | Olson et al. |
| 2009/0076390 A1 | 3/2009 | Lee et al. |
| 2009/0306552 A1 | 12/2009 | Furuzono et al. |
| 2010/0028359 A1 | 2/2010 | Gu et al. |
| 2010/0226932 A1 | 9/2010 | Smith et al. |
| 2010/0249038 A1 | 9/2010 | Logsdon |
| 2011/0105961 A1 | 5/2011 | Gruber |
| 2011/0319499 A1 | 12/2011 | Semba et al. |
| 2012/0130287 A1 | 5/2012 | Gruber |
| 2012/0135918 A1 | 5/2012 | Bowers |
| 2012/0156134 A1 | 6/2012 | Squires |
| 2012/0183534 A1 | 7/2012 | Gruber |
| 2013/0058921 A1 | 3/2013 | Van Rhee |
| 2013/0131006 A1 | 5/2013 | Lee et al. |
| 2013/0243785 A1 | 9/2013 | Gruber |
| 2013/0288980 A1 | 10/2013 | De Keizer et al. |
| 2014/0234339 A1 | 8/2014 | Ohlsen |
| 2014/0234343 A1 | 8/2014 | Lee et al. |
| 2014/0303526 A1 | 10/2014 | Gruber |
| 2015/0376279 A1 | 12/2015 | Hansen |
| 2016/0017033 A1 | 1/2016 | Squires |
| 2016/0038576 A1 | 2/2016 | Vasserot et al. |
| 2016/0083437 A1 | 3/2016 | Cho et al. |
| 2016/0091410 A1 | 3/2016 | Krug |
| 2016/0101299 A1 | 4/2016 | Gruber |
| 2016/0152697 A1 | 6/2016 | Gruber |
| 2016/0175413 A1 | 6/2016 | Gruber |
| 2016/0193358 A1 | 7/2016 | Algate |
| 2016/0215043 A1 | 7/2016 | Gruber |
| 2016/0279261 A1 | 9/2016 | Lee |
| 2016/0311907 A1 | 10/2016 | Brogdon et al. |
| 2016/0339019 A1 | 11/2016 | Laberge et al. |
| 2016/0340418 A1 | 11/2016 | Baron |
| 2017/0216286 A1 | 8/2017 | Kirkland |
| 2017/0216435 A1 | 8/2017 | Gruber |
| 2017/0240632 A1 | 8/2017 | Thomas |
| 2017/0247472 A1 | 8/2017 | Gruber |
| 2017/0259086 A1 | 9/2017 | Carpentier et al. |
| 2018/0036558 A1 | 2/2018 | Carpentier et al. |
| 2018/0044411 A1 | 2/2018 | Gruber |
| 2018/0111982 A2 | 4/2018 | Gruber |
| 2018/0298087 A1 | 10/2018 | Gruber |
| 2018/0312577 A1 | 11/2018 | Gruber |
| 2018/0326026 A1 | 11/2018 | Gruber |
| 2019/0031781 A1 | 1/2019 | Gruber |
| 2019/0119371 A1 | 4/2019 | Gruber |
| 2019/0328873 A1 | 10/2019 | Gruber |
| 2019/0328876 A1 | 10/2019 | Gruber |
| 2020/0054682 A1 | 2/2020 | Gojo et al. |
| 2020/0055957 A1 | 2/2020 | Gruber |
| 2020/0150131 A1 | 5/2020 | Gruber |
| 2020/0231706 A1 | 7/2020 | Gruber |
| 2021/0087297 A1 | 3/2021 | Gruber |
| 2021/0208533 A1 | 7/2021 | Gruber |
| 2021/0236860 A1 | 8/2021 | Gruber |
| 2021/0253737 A1 | 8/2021 | Gruber |
| 2021/0253739 A1 | 8/2021 | Gruber |
| 2022/0160869 A1 | 5/2022 | Gruber |
| 2022/0175916 A1 | 6/2022 | Gruber |
| 2023/0181730 A1 | 6/2023 | Gruber |
| 2023/0295282 A1 | 9/2023 | Gruber |
| 2024/0000930 A1 | 1/2024 | Gruber |

FOREIGN PATENT DOCUMENTS

| | | |
|---|---|---|
| EP | 0 259 893 | 3/1988 |
| EP | 1 219 639 | 7/2002 |
| EP | 1 415 997 | 5/2004 |
| EP | 1 867 659 | 12/2007 |
| EP | 2 294 178 | 7/2014 |
| EP | 2998322 | 3/2016 |
| JP | 09178740 | 7/1997 |
| JP | 11246599 | 9/1999 |
| JP | 2003/160599 | 6/2003 |
| JP | 2006-249015 | 9/2006 |
| JP | 2007-163407 | 6/2007 |
| JP | 2007277263 | 10/2007 |
| RU | 2 270 029 | 1/2006 |
| RU | 2617313 | 4/2017 |
| WO | 1993/134421 | 7/1993 |
| WO | 1995/20979 | 8/1995 |
| WO | 1996/13610 | 5/1996 |
| WO | 1996/20958 | 7/1996 |
| WO | 1997/07803 | 3/1997 |
| WO | 1997/49429 | 12/1997 |
| WO | 1999/07893 | 2/1999 |
| WO | 1999/14587 | 3/1999 |
| WO | 1999/64463 | 12/1999 |
| WO | 2000/20458 | 4/2000 |
| WO | 2001/00245 | 1/2001 |
| WO | 2001/077342 | 10/2001 |
| WO | 2004/011460 | 2/2004 |

(56) References Cited

FOREIGN PATENT DOCUMENTS

| | | |
|---|---|---|
| WO | 2004/016229 | 2/2004 |
| WO | 2004/076677 | 9/2004 |
| WO | 2006/012415 | 2/2006 |
| WO | 2006/017647 | 2/2006 |
| WO | 2006/040597 | 4/2006 |
| WO | 2009/136382 | 11/2009 |
| WO | 2009/143411 | 11/2009 |
| WO | 2010/005531 | 1/2010 |
| WO | 2011/032633 | 3/2011 |
| WO | 2012/047629 | 4/2012 |
| WO | 2012/071269 | 5/2012 |
| WO | 2012/135616 | 10/2012 |
| WO | 2013/009785 | 1/2013 |
| WO | 2013/043161 | 3/2013 |
| WO | 2013/070468 | 5/2013 |
| WO | 2013/090645 | 6/2013 |
| WO | 2014/090991 | 6/2014 |
| WO | 2014/136114 | 9/2014 |
| WO | 2014/164693 | 10/2014 |
| WO | 2015/112835 | 7/2015 |
| WO | 2015/116735 | 8/2015 |
| WO | 2015/116740 | 8/2015 |
| WO | 2016/044252 | 3/2016 |
| WO | 2017/065837 | 4/2017 |
| WO | 2017/143073 | 8/2017 |
| WO | 2017/181116 | 10/2017 |
| WO | 2017/222535 | 12/2017 |
| WO | 2018/191718 | 10/2018 |
| WO | 2018/204679 | 11/2018 |
| WO | 2020/023532 | 1/2020 |
| WO | 2020/041625 | 2/2020 |
| WO | 2021/222758 | 11/2021 |
| WO | 2021/247397 | 12/2021 |
| WO | 2022/093195 | 5/2022 |
| WO | 2022/125776 | 6/2022 |
| WO | 2023/023654 | 2/2023 |
| WO | 2023/177390 | 9/2023 |
| WO | 2024/102157 | 5/2024 |

OTHER PUBLICATIONS

U.S. Appl. No. 16/779,369, filed Jan. 31, 2020.
U.S. Appl. No. 17/544,636, filed Dec. 7, 2021.
U.S. Appl. No. 17/262,684, filed Jan. 22, 2021, Jul. 23, 2019.
U.S. Appl. No. 17/268,413, filed Aug. 22, 2019.
U.S. Appl. No. 18/611,415, filed Mar. 20, 2024.
U.S. Appl. No. 18/684,824, filed Feb. 19, 2024, Aug. 19, 2022.
U.S. Appl. No. 18/755,509, filed Jun. 26, 2024.
U.S. Appl. No. 18/146,821, filed Dec. 27, 2022.
U.S. Appl. No. 18/265,205, filed Jun. 2, 2023, Dec. 9, 2021.
U.S. Appl. No. 17/922,264, filed Oct. 28, 2022, Apr. 30, 2021.
Sabbatinelli, J. et al., "Where metabolism meets senescence: Focus on endothelial cells", Frontiers in Physiology, vol. 10, article 1523, pp. 1-17, (2019).
International Search Report and written opinion dated Dec. 2, 2022 for PCT application No. PCT/US2022/020257.
Jensen, A et al., "SIWA318H, an advanced glycation end product (AGE) targeting antibody, is efficacious in a humanized mouse xenograft model for pancreatic cancer", Cancer Research, vol. 81, 22_Supplement, (2021). Abstract Only.
International Search Report and written opinion dated Nov. 22, 2022 for PCT application No. PCT/US2022/075226.
Liu, R-M. et al., "Cell senescence and fibrotic lung diseases", Experimental Gerontology, vol. 132, pp. 1-7, (2020).
Hernandez-Gonzalez, F. et al., "Cellular senescence in lung fibrosis", International Journal of Molecular Sciences, vol. 22, pp. 1-15, (2021).
Paneni, F. et al., "Advanced glycation endproducts and plaque instability: a link beyond diabetes", European Heart Journal, vol. 35, issue 17, pp. 1095-1097, (2014).
Ahmed, K.A., et al., "N$^\varepsilon$-(Carboxymethyl)lysine and coronary atherosclerosis-associated low density lipoprotein abnormalities in type 2 diabetes: current status", Journal of Clinical Biochemistry and Nutrition, vol. 44, No. 1, pp. 14-27, (2009).
Bar, K.J. et al., "Pentosidine and NE-(Carboxymethyl)lysine in Alzheimer's disease and vascular dementia", Neurobiology of Aging, vol. 24, issue 2, pp. 333-358, (2003).
Begieneman, M.P.V. et al., "Atrial fibrillation coincides with the advanced glycation end product N$\varepsilon$-(Carboxymethyl)lysine in the atrium", The American Journal of Pathology, vol. 185, No. 8, pp. 2096-2104, (2015).
Girones, X. et al., "N epsilon—carboxymethyllysine in brain aging, diabetes mellitus, and Alzheimer's disease", Free Radical Biology & Medicine, vol. 36, No. 10, pp. 1241-1247, (2004). Abstract Only.
Keith, S.W. et al., "Angiotensin blockade therapy and survival in pancreatic cancer: a population study", BMC Cancer, vol. 22, article 150, pp. 1-9, (2022).
Khan, M.A. et al., "Underlying histopathology determines response to oxidative stress in cultured human primary proximal tubular epithelial cells", International Journal of Molecular Sciences, vol. 21, issue 2, pp. 1-15, (2020).
Loperena, R. et al., "Oxidative stress and hypertensive diseases", The Medical Clinics of North America, vol. 101, No. 1, pp. 169-193, (2017).
Mossad, O. et al., "Gut microbiota drives age-related oxidative stress and mitochondrial damage in microglia via the metabolite $N^6$-carboxymethyllysine", Nature Neuroscience, vol. 25, pp. 295-305, (2022). Abstract Only.
Park, J-S. et al., "Blocking microglial activation of reactive astrocytes is neuroprotective in models of Alzheimer's disease", Acta Neuropathologica Communications, vol. 9, No. 1, pp. 1-15, (2021).
Shi, R-Z et al., "Angiotensin II induces vascular endothelial growth factor synthesis in mesenchymal stem cells", Experimental Cell Research, vol. 315, No. 1, pp. 10-15, (2009). Abstract Only.
Takeda, A. et al., "Neuronal and glial advanced glycation end product [Nepsilon- (carboxymethyl)lysine]] in Alzheimer's disease brains", Acta Neuropathologica, vol. 101, No. 1, pp. 27-35, (2001). Abstract Only.
Xu, S-N. et al., "NE-Carboxymethyl-lysine deteriorates vascular calcification in diabetic atherosclerosis induced by vascular smooth muscle cell-derived foam cells", Frontiers in Pharmacology, vol. 11, article 626, pp. 1-12, (2020).
Eske, J., "What is oxidative stress? Effects on the body and how to reduce", Medical News Today, 4 pages, (2020).
Fuller, S. et al., "Activated astrocytes: a therapeutic target in Alzheimer's disease?", Expert Review of Neurotherapeutics, vol. 9, No. 11, pp. 1585-1594, (2009).
International Search Report dated Feb. 21, 2023 for PCT application No. PCT/US2021/062606.
Al-Abed, Y. et al., "N$\varepsilon$-carboxymethyllysine formation by direct addition of glyoxal to lysine during the maillard reaction", Bioorganic & Medicinal Chemistry Letters, vol. 5, issue 18, pp. 2161-2162, (1995). Abstract Only.
Severin, F.F. et al., "Advanced glycation of cellular proteins as a possible basic component of the "master biological clock, Biochemistry (Moscow) 9, No. 78, pp. 1043-1047, (2013).
Khoja, L. et al., "A pilot study to explore circulating tumour cells in pancreatic cancer as a novel biomarker", British Journal of Cancer, vol. 106, pp. 508-516, (2012).
Cosgrove, C. et al., "The impact of 6-month training preparation for an ironman triathlon on the proportions of naïve, memory and senescent T cells in resting blood", European Journal of Applied Physiology, vol. 112, pp. 2989-2998, (2012).
Spielmann, G. et al., "Aerobic fitness is associated with lower proportions of senescent blood T-cells in man", Brain, Behavior, and Immunity, vol. 25, issue 8, pp. 1521-1529, (2011).
Schmid, D. et al., "Collagen glycation and skin aging", Cosmetics and Toiletries Manufacture Worldwide, pp. 1-6, (2017).
Pauwels, E.K.J. et al., "Radiolabelled monoclonal antibodies: A new diagnostic tool in nuclear medicine" Radiotherapy and Oncology, vol. 1, issue 4, pp. 333-338, (1984). Abstract Only.
Wong, R. et al., "Use of RT-PCR and DNA microarrays to characterize RNA recovered by non- invasive tape harvesting of normal and inflamed skin", The Journal of Investigative Dermatology, vol. 123, pp. 159-167, (2004).

(56) References Cited

OTHER PUBLICATIONS

Pearce, M.S. et al., "Childhood growth, IQ and education as predictors of white blood cell telomere length at age 49-51 years: The Newcastle thousand families study", PLoS one, vol. 7, issue 7, e40116, pp. 1-7, (2012).
"CD8+CD57+ T cell isolation kit, human", Miltenyi Biotec, pp. 1-4, (2017).
"Extraction of genomic DNA from buccal epithelial cells", available online at authors.fhcrc.org/591/1/Buccal%20Cell%20DNA%20Isol%20v2.pdf, printed on Apr. 19, 2017.
Lingner, M. et al., "Adherence of pseudomonas aeruginosa to cystic fibrosis buccal epithelial cells", ERJ Open Research, vol. 3, pp. 1-3, (2017).
Sebekova, K. et al., "Total plasma N&-(carboxymethyl)lysine and sRAGE levels are inversely associated with a number of metabolic syndrome risk factors in non-diabetic young-to-middle-aged medication-free subjects", Clinical Chemistry and Laboratory Medicine, vol. 52, No. 1, pp. 139-149, (2014). Abstract Only.
Xu, H. et al., "Biodistribution and elimination study of fluorine-18 labeled Ne-carboxymethyl- lysine following intragastric and intravenous administration", PLoS One, vol. 8, issue 3, e57897, pp. 1-11, (2013).
Cahu, J. et al., "A sensitive method to quantify senescent cancer cells", Journal of Visualized Experiments, vol. 78, e50494, pp. 1-6, (2013).
Rutkauskaite, V. et al., "Reduction in proportion of senescent CD8+ T lymphocytes during chemotherapy of children with acute lymphoblastic leukemia", Anticancer Research, vol. 36, pp. 6195-6200, (2016).
Castellino, A.M., "Questions on PD-L1 diagnostics for immunotherapy in NSCLC", Medscape Medical News, www.medscape.com/viewarticle/862275, (2016).
Shi, D-Y. et al., "The role of cellular oxidative stress in regulating glycolysis energy metabolism in hepatoma cells", Molecular Cancer, vol. 8, No. 32, pp. 1-15, (2009).
"Screening and monitoring of chronic kidney disease (CKD) in diabetes, frequently asked questions", Indian Health Service, Division of Diabetes Treatment and Prevention, found at www.ihs.gov/MedicalPrograms/Diabetes/HomeDocs/Tools/ClinicalGuidelines/CKD_FAQ_Jul20 14.pdf, pp. 1-4, printed on Jun. 2, 2023.
Palinski, W. et al., "Immunological evidence for the presence of advanced glycosylation end products in atherosclerotic lesions of euglycemic rabbits", Arteriosclerosis, Thrombosis, and Vascular Biology, vol. 15, issue 5, pp. 571-582, (1995).
Meerwaldt, R. et al., "Simple non-invasive assessment of advanced glycation endproduct accumulation", Diabetologia, vol. 47, pp. 1324-1330, (2004).
Brown, F.F. et al., "Training status and sex influence on senescent T-lymphocyte redistribution in response to acute maximal exercise", Brain, Behavior, and Immunity, vol. 39, pp. 152-159, (2014).
"Telomere testing white paper", Titanovo, available online at titanovo.com/telomere- length_testing/, accessed on Apr. 20, 2017.
Khan, M.Y. et al., "Immunochemical studies on native and glycated LDL—an approach to uncover the structural perturbations", International Journal of Biological Macromolecules, vol. 115, pp. 287-299, (2018).
Ikeda, T. et al., "Possible roles of anti-type II collagen antibody and innate immunity in the development and progression of diabetic retinopathy", Graefe's Archive for Clinical and Experimental Ophthalmology, vol. 260, pp. 387-403, (2022).
Bassiouny, A.R. et al., "Glucosylated collagen is antigenic", Diabetes, vol. 32, pp. 1182-1184, (1983).
Zenner, M.L. et al., "Advanced glycation end-products (AGEs) are lower in prostate tumor tissue and inversely related to proportion of west African ancestry", Prostate, vol. 82, No. 3, pp. 306-313, (2022).
Berkman, P. et al., "Antibody dependent cell mediated cytotoxicity and phagocytosis of senescent erythrocytes by autologous peripheral blood mononuclear cells", Autoimmunity, vol. 35, No. 6, pp. 415-419, (2002).
Childs, B.G. et al., "Cellular senescence in aging and age-related disease: from mechanisms to therapy", Nature Medicine, vol. 21, No. 12, pp. 1424-1435, (2015).
Ide, H. et al., "DNA damage response in prostate cancer cells after high-intensity focused ultrasound (HIFU) treatment", Anticancer Research, vol. 28, pp. 639-644, (2008).
Saudek, D.M. et al., "Advanced glycation endproducts and osteoarthritis", Current Rheumatology Reports, vol. 5, pp., 33-40, (2003).
Jia, L. et al., "Efficacy of focused low-intensity pulsed ultrasound therapy for the management of knee osteoarthritis: a randomized double blind, placebo-controlled trial", Scientific Reports, vol. 6, No. 35453, pp. 1-9, (2016).
Wei, K-C. et al., "Focused ultrasound-induced blood-brain barrier opening to enhance temozolomide delivery for glioblastoma treatment: A preclinical study", PLOS one, vol. 8, issue 3, No. e58995, pp. 1-10, (2013).
Ramachandran, T.V., "Background radiation, people and the environment", Iranian Journal of Radiation Research, vol. 9, No. 2, pp. 63-76, (2011).
Serio, R.N., "Unraveling the mysteries of aging through a Hutchinson-Gilford Progeria syndrome model", Rejuvenation Research, vol. 14, No. 2, pp. 133-141, (2011).
Hymes, S. R. et al., "Radiation dermatitis: Clinical presentation pathophysiology, and treatment 2006", Journal of the American Academy of Dermatology, vol. 54, No. 1, pp. 28-46, (2006).
International Search Report dated Jul. 21, 2009 for PCT application No. PCT/US2009/44951.
Lindsey, J.B. et al., "Receptor for advanced glycation end-products (RAGE) and soluble RAGE (sRAGE): Cardiovascular implications", Diabetes Vascular Disease Research, vol. 6, No. 1, pp. 7-14, (2009).
Ando, K. et al., "Membrane proteins of human erythrocytes are modified by advanced glycation end products during aging in the circulation", Biochemical and Biophysical Research Communications, vol. 258, pp. 123-127, (1999).
Jandeleit-Dahm, K. et al., "The AGE/RAGE axis in diabetes-accelerated atherosclerosis", Clinical and Experimental Pharmacology and Physiology, vol. 35, pp. 329-334, (2008).
Sakata, N. et al., "Immunohistochemical localization of different epitopes of advanced glycation end products in human atherosclerotic lesions", Atherosclerosis, vol. 141, pp. 61-75, (1998).
Karachalias, N. et al., "Accumulation of fructosyl-lysine and advanced glycation end products in the kidney, retina and peripheral nerve of streptozotocin-induced diabetic rats", Biochemical Society Transactions, vol. 31, pp. 1423-1425, (2003).
Aroian, R. et al., "Pore-forming toxins and cellular non-immune defenses (CNIDs)", Current Opinion in Microbiology, vol. 10, pp. 57-61, (2007).
Dobson, J., "A twist on tumour targeting", Nature Materials, vol. 9, pp. 95-96, (2010).
Gutensohn, K. et al., "Extracorporeal plateletpheresis induces the interaction of activated platelets with white blood cells", Vox Sanguinis, vol. 78, No. 2, pp. 101-105, (2000).
Horiuchi, S. et al., "Immunochemical approach to characterize advanced glycation end products of the maillard reaction", The Journal of Biological Chemistry, vol. 266, No. 12, pp. 7329-7332, (1991).
Soetanto, K. et al., "Fundamental examination of cattle red blood cells damage with ultrasound exposure microscopic system (UEMS)", Japanese Journal of Applied Physics, vol. 37, part 1, No. 5B, pp. 3070-3073, (1998).
Harja, E. et al., "Vascular and inflammatory stresses mediate atherosclerosis via RAGE and its ligands in apoE-/- mice", The Journal of Clinical Investigation, vol. 118, No. 1, pp. 183-194, (2008).
Carstensen, E.L. et al., "Lysis of erythrocytes by exposure to cw ultrasound", Ultrasound in Medicine and Biology, vol. 19, No. 2, pp. 147-165, (1993).
Miller, M.W. et al., "Comparative sensitivity of human erythrocytes and lymphocytes to sonolysis by 1-MHz ultrasound", Ultrasound in Medicine and Biology, vol. 23, No. 4, pp. 635-638, (1997).

(56) References Cited

OTHER PUBLICATIONS

Iwata, H. et al., "Effect of carbonyl compounds on red blood cells deformability", Biochemical and Biophysical Research Communications vol. 321, pp. 700-706, (2004).
Schmitt, A. et al., "The binding of advanced glycation end products to cell surfaces can be measured using bead-reconstituted cellular membrane proteins", Biochimica et Biophysica Acta, vol. 1768, pp. 1389-1399, (2007).
Self-Medlin, Y. et al., "Glucose promotes membrane cholesterol crystalline domain formation by lipid peroxidation", Biochimica et Biophysica Acta, vol. 1788, pp. 1398-1403, (2009).
Singh, N. et al., "The PPAR-γ activator, rosiglitazone, inhibits actin polymerisation in monocytes: involvement of Akt and intracellular calcium", Biochemical and Biophysical Research Communications, vol. 333, pp. 455-462, (2005).
Li, Y-M. et al., "Effects of high glucose on mesenchymal stem cell proliferation and differentiation", Biochemical and Biophysical Research Communications, vol. 363, pp. 209-215, (2007).
Takata, K. et al., "Endocytic uptake of nonenzymatically glycosylated proteins is mediated by a scavenger receptor for aldehyde-modified proteins", The Journal of Biological Chemistry, vol. 263, No. 29, p. 14819-14825, (1988).
Mi, Y. et al., "Apoptosis in leukemia cells is accompanied by alterations in the levels and localization of nucleolin", Journal of Biological Chemistry, vol. 278, pp. 8572-8579, (2003).
Christian, S. et al., "Nucleolin expressed at the cell surface is a marker of endothelial cells in angiogenic blood vessels", Journal of Cell Biology, vol. 163, No. 4, pp. 871-878, (2003).
Loo, T.W. et al., "Identification of residues in the drug translocation pathway of the human multidrug resistance P-glycoprotein by arginine mutagenesis", Journal of Biological Chemistry, vol. 284, No. 36, pp. 24074-24087, (2009).
Brundin, P. et al., "Prion-like transmission of protein aggregates in neurodegenerative diseases", Nature Reviews Molecular Cell Biology, vol. 11, No. 4, pp. 301-307, (2010).
Perez, C. et al., "Translational control of the abundance of cytoplasmic poly(A) binding protein in human cytomegalovirus-infected cells", Journal of Virology, vol. 85, No. 1, pp. 156-164, (2011).
Persson, J. et al., "Interleukin-Ibeta and tumour necrosis factor-alpha impede neutral lipid turnover in macrophage-derived foam cells", BMC Immunology, vol. 9, No. 70, pp. 1-11, (2008).
Vergne, I. et al., "Cell biology of mycobacterium tuberculosis phagosome", Annu. Rev. Cell Dev. Biology, vol. 20, pp. 367-394, (2004).
Moskowitz, S.M. et al., "The role of pseudomonas lipopolysaccharide in cystic fibrosis airway Infection", Subcell Biochemistry, vol. 53, pp. 241-253, (2010).
Hall-Stoodley, L. et al., "Direct detection of bacterial biofilms on the middle-ear mucosa of children with chronic otitis media", JAMA, vol. 296, No. 2, pp. 202-211, (2006).
Franke-Fayard, B. et al., "Sequestration and tissue accumulation of human malaria parasites: Can we learn anything from rodent models of malaria?", PLOS Pathogens, vol. 6, issue 9, pp. 1-10, e1001032, (2010).
Zhang, S. et al., "Delineation of diverse macrophage activation programs in response to intracellular parasites and cytokines", PLoS Neglected Tropical Diseases, vol. 4, No. 3, e648 (2010).
Ma, Y. et al., "NS3 helicase domains involved in infectious intracellular hepatitis C virus particle assembly", Journal of Virology, vol. 82, No. 15, pp. 7624-7639, (2008).
Korant, B.D. et al., "Inhibition by zinc of rhinovirus protein cleavage: interaction of zinc with capsid polypeptides", Journal of Virology, vol. 18, No. 1, pp. 298-306, (1976).
Ameli, S. et al., "Effect of immunization with homologous LDL and oxidized LDL on early atherosclerosis in hypercholesterolemic rabbits", Arteriosclerosis, Thrombosis, and Vascular Biology, vol. 16, pp. 1074-1079, (1996).
Nilsson, J. et al., "Inflammation and immunity in diabetic vascular complications", Current Opinion in Lipidology, vol. 19, issue 5, pp. 519-524, (2008).
Schiopu, A. et al., "Recombinant antibodies to an oxidized low-density lipoprotein epitope induce rapid regression of atherosclerosis in apobec-1-+/low-density lipoprotein receptor' mice", Journal of the American College of Cardiology, vol. 50, No. 24, pp. 2313-2318, (2007).
Schiopu, A. et al., "Recombinant human antibodies against aldehyde-modified apolipoprotein B-100 peptide sequences inhibit atherosclerosis", Circulation, vol. 110, pp. 2047-2052, (2004).
Bassirat, M. et al., "Short- and long-term modulation of microvascular responses in streptozotocin-induced diabetic rats by glycosylated products", Journal of Diabetes and its Complications, vol. 24, pp. 64-72, (2010).
Ge, J. et al., "Advanced glycosylation end products might promote atherosclerosis through inducing the immune maturation of dendritic cells", Arteriosclerosis, Thrombosis, and Vascular Biology, vol. 25, pp. 2157-2163, (2005).
Gugliucci, A. et al., "Circulating advanced glycation peptides in streptozotocin-induced diabetic rats: evidence for preferential modification of IgG light chains", Life Sciences, vol. 62, No. 23, pp. 2141-2150, (1998).
Pullerits, R. et al., "Synovial fluid expression of autoantibodies specific for RAGE relates to less erosive course of rheumatoid arthritis", Rheumatology, vol. 46, pp. 1367-1371, (2007).
Bro, S. et al., "A neutralizing antibody against receptor for advanced glycation end products (RAGE) reduces atherosclerosis in uremic mice", Atherosclerosis, vol. 201, pp. 274-280, (2008).
Turk, Z. et al., "Detection of autoantibodies against advanced glycation endproducts and AGE-immune complexes in serum of patients with diabetes mellitus", Clinica Chimica Acta, vol. 303, pp. 105-115, (2001).
Li, M. et al., "Glycan changes: cancer metastasis and anti-cancer vaccines", Journal of Biosciences, vol. 35, No. 4, pp. 665-673, (2010).
Kyte, J.A. et al., "Third international conference on cancer vaccines/adjuvants/delivery for the next decade (CVADD 2009)", Expert Reviews Vaccines, vol. 9, No. 2, pp. 119-123, (2010).
Akbulut, H. et al., "Chemotherapy targeted to cancer tissue potentiates antigen-specific immune response induced by vaccine for in vivo antigen loading and activation of dendritic cells", Molecular Therapy, vol. 16, No. 10, pp. 1753-1760, (2008).
Li, Y.M. et al., "Glycation products in aged thioglycollate medium enhance the elicitation of peritoneal macrophages", Jounal of Immunological Methods, vol. 201, issue 2, pp. 183-188, (1997).
Poggioli, S. et al., "Age-related increase of protein glycation in peripheral blood lymphocytes is restricted to preferential target proteins", Experimental Gerontology, vol. 37, issue 10-11, pp. 1207-1215, (2002).
Poggioli, S. et al., "Evidence of preferential protein targets for age-related modifications in peripheral blood lymphocytes", Annals of the New York Academy of Sciences, vol. 1019, issue 1, pp. 211-214, (2004).
Dominaitiene, R. et al., "Effects of differently oxidized LDL on the expression of pro-inflammatory molecules in human monocytes in vitro", In Vitro and Molecular Toxicology, vol. 14, No. 2, pp. 83-97, (2001).
Jiang, Z-H. et al., "Synthetic vaccines: the role of adjuvants in immune targeting", Current Medicinal Chemistry, vol. 10, No. 15, pp. 1423-1439, (2003).
Buskas, T. et al., "Immunotherapy for cancer: Synthetic carbohydrate-based vaccines", Chemical Communications, Issue 36, pp. 5335-5349, (2009).
Cohen, M.P. et al., "Amelioration of diabetic nephropathy by treatment with monoclonal antibodies against glycated albumin", Kidney International, vol. 45, pp. 1673-1679, (1994).
Davis, P. J. et al., "How can thermal processing modify the antigenicity of proteins?", Allergy, vol. 56, supplemental 67, pp. 56-60, (2001).
Koga, M. et al. "Clinical impact of glycated albumin as another glycemic control marker", Endocrine Journal, vol. 57, No. 9, pp. 751-762, (2010).

(56) References Cited

OTHER PUBLICATIONS

Shcheglova, T. et al., "Reactive immunization suppresses advanced glycation and mitigates diabetic nephropathy", Journal of the American Society of Nephrology, vol. 20, No. 5, pp. 1012-1019, (2009).
Virella, G. et al., "Autoimmune response to advanced glycosylation end-products of human LDL", Journal of Lipid Research, vol. 44, pp. 487-493, (2003).
Ihssen, J. et al., "Production of glycoprotein vaccines in *Escherichia coli*", Microbial Cell Factories, vol. 9, No. 61, pp. 1-13, (2010).
Habets, K.L.L. et al., "Vaccination using oxidized low-density lipoprotein-pulsed dendritic cells reduces atherosclerosis in LDL receptor-deficient mice", Cardiovascular Research, vol. 85, pp. 622-630, (2010).
Mironova, R. et al., "Glycation and post-translational processing of human interferon-γ expressed in *Escherichia coli*", The Journal of Biological Chemistry, vol. 278, No. 51, pp. 51068-51074, (2003).
Vogel, F.R. et al., "A compendium of vaccine adjuvants and excipients", Pharmaceutical Biotechnology, vol. 6, pp. 141-228, (1995).
Monograph series, World Health Organization, "Methods of Vaccine Production", part 4, chapters 18-29, pp. 189-267, (1973).
Cohen, M.P. et al., "Prevention of diabetic nephropathy in db/db mice with glycated albumin antagonists: A novel treatment strategy", The Journal of Clinical Investigation, vol. 95, pp. 2338-2345, (1995).
Naka, Y. et al., "RAGE Axis, Animal models and novel insights into the vascular complications of diabetes", Arteriosclerosis, Thrombosis, and Vascular Biology, vol. 24, pp. 1342-1349, (2004).
European Search Report dated Nov. 8, 2011 for PCT application No. PCT/US2009/044951.
Bierhaus, A. et al., "AGEs and their interaction with AGE-receptors in vascular disease and diabetes mellitus. I. the AGE concept", Cardiovascular Research, vol. 37, No. 3, pp. 586-600, (1998).
Murphy, J.F. "Trends in cancer immunotherapy", Clinical Medicine Insights: Oncology, vol. 4, pp. 67-80, (2010).
Beier, K.C., "Master switches of T-cell activation and differentiation", European Respiratory Journal, vol. 29, pp. 804-812, (2007).
Schmidlin, H., "New insights in the regulation of human B cell differentiation", Trends in Immunology, vol. 30, No. 6, pp. 277-285, (2009).
Coler, R.N. et al., "Development and characterization of synthetic glucopyranosyl lipid adjuvant system as a vaccine adjuvant", PLoS One, vol. 6, No. 1, e16333, pp. 1-12, (2011).
Cheadle, E.J., "Bugs as drugs for cancer", Immunology, vol. 107, pp. 10-19, (2002).
The Pink Book, Epidemiology and Prevention of vaccine preventable diseases, 11th Ed., pp. B7-B13, (2009), Found at www.cdc.gov/vaccines/pubs/pinkbook/downloads/appendices/b/excipient-table-1.pdf.
The Pink Book, Epidemiology and Prevention of vaccine preventable diseases, 11th Ed., 4 pages, (2009), Found at www.cdc.gov/vaccines/pubs/pinkbook/downloads/appendices/b/excipient-table-2.pdf.
Book Reviews, International Microbiology, vol. 7, pp. 291-295, (2004).
"Glycation: How eating sugar causes wrinkles", www.brighthub.com/health/diet- nutrition/articles/18410.aspx, 1 page, published Oct. 8, 2009.
Ellis, G., "The myth of the glycemic index and its child: good carbs-bad carbs", Targeted Body Systems, www.targetedbodysystems.com/tag/low-carb-diet-plans/, pp. 1-5, published Feb. 16, 2009.
"Diabetic glycation and inflammation—what diabetes does to your coronary arteries", www.rebelheartsurgeon-antioxidants.net/diabetic-glycation.html, pp. 1-9, downloaded Aug. 17, 2010.
Dziarski, R., "Cell-bound albumin is the 70-kDa peptidoglycan-, lipopolysaccharide-, and lipoteichoic acid-binding protein on lymphocytes and macrophages", The Journal of Biological Chemistry, vol. 269, No. 32, p. 20431-20436, (1994).

Peters Jr. T., "5-Metabolism: Albumin in the body", All About Albumin Biochemistry, Genetics, and Medical Applications, Chapter 5, pp. 188-250, (1995).
Vlassara, H. et al., "High-affinity-receptor-mediated uptake and degradation of glucose-modified proteins: A potential mechanism for the removal of senescent macromolecules", Proceeding of the National Academy of Science, USA, Biochemistry, vol. 82, pp. 5588-5592, (1985).
Wade, N., "Purging cells in mice is found to combat aging ills", New York Times, found at NYTimes.com, pp. 1-3, (2011).
Roll, P. et al., "Anti-CD20 therapy in patients with rheumatoid arthritis", Arthritis & Rheumatism, vol. 58, No. 6, pp. 1566-1575, (2008).
Kajstura J. et al., "Myocyte turnover in the aging human heart", Circulation Research, vol. 107, pp. 1374-1386, (2010).
Baker, D.J. et al., "Clearance of p16Ink4a-positive senescent cells delays ageing-associated disorders", Nature, vol. 479, pp. 232-236, (2011).
Breyer, V. et al., "Intracellular glycation of nuclear DNA, mitochondrial DNA, and cytosolic proteins during senescence-like growth arrest", DNA Cell Biology, vol. 30, No. 9, pp. 681-689, (2011).
Ravelojaona, V. et al., "Expression of senescence-associated beta-galactosidase (SA-beta- Gal) by human skin fibroblasts, effect of advanced glycation end-products and fucose or rhamnose-rich polysaccharides", Archives of Gerontology and Geriatrics, vol. 48, issue 2, pp. 151-154, (2009).
International Search Report dated Apr. 26, 2012 for PCT application No. PCT/US2011/053399.
International Search Report dated Jun. 13, 2012 for PCT application No. PCT/US2011/061387.
Wautier, J.-L. et al., "Advanced glycation end products (AGEs) on the surface of diabetic erythrocytes bind to the vessel wall via a specific receptor inducing oxidant stress in the vasculature: A link between surface-associated AGEs and diabetic complications", Proc. Natl. Acad. Sci. USA, vol. 91, No. 16, pp. 7742-7746, (1994).
Siegel, R. J. et al., "Ultrasonic plaque ablation: A new method for recanalization of partially or totally occluded arteries", Circulation, vol. 78, No. 6, pp. 1443-1448, (1988).
International Search Report dated Jun. 27, 2012 for PCT application No. PCT/US2012/031446.
Immuno, Catalog No. 637061, 637062, "Mouse, anti-age (advanced glycation end products), monoclonal antibody", http://www.mpbio.com/detailed_info.php?family_key=0863706, 2 pages, accessed Jul. 26, 2012.
Ahmed, E. K. et al., "Protein modification and replicative senescence of WI-38 human embryonic fibroblasts", Aging Cell, vol. 9, pp. 252-272, (2010).
Vlassara, H. et al., "Advanced glycosylation endproducts on erythrocyte cell surface induce receptor- mediated phagocytosis by macrophages", J. Exp. Med., The Rockefeller University Press, vol. 166, pp. 539-549, (1987).
Yang, Z. et al., "Two novel rat liver membrane proteins that bind advanced glycosylation endproducts: Relationship to macrophage receptor for glucose-modified proteins", J. Exp. Med., The Rockefeller University Press, vol. 174, pp. 515-524, (1991).
Viassara, H. et al., "Advanced glycation endproducts promote adhesion molecule (VCAM-1, ICAM-1) expression and atheroma formation in normal rabbits", Molecular Medicine, vol. 1, No. 4, pp. 447-456, (1995).
Vaysse, J. et al., "Adhesion and erythrophagocytosis of human senescent erythrocytes by autologous monocytes and their inhibition by β-galactosyl derivatives", Proc. Natl. Acad. Sci. USA, Cell Biology, vol. 83, pp. 1339-1343, (1986).
Li, Y. M. et al., "Prevention of cardiovascular and renal pathology of aging by the advanced glycation inhibitor aminoguanidine", Proc. Natl. Acad. Sci. USA, Medical Sciences, vol. 93, pp. 3902-3907, (1996).
Manesso, E. et al., "Dynamics of B-cell turnover: evidence for β-cell turnover and regeneration from sources of β-cells other than β-cell replication in the HIP rat", American Journal of Physiology—Endocrinology and Metabolism, vol. 297, pp. E323-E330, (2009).
Stepanov, A.V. et al., "Design of targeted B cell killing agents", PLoS One, vol. 6, issue 6, e20991, pp. 1-10, (2011).

(56) References Cited

OTHER PUBLICATIONS

Fact Sheet, "Targeted Cancer Therapies", www.cancer.gov/cancertopics/factsheet/Therapy/Fs7_49.pdf, pp. 1-8, (2012).
Kay, M.M. "Generation of senescent cell antigen on old cells initiates IgG binding to a neoantigen", Cellular and Molecular Biology (Noisy-le-Grand, France), vol. 39, no. 2, pp. 131-153, (1993), Abstract Only.
Cirocchi, R. et al., "Meta-analysis of thyroidectomy with ultrasonic dissector versus conventional clamp and tie", World Journal of Surgical Oncology, vol. 8, No. 112, pp. 1-7, (2010).
Lingeman, J.E. et al., "Current perspective on adverse effects in shock wave lithotripsy", White Paper, American Urological Association Education and Research, found at www.auanet.org/content/guidelines-and-quality-care/clinical-guidelines/main-reports/whitepaper.pdf, 17 pages, (2009).
de Groot, K. et al., "Vascular endothelial damage and repair in antineutrophil cytoplasmic antibody associated vasculitis", Arthritis & Rheumatism, vol. 56, No. 11, pp. 3847-3853, (2007).
Imani, F. et al., "Advanced glycosylation endproduct-specific receptors on human and rat t-lymphocytes mediate synthesis of interferon γ: role in tissue remodeling", J. Exp. Med., vol. 178, pp. 2165-2172, (1993).
Kirstein, M. et al., "Receptor-specific induction of insulin-like growth factor I in human monocytes by advanced glycosylation end product-modified proteins", J. Clin. Invest., vol. 90, pp. 439-446, (1992).
Le Grand, F. et al., "Skeletal muscle satellite cells and adult myogenesis", Curr. Opin. Cell Biology, vol. 19, No. 6, pp. 628-633, (2007).
Sasaki, M. et al., "Mesenchymal stem cells are recruited into wounded skin and contribute to wound repair by transdifferentiation into multiple skin cell type", The Journal of Immunology, vol. 180, pp. 2581-2587, (2008).
Misur, I. et al., "Advanced glycation endproducts in peripheral nerve in type 2 diabetes with neuropathy", Acta Diabetol, vol. 41, pp. 158-166, (2004).
Saltykov, B.B., "Mechanisms of development of diabetic macroangiopathy", Arkh Patol., vol. 63, No. 2, pp. 21-26, (2001), Abstract Only.
Grossin, N. et al., "Red blood cell adhesion in diabetes mellitus is mediated by advanced glycation end product receptor and is modulated by nitric oxide", Biorheology, vol. 46, No. 1, pp. 63-72, (2009).
Liang, Y. et al., "Rituximab for children with immune thrombocytopenia: A systematic review", PLoS One, vol. 7, issue 1, pp. 1-11, (2012).
Fehrenbach, H. et al., "Up-regulated expression of the receptor for advanced glycation end products in cultured rat hepatic stellate cells during transdifferentiation to myofibroblasts", Hepatology, vol. 34, No. 5, pp. 943-952, (2001).
Agostini, A. et al., "Targeted cargo delivery in senescent cells using capped mesoporous silica nanoparticles", Angewandte Chemie International Edition, vol. 51, p. 10556-10560, (2012).
Larson, R.A. et al., "Tumor lysis syndrome: Definition, pathogenesis, clinical manifestations, etiology and risk factors", found at www.uptodate.com/contents/tumor-lysis-syndrome-definition-pathogenesis-clinical-manifestations-etiology-and-risk-factors?detectedLanguage=en&source=search_result&search=tumor+lysis+syndrome&selectedTitle=2~69&provider=noProvider, pp. 1-4, printed on Jun. 11, 2013.
Hansel, T.T. et al., "The safety and side effects of monoclonal antibodies", Nature Reviews, vol. 9, pp. 325-337, (2010).
Nass, N. et al., "Advanced glycation end products, diabetes and ageing", Zeitschrift fur Gerontologie und Geriatrie, vol. 40, issue 5, pp. 349-356, (2007).
Wautier, J-L. et al., Protein Glycation: "A firm link to endothelial cell dysfunction", Circulation Research, Journal of the American Heart Association, vol. 95, pp. 233-238, (2004).
Meuter, A. et al., "Markers of cellular senescence are elevated in murine blastocysts cultured in vitro: molecular consequences of culture in atmospheric oxygen", Journal of Assisted Reproduction and Genetics, vol. 31, issue 10, pp. 1259-1267, (2014).
Freund, A. et al., "Inflammatory networks during cellular senescence: causes and consequences", Trends in Molecular Medicine, vol. 16, No. 5, pp. 238-246, (2010).
Hadrabová, J. et al., "Chicken immunoglobulins for prophylaxis: Effect of inhaled antibodies on inflammatory parameters in rat airways", Journal of Applied Biomedicine, 4 pages, Available online May 5, 2014.
Ferraccioli, G. et al., "Interleukin-1β and Interleukin-6 in arthritis animal models: Roles in the early phase of transition from acute to chronic inflammation and relevance for human rheumatoid arthritis", Molecular Medicine, vol. 16, issue 11-12, pp. 552-557, (2010).
Zhao, Y. et al., "The bovine antibody repertoire", Developmental & Comparative Immunology, vol. 30, issues 1-2, pp. 175-186, (2006).
Wagner, B. et al., "The complete map of the Ig heavy chain constant gene region reveals evidence for seven IgG isotypes and for IgD in the horse", Journal of Immunology, vol. 173, No. 5, pp. 3230-3242, (2004).
Strietzel, C.J. et al., "In vitro functional characterization of feline IgGs", Veterinary Immunology and Immunopathology, vol. 158, issues 3-4, pp. 214-223, (2014).
Patel, M. et al., "Sequence of the dog immunoglobulin alpha and epsilon constant region genes", Immunogenetics, vol. 41, issue 5, pp. 282-286, (1995).
Maass, D.R. et al., "Alpaca (Lama pacos) as a convenient source of recombinant camelid heavy chain antibodies (VHHs)", Journal of Immunology Methods, vol. 324, issues 1-2, pp. 13-25, (2007).
European Search Report dated Sep. 12, 2014 for EP application No. EP14170802.4-1408.
Fessler, J. et al., "Senescent T cells promote bone loss in rheumatoid arthritis", Abstracts of the American College of Rheumatology/Association of Rheumatology Health Professionals, Annual Scientific Meeting, Washington, DC, Nov. 9-14, 2012, Arthritis & Rheumatism, vol. 64, supplement 10, p. 2312, (2012) found at http://blackwellpublishing.com/acrmeeting/abstract.asp?MeetingID=789&id=103040.
Weyand, C.M. et al., Abstract of "T-cell aging in rheumatoid arthritis", Current Opinion in Rheumatology, vol. 26, No. 1, pp. 93-100, (2014) found at http://www.ncbi.nlm.nih.gov/m/pubmed/24296720/.
Dvergsten, J. et al., "Prevalence of functionally active, senescent T cells in juvenile idiopathic arthritis", Abstracts of the American College of Rheumatology/Association of Rheumatology Health Professionals, Annual Scientific Meeting, Philadelphia, Oct. 16-21, 2009, Arthritis & Rheumatism, vol. 60, supplement 10, p. 1313, (2009), found at http://blackwellpublishing.com/acrmeeting/abstract.asp?MeetingID=761&id=80937.
Definition of "Dissociation constant" printed from Wikipedia, the free encyclopedia on Sep. 17, 2014 found at http://en.wikipedia.org/wiki/Dissociation_constant.
Sigma-Aldrich product specification of "Na, Na-Bis(carboxymethyl)-L-lysine trifluoroacetate salt 95% (TLC)", found at http://sigmaaldrich.com/catalog/product/sigma/c3205?lang=en&region=US, printed on Sep. 17, 2014.
"Pulmatrix demonstrates iSPERSE capabilities for inhaled dry powder delivery of antibiotics and antibodies", data presented at Respiratory Drug Delivery 2012, 3 pages, printed on Sep. 4, 2014, found at http://businesswire.com/news/home/20120515005279/en/Pulmatrix-Demonstrates-iSPERSE-Capabilities-Inhaled-Dry-Powder#. VEgU4hauNbs.
Chan, A.C. et al., "Therapeutic antibodies for autoimmunity and inflammation", Nature Reviews Immunology, vol. 10, pp. 301-316, (2010).
Pradat, P. F. et al., "Abnormalities of satellite cells function in amyotrophic lateral sclerosis", Amyotrophic Lateral Sclerosis, vol. 12, No. 4, pp. 264-271, (2011).
Tchkonia, T. et al., "Cellular senescence and the senescent secretory phenotype: therapeutic opportunities", The Journal of Clinical Investigation, vol. 123, No. 3, pp. 966-972, (2013).
Kitada, K. et al., "Aldosterone induces p21-regulated apoptosis via increased synthesis and secretion of tumour necrosis factor-α in

(56) References Cited

OTHER PUBLICATIONS human proximal tubular cells", Clinical and Experimental Pharmacology and Physiology, vol. 39, No. 10, pp. 858-863, (2012).
Definition of "TNF inhibitor", printed from Wikipedia, the free encyclopedia on Oct. 4, 2014, 4 pages, found at http://en.wikipedia.org/wiki/TNF_inhibitor?oldid=628250399.
Definition of "Etanercept", printed from Wikipedia, the free encyclopedia on Aug. 24, 2014, 6 pages, found at http://en.wikipedia.org/wiki/Etanercept?oldid=622648157.
Abbvie, Inc., "Humira adalimumab: Learn about Humira", found at https://www.humira.com/rheumatoid-arthritis, 7 pages, printed on Aug. 11, 2014.
Abbvie, Inc., "Medication Guide for Humira", found at https://www.humira.com/rheumatoid- arthritis, 9 pages, printed on Aug. 11, 2014.
Abbvie, Inc., "Humira: A biologic that targets and helps block TNF-alpha", found at https://www.humira.com/rheumatoid-arthritis/how-humira-works-for-ra, 8 pages, printed on Aug. 11, 2014.
Abbvie, Inc., "How Humira (adalimumab) works video transcript", found at https://www.humira.com/rheumatoid-arthritis/how-humira-works-video-transcript, 5 pages, printed on Aug. 11, 2014.
Abbvie, Inc., "Humira and methotrexate-a combination that has demonstrated results", found at https://www.humira.com/rheumatoid-arthritis/humira-and-methotrexate, 7 pages, printed on Aug. 11, 2014.
Madhur, M.S. et al., "Senescent T cells and hypertension: New ideas about old cells", Hypertension, vol. 62, pp. 13-15, (2013).
James, P. E. et al., "Vasorelaxation by red blood cells and impairment in diabetes: Reduced nitric oxide and oxygen delivery by glycated hemoglobin", Circulation Research, vol. 94, pp. 976-983, (2004).
Shibayama, R. et al., "Autoantibody against N(epsilon)-(carboxymethyl)lysine: an advanced glycation end product of the Maillard reaction", Diabetes, vol. 48, No. 9, pp. 1842-1849, (1999).
Bumol, T.F. et al., "Monoclonal antibody and an antibody-toxin conjugate to a cell surface proteoglycan of melanoma cells suppress in vivo tumor growth", Proceeding of the National Academy of Science, vol. 80, pp. 529-533, (1983).
"AGEs (all species) antibody—Product Details", Antibodies Online, 4 pages, found at www.web.archive.org/web/20081229071154/http://www.antibodies-online.com/antibody/289931/AGEs+All+Species/, printed on Dec. 10, 2014.
"Antibody Engineering", Fusion Antibodies, 2 pages, found at www.web.archive.org/web/20080628225818/http://www.fusionantibodies.com/index.cfm/area/information/page/engineering?, printed on Dec. 16, 2014.
Hargreaves, R.E.G. et al., "Selective depletion of activated T cells: the CD40L-specific antibody experience", TRENDS in Molecular Medicine, vol. 10, No. 3, pp. 130-135, (2004).
Leinenga, G. et al., "Scanning ultrasound removes amyloid-ß and restores memory in an Alzheimer's disease mouse model", Science Translational Medicine, vol. 7, issue 278, pp. 1-11, (2015).
Peppa, M. et al., "Glucose, advanced glycation end products, and diabetes complications: What is new and what works", Clinical Diabetes, vol. 21, No. 4, pp. 186-187, (2003).
Lv, Y. et al., "Low-intensity ultrasound combined with 5-aminolevulinic acid administration in the treatment of human tongue squamous carcinoma", Cellular Physiology and Biochemistry, vol. 30, pp. 321-333, (2012).
Campisi, J. et al., "Cellular senescence: when bad things happen to good cells", Nature Reviews: Molecular Cell Biology, vol. 8, pp. 729-749, (2007).
"ALSUntangled No. 23: The Rife Machine and retroviruses", Amyotrophic Lateral Sclerosis and Frontotemporal Degeneration, vol. 15, pp. 157-159, (2014).
Roylance, D., "Mechanical properties of materials", pp. 1-128, (2008), available at www.web.mit.edu/course/3/3.225/book.pdf.
Vidarsson, G. et al., "IgG subclasses and allotypes: from structure to effector functions", Frontiers in Immunology, vol. 5, article 520, pp. 1-17, (2014).

Lin, H-T. et al., "Stem cell therapy: an exercise in patience and prudence", Philosophical Transactions of the Royal Society B: Biological Sciences 368, (2013).
Waldmann, T.A., "Immunotherapy:past, present and future", Nature Medicine, vol. 9, No. 3, pp. 269-277, (2003).
Okamoto, T. et al., "Advanced glycation end products induce angiogenesis in vivo", Microvascular Research, vol. 63, pp. 186-195, (2002).
Nagal, R. et al., "Application of monoclonal antibody libraries for the measurement of glycation adducts", Biochemical Society Transactions, vol. 31, part 6, pp. 1438-1440, (2003).
De Genst, E. et al., "Antibody repertoire development in camelids", Developmental and Comparative Immunology, vol. 30, pp. 187-198, (2006).
Griffin, L.M. et al., "Analysis of hevy and light chain sequences of conventional camelid antibodies from Camelus dromedarius and Camelus bactrianus species", Journal of Immunological Methods, vol. 405, pp. 35-46, (2014).
Hamers-Casterman, C. et al., "Naturally occurring antibodies devoid of light chains", Nature, vol. 363, pp. 446-448, (1993).
Muyldermans, S. et al., "Sequence and structure of VH domain from naturally occurring camel heavy chain immunoglobulins lacking light chains", Protein Engineering, vol. 7, No. 9, pp. 1129-1135, (1994).
Nguyen, V. K. et al., "Camel heavy-chain antibodies: diverse germline VHH and specific mechanisms enlarge the antigen-binding repertoire", The EMBO Journal, vol. 19, No. 5, pp. 921-930, (2000).
Kirstein, et al., "Advanced protein glycosylation induces transendothelial human monocyte chemotaxis and secretion of platelet-derived growth factor: roll in vascular disease of diabetes and aging", PNAS, vol. 87, No. 22, pp. 9010-9014, (1990).
Invitation to Pay Additional Fees and Partial International Search Report dated Jan. 13, 2016 for PCT application No. PCT/US2015/050154.
Feldmann, M. et al., "Anti-TNFalpha therapy of rheumatoid arthritis: What have we learned?", Annual Review of Immunology, vol. 19, pp. 163-196, (2001).
Drinda, S. et al., "Identification of the advanced glycation end products N-carboxymethyllysine in the synovial tissue of patients with rheumatoid arthritis", Annals of the Rheumatic Diseases, vol. 61, No. 6, pp. 488-492, (2002).
Ahmad, S. et al., "Preferential recognition of epitopes on AGE-IgG by the autoantibodies in rheumatoid arthritis patients", Human Immunology, vol. 74, No. 1, pp. 23-27, (2013).
Johns, L.D., "Nonthermal effects of therapeutic ultrasound: The frequency resonance hypothesis", Journal of Athletic Training, vol. 37, No. 3, pp. 293-299, (2002).
Wang, B-L. et al., "Identification of monoclonal antibody of advanced glycation end products", Chinese Journal of Arteriosclerosis, vol. 14, No. 5, pp. 409-412, (2006).
Wang, J.C. et al., "Aging and Atherosclerosis mechanisms, functional consequences, and potential therapeutics for cellular senescence", Circulation Research, vol. 111, pp. 245-259, (2012).
Minamino, T. et al., "Vascular cell senescence contribution to Atherosclerosis", Circulation Research, vol. 100, pp. 15-26, (2007).
Isoda, K. et al., "Glycated LDL increases monocyte CC chemokine receptor 2 expression and monocyte chemoattractant protein-1-mediated chemotaxis", Atherosclerosis, vol. 198, No. 2, pp. 307-312, (2008).
Roos, C.M. et al., "Chronic senolytic treatment alleviates established vasomotor dysfunction in aged or atherosclerotic mice", Aging Cell, 8 pages, (2016).
Hall, B.M. et al., "Aging of mice is associated with p16(ink4a)- and β-galactosidase-positive macrophage accumulation that can be induced in young mice by senescent cells", Aging, vol. 8, No. 7, pp. 1-18, (2016).
Mera, K. et al., "An autoantibody against NE-(carboxyethyl)lysine (CEL): Possible involvement in the removal of CEL-modified proteins by macrophages", Biochemical and Biophysical Research Communications, vol. 407, pp. 420-425, (2011).

(56) References Cited

OTHER PUBLICATIONS

Reddy, S. et al., "N$^\epsilon$-(Carboxymethyl)lysine is a dominant advanced glycation end product (AGE) antigen in tissue proteins", Biochemistry, vol. 34, p. 10872-10878, (1995).
Katcher, H.L., "Studies that shed new light on aging", Biochemistry (Moscow), vol. 78, No. 9, pp. 1061-1070, (2013).
Naylor, R.M. et al., "Senescent Cells: A novel therapeutic target for aging and age-related diseases", Clinical Pharmacology & Therapeutics, vol. 93, No. 1, pp. 105-116, (2013).
Beaulieu, L-P. et al., "Inhibitory effect of the cree traditional medicine wiishichimanaanh (vaccinium vitis-idaea) on advanced glycation endproduct formation: identification of active principles", Phytotherapy Research, vol. 24, pp. 741-747, (2010).
Ulrich, P. et al., "Protein glycation, diabetes, and aging", Recent Progress in Hormone Research, vol. 56, pp. 1-21, (2000).
Van Heijst, J.W.J. et al., "Advanced glycation end products in human cancer tissues: detection of N$^\epsilon$-(carboxymethyl)lysine and argpyrimidine", Annals of the New York Academy of Sciences, vol. 1043, pp. 725-733, (2005).
Fielding, R.A. et al., "Sarcopenia: An undiagnosed condition in older adults. Current consensus definition: Prevalence, etiology, and consequences", Journal of the American Medical Directors Association, vol. 12, No. 4, pp. 249-256, (2011).
Definition of "Sarcopenia", printed from Wikipedia, the free encyclopedia on Jul. 25, 2016, 5 pages, found at http://en.wikipedia.org/wiki/Sarcopenia.
"What is Sarcopenia?", International Osteoporosis Foundation, 2 pages, found at www.iofbonehealth.org/what-sarcopenia, (2014).
"Sarcopenia with aging", Webmd, 2 pages, found at www.webmd.com/healthy-aging/sarcopenia-with-aging, (2014).
Definition of "Keyhole limpet hemocyanin", printed from Wikipedia, the free encyclopedia on Jul. 25, 2016, 4 pages, found at https://en.wikipedia.org/wiki/Keyhole_limpet_hemocyanin.
Cell Biolabs, Inc., "CML-BSA Product Data Sheet", 3 pages, found at http://www.cellbiolabs.com/sites/default/files/STA-314-cml-bsa.pdf, (2010).
Cell Biolabs, Inc., "CML (N-epsilon-(Caboxymethyl)Lysine) Assays and Reagents", 1 page, found at http://www.cellbiolabs.com/cml-assays, (2014).
Cruz-Jentoft, A.J. et al., "Sarcopenia: European consensus on definition and diagnosis", Age and Ageing, vol. 39, pp. 412-423, (2010).
Rolland, Y. et al., "Sarcopenia: Its assessment, etiology, pathogenesis, consequences and future perspectives", The Journal of Nutrition, Health & Aging, vol. 12, No. 7, pp. 433-450, (2008).
Centers for Disease Control and Prevention, "Vaccine excipient and media summary", 4 pages, found at www.cdc.gov/vaccines/pubs/pinkbook/downloads/appendices/B/excipient-table- 2.pdf?utm_content=buffer4538f&utm_medium=social&utm_source=linkedin.com&utm_campai gn=buffer, (2015).
Definition of "N(6)-Carboxymethyllysine", printed from Wikipedia, the free encyclopedia on Dec. 8, 2013, 1 page, found at http://en.wikipedia.org/wiki/N(6)-Carboxymethyllysine.
Definition of "Lysine", printed from Wikipedia, the free encyclopedia on Dec. 8, 2013, 1 page, found at http://en.wikipedia.org/wiki/Lysine.
Jarvis, L.M., "Rethinking antibody-drug conjugates", Chemical & Engineering News, vol. 90, issue 25, pp. 12-18, (2012).
Mullin, R., "Cell-free approach to antibody-drug conjugates", Chemical & Engineering News, vol. 91, issue 44, 2 pages, (2013).
Thayer, A.M., "Building antibody-drug conjugates", Chemical & Engineering News, vol. 92, issue 3, pp. 13-21, (2014).
Feige, M.J. et al., "The structural analysis of shark IgNAR antibodies reveals evolutionary principles of immunoglobulins", Proceedings of the National Academy of Sciences, vol. 111, No. 22, pp. 8155-8160, (2014).
Philipot, D. et al.,"p16$^{INK4a}$ and its regulator miR-24 link senescence and chondrocyte terminal differentiation-associated matrix remodeling in osteoarthritis", Arthritis Research & Therapy, vol. 16, No. 1, pp. 1-12, (2014).
International Search Report and Written Opinion dated Mar. 31, 2016 for PCT application No. PCT/US2015/050154.
Zhu, Y. et al., "The achilles' heel of senescent cells: from transcriptome to senolytic drugs", Aging Cell, vol. 14, pp. 644-658, (2015).
Zhu, L. et al., "Immunization with advanced glycation end products modified low density lipoprotein inhibits atherosclerosis progression in diabetic apoE and LDLR null mice", Cardiovascular Diabetology, vol. 13, No. 151, pp. 1-12, (2014).
Denardo, S.J. et al., "Development of tumor targeting bioprobes ($^{111}$in-chimeric L6 monoclonal antibody nanoparticles) for alternating magnetic field cancer therapy", Clinical Cancer Research, vol. 11, 19 supplemental, p. 7087s-7092s, (2005).
Chen, L. et al., "Cytolysis of human erythrocytes by a covalent antibody-selenium immunoconjugate", Free Radical Biology & Medicine, vol. 19, No. 6, pp. 713-724, (1995).
Yuan, Y. et al., "Advanced glycation end products (AGEs) increase human mesangial foam cell formation by increasing Golgi SCAP glycosylation in vitro", American Journal of Physiology-Renal Physiology, vol. 301.1, pp. F236-F243, (2011).
Hashimoto, M. et al., "Elimination of p19$^{ARF}$-expressing cells enhances pulmonary function in mice", JCI Insight, vol. 1, No. 12, pp. 1-15, (2016).
Yan, S.F. et al., "Soluble RAGE: Therapy & biomarker in unraveling the RAGE axis in chronic disease and aging", Biochemical Pharmacology, vol. 79, No. 10, pp. 1379-1386, (2010).
Xue, J. et al., "Advanced glycation end product (AGE) recognition by the receptor for AGEs (RAGE)", Structure, vol. 19, No. 5, pp. 722-732, (2011).
Chang, J. et al., "Clearance of senescent cells by ABT263 rejuvenates aged hematopoietic stem cells in mice", Nature Medicine, vol. 22, No. 1, pp. 78-83, (2016).
Geiger, H., "Depleting senescent cells to combat aging", Nature Medicine, vol. 22, No. 1, pp. 23-24, (2016).
Ni, J. et al., "Plasma protein pentosidine and carboxymethyllysine, biomarkers for age-related macular degeneration", Molecular & Cellular Proteomics, vol. 8, No. 8, pp. 1921-1933, (2009).
R&D Systems, a biotechne brand, product specification of "Carboxymethyl Lysine Antibody", found at https://www.rndsystems.com/products/carboxymethyl-lysine-antibody- 318003_mab3247, 1 page, (2015).
Schalkwijk, C.G. et al., "Increased accumulation of the glycoxidation product Nε-(carboxymethyl)lysine in hearts of diabetic patients: generation and characterization of a monoclonal anti-CML antibody", Biochimica et Biophysica Acta (BBA)-Molecular and Cell Biology of Lipids, vol. 1636, No. 2, pp. 82-89, (2004).
LaPak, K.M. et al., "The molecular balancing act of p16$^{INK4a}$ in cancer and aging", Molecular Cancer Research, vol. 12, No. 2, pp. 167-183, (2013).
Larsen, S.A. et al., "Glucose metabolite glyoxal induces senescence in telomerase-immortalized human mesenchymal stem cells", Chemistry Central Journal, vol. 6, No. 18, pp. 1-13, (2012).
Ahmed, M.U. et al., "Nε-(carboxymethyl)lysine, a product of the chemical modification of proteins by methylglyoxal, increases with age in human lens proteins", Biochemical Journal, vol. 324, pp. 565-570, (1997).
Dunn, J.A. et al., "Age-dependent accumulation of N$^\epsilon$-(Carboxymethyl)lysine and N$^\epsilon$-(Carboxymethyl)hydroxylysine in human skin collagen", Biochemistry, vol. 30, pp. 1205-1210, (1991).
Finco, A.B. et al., "Generation and characterization of monoclonal antibody against advanced glycation end products in chronic kidney disease", Biochemistry and Biophysics Reports, vol. 6, pp. 142-148, (2016).
International Search Report and Written Opinion dated Aug. 10, 2016 for PCT application No. PCT/US2016/034880.
Liu, H. et al., "Abstract 154: Vaccination using advanced glycation end product of low-density lipoprotein pulsed dendritic cells reduces atherosclerosis in diabetic apoe-'- mice", Arteriosclerosis, Thrombosis, and Vascular Biology, pp. 1-4, (2012).
Mashitah, M.W. et al., "Immunization of AGE-modified albumin inhibits diabetic nephropathy progression in diabetic mice", Diabetes, Metabolic Syndrome and Obesity: Targets and Therapy, vol. 8, pp. 347-355, (2015).

(56) References Cited

OTHER PUBLICATIONS

Sayej, W.N. et al., "Advanced glycation end products induce obesity and hepatosteatosis in CD-1 wild-type mice", BioMed Research International, vol. 6, No. 39, pp. 1-12, (2016).
Srikanth, V. et al., "Advanced glycation endproducts and their receptor RAGE in alzheimer's disease", Neurobiology of Aging, vol. 32, No. 5, pp. 763-777, (2011).
International Search Report and Written Opinion dated Dec. 2, 2016 for PCT application No. PCT/US2016/039076.
Fu, M-X. et al., "The advanced glycation end product, N-(Carboxymethyl)lysine, is a product of both lipid peroxidation and glycoxidation reactions", The Journal of Biological Chemistry, vol. 271, No. 17, pp. 9982-9986, (1996).
Jorgensen, L. et al., "The relationship between atherosclerosis of the thoracic aorta and renal scarring in an autopsy material", Acta Pathol Microbiol Immunol Scand A., vol. 93, No. 5, pp. 251-255, (1985) Abstract Only.
"Senescent cells drive plaque formation in animal models of atherosclerosis, research shows", Mayo Clinic, pp. 1-2, (2016), found at www.news-medical.net/news/20161027/Senescent-cells-drive-plaque-formation-in-animal-models-of-atherosclerosis-research-shows.aspx.
Baker, D.J. et al., "Naturally occurring p16$^{Ink4a}$-positive cells shorten healthy lifespan", Nature, vol. 530, issue 7589, pp. 184-189, (2016).
Raquib, R., "The key to youth via senescent cell removal", Young Investigators Review, pp. 1-4, (2017), found at sbyireview.com/2017/01/23/the-key-to-youth-via-senescent-cell-removal.
Tiner, S., "Mayo clinic research links senescent cells and atherosclerosis progression", Mayo Clinic News Network, pp. 1-3, (2016), found at newsnetwork.mayoclinic.org/discussion/mayo-clinic-research-links-senescent-cells-and-atherosclerosis-progression.
Wiley, C., "Aging Fundamentals: Cellular senescence", Science of Aging Blog at the Buck Institute, pp. 1-4, (2015), found at sage.buckinstitute.org/aging-fundamentals-cellular-senescence.
Arichika, S. et al., "Correlation of retinal arterial wall thickness with atherosclerosis predictors in type 2 diabetes without clinical retinopathy", British Journal of Ophthalmology, vol. 101, pp. 69-74, (2017).
Lin, Z. et al., "Vaccination against AGE-LDL significant attenuates atherosclerosis in diabetic apoe mice", Heart, vol. 97, No. 21, supplement 3, p. A18, (2011) Abstract Only.
Thompson, L.V., "Age-related muscle dysfunction", Experimental Gerontology, vol. 44, pp. 106-111, (2009).
Sun, K. et al., "Elevated serum carboxymethyl-Lysine, an advanced glycation end product, predicts severe walking disability in older women: The women's health and aging study 1", Journal of Aging Research, vol. 2012, pp. 1-8, (2012).
Kislinger, T. et al., "N$^\epsilon$-(Carboxymethyl)Lysine adducts of proteins are ligands for receptor for advanced glycation end products that activate cell signaling pathways and modulate gene expression", The Journal of Biological Chemistry, vol. 274, No. 44, pp. 31740-31749, (1999).
Nakayama, H. et al., "Production and characterization of antibodies to advanced glycation products on proteins", Biochemical and Biophysical Research Communications, vol. 162, No. 2, pp. 740-745, (1989).
Gupta, R.K., "Aluminum compounds as vaccine adjuvants", Advanced Drug Delivery Review, vol. 32, No. 3, pp. 155-172, (1998), Abstract Only.
Tracy, J.M. et al., "Preservatives for poliomyelitis (Salk) vaccine II: Formaldehyde and esters of p-hydroxybenzoic acid", Journal of Pharmaceutical Sciences, vol. 53, Issue 6, pp. 659-663, (1964), Abstract Only.
Koito, W. et al., "Conventional antibody against N$^\epsilon$-(Carboxymethyl)Lysine (CML) shows cross- reaction to N$^\epsilon$-(Carboxyethyl)Lysine (CEL): Immunochemical quantification of CML with a specific antibody", The Journal of Biochemistry, vol. 135, No. 6, pp. 831-837, (2004).
Product Description of "Anti-Advanced Glycation End Products (AGE), Carboxy-Methyl Lysine (Cml) [6C7] Antibody", Kerafast, www.kerafast.com/product/1779/anti-advanced-glycation-end-products-age-carboxy-methyl-lysine-cml-6c7-antibody, printed on Feb. 2, 2017.
Ikeda, K. et al., "N$^\epsilon$-(Carboxymethyl)lysine protein adduct is a major immunological epitope in proteins modified with advanced glycation end products of the maillard reaction", Biochemistry, vol. 35, No. 24, pp. 8075-8083, (1996).
Dunn, J.A. et al., "Oxidation of glycated proteins: Age-dependent accumulation of N$^\epsilon$- (Carboxymethyl)lysine in lens proteins", Biochemistry, vol. 28, No. 24, pp. 9464-9468, (1989).
Peppa, M. et al., "The role of advanced glycation end products in the development of atherosclerosis", Current Diabetes Reports, vol. 4, pp. 31-36, (2004).
Glenn, J.V. et al., "The role of advanced glycation end products in retinal ageing and disease", Biochimica Et Biophysica Acta, vol. 1790, No. 10. pp. 1109-1116, (2009).
European Search Report dated Feb. 21, 2017 for EP application No. 16198527.0.
Xu, M. et al., "Transplanted senescent cells induce an osteoarthritis-like condition in mice", The Journals of Gerontology Series A: Biological Sciences and Medical Sciences, pp. 1-6, (2016).
Ratliff, M. et al., "In senescence, age-associated B cells secrete TNFα and inhibit survival of B- cell precursors", Aging Cell, vol. 12, pp. 303-311, (2013).
Manestar-Blazic, T. et al., "The dynamic of senescent cells accumulation can explain the age- specific incidence of autoimmune diseases", Medical Hypotheses, vol. 73, pp. 667-669, (2009).
Tchkonia, T. et al., "Fat tissue, aging, and cellular senescence", Aging Cell, vol. 9, pp. 667-684, (2010).
Robbins, P. et al., "Scripps research, Mayo Clinic scientists find new class of drugs that dramatically increases healthy lifespan", The Scripps Research Institute, pp. 1-3, found at www.scripps.edu/news/press/2015/20150309agingcell.html, printed on Mar. 14, 2015.
Dorr, J.R. et al., "Synthetic lethal metabolic targeting of cellular senescence in cancer therapy", Nature, vol. 501, No. 7467, pp. 421-425, (2013).
Xu, M. et al., "Targeting senescent cells enhances adipogenesis and metabolic function in old age", eLife, vol. 4, pp. 1-20, (2015).
Minamino, T. et al., "Endothelial cell senescence in human atherosclerosis: Role of telomere in endothelial dysfunction", Circulation, vol. 105, issue 13, pp. 1541-1544, (2002).
Takino, J-I. et al., "Cancer malignancy is enhanced by glyceraldehyde-derived advanced glycation end-products", Journal of Oncology, vol. 2010, pp. 1-8, (2010).
Laberge, R-M. et al., "Epithelial-mesenchymal transition induced by senescent fibroblasts", Cancer Microenvironment, vol. 5, pp. 39-44, (2012).
Abe, R. et al., "Regulation of human melanoma growth and metastasis by AGE-AGE receptor interactions", Journal of Investigative Dermatology, vol. 122, No. 2, pp. 461-467, (2004). P
orporato, P.E. et al., "A mitochondrial switch promotes tumor metastasis", Cell Reports, vol. 8, pp. 754-766, (2014).
Boquio, A. et al., "Reversible cell cycle inhibition and premature aging features imposed by conditional expression of p16$^{ink4a}$", Aging Cell, vol. 14, pp. 139-147, (2015).
Nelson, G. et al., "A senescent cell bystander effect: senescence-induced senescence", Aging Cell, vol. 11, pp. 345-349, (2012).
Rayess, H. et al., "Cellular senescence and tumor suppressor gene p16", International Journal of Cancer, vol. 130, No. 8, pp. 1715-1725, (2012).
Greenfieldboyce, N., "Boosting life span by clearing out cellular clutter", NPR.ORG, 4 pages, found at www.npr.org/sections/health-shots/2016/02/03/465354874/boosting-lifespan-by- clearing-out-cellular-clutter, printed on Feb. 4, 2016.
Matus, D.Q. et al., "Invasive cell fate requires G1 cell-cycle arrest and histone deacetylase- mediated changes in gene expression", Developmental Cell, vol. 35, pp. 162-174, (2015).
Stony Brook University, "Targeting invasive cells not dividing cells to halt cancer, study suggests", ScienceDaily, pp. 1-2, found at www.sciencedaily.com/releases/2015/10/151026181610.htm, (2015).
Liu, D. et al., "Senescent human fibroblasts increase the early growth of xenograft tumors via matrix metalloproteinase secretion", Cancer Research, vol. 67, No. 7, pp. 3117-3126, (2007).

(56) References Cited

OTHER PUBLICATIONS

Hoke, Z. "Belgian researchers discover way to block cancer metastasis", VOZ News, pp. 1-3, found at www.voanews.com/a/belgian-researchers-discover-way-to-block-cancer- metastasis/2453790.html, (2014).
Di, G-H. et al., "IL-6 secreted from senescent mesenchymal stem cells promotes proliferation and migration of breast cancer cells", PloS one, vol. 9, No. 11, pp. 1-15, (2014).
Huang, L-W. et al., "P16$^{ink4a}$overexpression predicts lymph node metastasis in cervical carcinomas", Journal of Clinical Pathology, vol. 65, pp. 117-121, (2012).
Romagosa, C. et al., "P16$^{ink4a}$overexpression in cancer: a tumor suppressor gene associated with senescence and high-grade tumors", Oncogene, vol. 30, pp. 2087-2097, (2011).
Terman, A. et al., "Mitochondrial turnover and aging of long-lived postmitotic cells: The mitochondrial-lysosomal axis theory of aging", Antioxidants & Redox Signaling, vol. 12, No. 4, pp. 503-535, (2010).
Ralph, A. et al., "P16 and HPV discordance in metastatic carcinoma of cervical lymph nodes of unknown primary", Clinical Case Reports, vol. 3, No. 10, pp. 817-818, (2015).
Hipkiss, A.R. "Aging, proteotoxicity, mitochondria, glycation, NAD+ and carnosine: possible inter-relationships and resolution of the oxygen paradox", Frontiers in Aging Neuroscience, vol. 2, article 10, pp. 1-6, (2010).
Bakala, H. et al., "Changes in rat liver mitochondria with aging Ion protease-like activity and N$^\epsilon$-carboxymethyllysine accumulation in the matrix", European Journal of Biochemistry, vol. 270, No. 10, pp. 2295-2302, (2003).
Leslie, M. "Suicide of aging cells prolongs life span in mice", Sciencemag.org, pp. 1-4, found at www.sciencemag.org/news/2016/02/suicide-aging-cells-prolongs-life-span-mice, (2016).
Eto, H. et al., "Selective imaging of malignant ascites in a mouse model of peritoneal metastasis using in vivo dynamic nuclear polarization-magnetic resonance imaging", Analytical Chemistry, vol. 88, pp. 2021-2027, (2016).
May Jr. K.F. et al., "Anti-human CTLA-4 monoclonal antibody promotes T-cell expansion and immunity in a hu-PBL-SCID model: a new method for preclinical screening of costimulatory monoclonal antibodies", Blood, vol. 105, pp. 1114-1120, (2005).
Schmitt, C.A. "Cellular senescence and cancer treatment", Biochimica et Biophysica Acta—Reviews on Cancer, vol. 1775, No. 1, pp. 5-20, (2007).
Gordon, R.R. et al., "Cellular senescence and cancer chemotherapy resistance", Drug Resistance Updates, vol. 15, No. 1-2, pp. 123-131, (2012).
Eyman, D. et al., "CCL5 secreted by senescent aged fibroblasts induces proliferation of prostate epithelial cells and expression of genes that modulate angiogenesis", Journal of Cellular Physiology, vol. 220, No. 2, pp. 376-381, (2009).
Nguyen, D.X. et al., "Metastasis: from dissemination to organ-specific colonization", Nature Reviews Cancer, vol. 9, No. 4, pp. 274-284, (2009).
Smit, M.A. et al., "Deregulating EMT and senescence: Double impact by a single twist", Cancer Cell, pp. 5-7, (2008).
Degenhardt, T.P. et al., "Chemical modification of proteins by methylglyoxal", Cellular and Molecular Biology (Noisy-le-Grand, France), vol. 44, No. 7, pp. 1139-1145, (1998) Abstract Only.
Gao, S.H. et al., "Monoclonal antibody humanness score and its applications", BMC Biotechnology, vol. 13, No. 1, pp. 1-12, (2013).
Clinicaltrials.gov, "A study evaluating the safety of ABT-263 in combination with etoposide/cisplatin in subjects with cancer", ClinicalTrials.gov, 4 pages, found at https://clinicaltrials.gov/ct2/show/NCT00878449?term=A+study+evaluating+the+safety+of+ABT-263+in+combination+with+etoposide%2Fcisplatin+in+subjects+with+cancer&rank=1, printed on Aug. 4, 2016.
Keating, D.J. "Mitochondrial dysfunction, oxidative stress, regulation of exocytosis and their. Relevance to neurodegenerative diseases", vol. 104, No. 2, pp. 298-305, (2008). Abstract Only.
Sas, K. et al., "Mitochondria, metabolic disturbances, oxidative stress and the kynurenine system, with focus on neurodegenerative disorders", Journal of the neurological sciences, vol. 257, No. 1, pp. 221-239, (2007). Abstract Only.
Ott, M. et al., "Mitochondria, oxidative stress and cell death", Apoptosis, vol. 12, No. 5, pp. 913-922, (2007). Abstract Only.
Trushina, E. et al., "Oxidative stress and mitochondrial dysfunction in neurodegenerative diseases", Neuroscience, vol. 145, No. 4, pp. 1233-1248, (2007). Abstract Only.
Moreira, P.I. et al., "Lipoic acid and N-acetyl cysteine decrease mitochondrial-related oxidative stress in Alzheimer disease patient fibroblasts", Journal of Alzheimer's Disease, vol. 12, No. 2, pp. 195-206, (2007). Abstract Only.
Yel, L. et al., "Thimerosal induces neuronal cell apoptosis by causing cytochrome c and apoptosis-inducing factor release from mitochondria", International Journal of Molecular Medicine, vol. 16, No. 6, pp. 971-977, (2005). Abstract Only.
Humphrey, M.L. et al., "Mitochondrial mediated thimerosal-induced apoptosis in a human neuroblastoma cell line (SK-N-SH)", Neurotoxicology, vol. 26, No. 3, pp. 407-416, (2005). Abstract Only.
Makani, S. et al., "Biochemical and molecular basis of thimerosal-induced apoptosis in T cells: a major role of mitochondrial pathway", Genes and Immunity, vol. 3, No. 5, pp. 270-278, (2002). Abstract Only.
Freitag, H. et al., "Inhibition of malate transport and activation of phosphate transport in mitochondria by ethylmercurithiosalicylate", FEBS Letters, vol. 117, No. 1, pp. 149-151, (1980). Citation Only.
Freitag, H. et al., "Ethylmercurithiosalicylate-a new reagent for the study of phosphate transport in mitochondria", FEBS Letters, vol. 114, No. 2, pp. 295-298, (1980). Citation Only.
Windham, G.C. et al., "Autism spectrum disorders in relation to distribution of hazardous air pollutants in the San Francisco bay area", Environmental Health Perspectives, pp. 1438-1444, (2006). Citation Only.
Ooe, H. et al., "Induction of reactive oxygen species by bisphenol A and abrogation of bisphenol A-induced cell injury by DJ-1", Toxicological Sciences, vol. 88, No. 1, pp. 114-126, (2005). Abstract Only.
Hanzel, C.E. et al., "Thallium induces hydrogen peroxide generation by impairing mitochondrial function", Toxicology and Applied Pharmacology, vol. 216, No. 3, pp. 485-492, (2006). Abstract Only.
Murugavel, P. et al., "Cadmium induced mitochondrial injury and apoptosis in vero cells: protective effect of diallyl tetrasufide from garlic", The International Journal of Biochemistry & Cell Biology, vol. 39, No. 1, pp. 161-170, (2007). Abstract Only.
Lasfer, M. et al., "Cadmium induces mitochondria-dependent apoptosis of normal human hepatocytes", Cell Biology and Toxicology, vol. 24, No. 1, pp. 55-62, (2008). Abstract Only.
Gash, D.M. et al., "Trichloroethylene: Parkinsonism and complex 1 mitochondrial Neurotoxicity", Annals of neurology, vol. 63, No. 2, pp. 184-192, (2008). Abstract Only.
Banerjee, N. et al., "Arsenic-induced mitochondrial instability leading to programmed cell death in the exposed individuals", Toxicology, vol. 246, No. 2, pp. 101-111, (2008). Abstract Only.
Partridge, M.A. et al., "Arsenic induced mitochondrial DNA damage and altered mitochondrial oxidative function: Implication for genotoxic mechanisms in mammalian cells", Cancer Research, vol. 67, No. 11, pp. 5239-5247, (2007). Abstract Only.
Santra, A. et al., "Arsenic induces apoptosis in mouse liver is mitochondria dependent and is abrogated by N-acetylcysteine", Toxicology and Applied Pharmacology, vol. 220, No. 2, pp. 146-155, (2007). Abstract Only.
Bouchard, H. et al., "Antibody-drug conjugates-A new wave of cancer drugs", Bioorganic & Medicinal Chemistry Letters, vol. 24, pp. 5357-5363, (2014).
Yang, H.M. et al., "Doxorubicin conjugated with a monoclonal antibody directed to a human melanoma-associated proteoglycan suppresses the growth of established tumor xenografts in nude mice", Proceeding of the National Academy of Science, vol. 85, pp. 1189-1193, (1988).

(56) References Cited

OTHER PUBLICATIONS

Childs, B.G. et al., "Senescent intimal foam cells are deleterious at all stages of atherosclerosis", Science, vol. 354, No. 6311, pp. 472-477, (2016).
Loaiza, N. et al., "Cellular senescence and tumor promotion: Is aging the key?", Biochimica et Biophysica Acta, vol. 1865, pp. 155-167, (2016).
Rodier, F. et al., "Four faces of cellular senescence", The Journal of Cell Biology, vol. 192, No. 4, pp. 547-556, (2011).
Shay, J.W. et al., "Hallmarks of senescence in carcinogenesis and cancer therapy", Oncogene, vol. 23, pp. 2919-2933, (2004).
Davalos, A.R. et al., "Senescent cells as a source of inflammatory factors for tumor progression", Cancer Metastasis Reviews, vol. 29, pp. 273-283, (2010).
Roninson, I.B., "Tumor cell senescence in cancer treatment", Cancer Research, vol. 63, pp. 2705-2715, (2003).
International Search Report and Written Opinion dated May 17, 2017 for PCT application No. PCT/US2017/018185.
Kobayashi, S. et al., "Overproduction of N(epsilon)—(carboxymethyl) lysine-induced neovascularization in cultured choroidal explant of aged rat", Biological & Pharmaceutical Bulletin, vol. 30, No. 1, pp. 133-138, (2007).
Foster, D. et al., "AGE metabolites: A biomarker linked to cancer disparity?" Cancer Epidemiology, Biomarkers and Prevention, vol. 23, No. 10, pp. 2186-2191, (2014).
Mir, A.R. et al., "Structural changed in histone H2A by methylglyoxal generate highly immunogenic amorphous aggregates with implications in auto-immune response in cancer", Glycobiology, vol. 26, No. 2, pp. 129-141, (2016).
Ko, S-Y. et al., "Cell migration is regulated by AGE-RAGE interaction in human oral cancer cells in vitro", PLOS One, vol. 9, No. 10, pp. 1-9, e0110542, (2014).
Chen, H. et al., "Advanced glycation end products increase carbohydrate responsive element binding protein expression and promote cancer cell proliferation", Molecular and Cellular Endocrinology, vol. 395, No. 1-2, pp. 69-78, (2014).
Mercado-Pimentel, M.E. et al., "The S100P/RAGE signaling pathway regulates expression of microRNA-21 in colon cancer cells", FEBS Letters, vol. 589, No. 18, pp. 2388-2393, (2015).
Product description, "Carboxymethyl Lysine Antibody", R&D Systems, a biotechne brand, catalog No. MAB3247, 1 page, found at https://resources.rndsystems.com/pdfs/datasheets/mab3247.pdf, (2015).
Bhat, R. et al., "Astrocyte senescence as a component of Alzheimer's Disease", PLOS One, vol. 7, No. 9, pp. 1-10, (2012).
Flanary, B.E. et al., "Evidence that aging and amyloid promote microglial cell senescence", Rejuvenation Research, vol. 10, No. 1, pp. 61-74, (2007).
Takeda, A. et al., "Advanced glycation end products co-localize with astrocytes and microglial cells in Alzheimer's disease brain", Acta Neuropathologica, vol. 95, pp. 555-558, (1998).
Chinta, S.J. et al., "Environmental stress, ageing and glial cell senescence: a novel mechanistic link to Parkinson's disease?", Journal of Internal Medicine, vol. 273, pp. 429-436, (2013).
Mori, M., "The Parkinsonian Brain: Cellular senescence and neurodegeneration", SAGE, found at sage.buckinstitute.org/the-parkinsonian-brain-cellular-senescence-and-neurodegeneration, (2015).
Das, M.M. et al., "Astrocytes show reduced support of motor neurons with aging that is accelerated in a rodent model of ALS", Neurobiology of Aging, vol. 36, pp. 1130-1139, (2015).
Luessi, F. et al., "Neurodegeneration in multiple sclerosis: novel treatment strategies", Expert Review of Neurotherapeutics, vol. 12, No. 9, pp. 1061-1077, (2012).
Wright, W.E., "Myoblast senescence in Muscular Dystrophy", Experimental Cell Research, vol. 157, pp. 343-354, (1985).
King, O.D., et al., "The tip of the iceberg: RNA-binding proteins with prion-like domains in neurodegenerative disease", Brain Research, vol. 1462, pp. 61-80, (2012).
Dobson, D.M., "The structural basis of protein folding and its links with human disease", Philosophical Transactions of the Royal Society of London B: Biological Sciences, vol. 356, No. 1406, pp. 133-145, (2001).
Kato, S. et al., "Advanced glycation endproduct-modified superoxide dismutase-1 (SOD1)-positive inclusions are common to familial amyotrophic lateral sclerosis patients with SOD1 gene mutations and transgenic mice expressing human SOD1 with a G85R mutation", Acta Neuropathologica, vol. 100, pp. 490-505, (2000).
International Search Report and Written Opinion dated Sep. 29, 2017 for PCT application No. PCT/US2017/027773.
Capparelli, C. et al., "Autophagy and senescence in cancer-associated fibroblasts metabolically supports tumor growth and metastasis via glycolysis and ketone production", Cell Cycle, vol. 11, No. 12, pp. 2285-2302, (2012).
"Shelf life" of blood? Shorter than we think, Johns Hopkins Medicine, pp. 1-2 found at www.hopkinsmedicine.org/news/media/releases/shelf_life_of_blood_shorter_than_we_think, (2013).
Garay-Sevilla, M.E. et al., "Advanced glycosylation end products in skin, serum, saliva and urine and its association with complications of patients with Type 2 diabetes mellitus", Journal of Endocrinological Investigation, vol. 28, No. 5, pp. 223-230, (2005).
Joyal, S.V., "Aging and Glycation", Life Extension Magazine, issue 4, pp. 1-7, found at www.lifeextension.com/Magazine/2008/4/Aging-And-Glycation/p. 01, (2008).
Egberts, J-H. et al., "Anti-tumor necrosis factor therapy inhibits pancreatic tumor growth and metastasis", Cancer Research, vol. 68, pp. 1443-1450, (2008).
Lowe, R. et al., "Buccals are likely to be a more informative surrogate tissue than blood for epigenome-wide association studies", Epigenetics, vol. 8, No. 4, pp. 445-454, (2013).
Bian, C. et al., "Clinical outcome and expression of mutant P53, P16, and Smad4 in lung adenocarcinoma: a prospective study", World Journal of Surgical Oncology, vol. 13, No. 128, pp. 1-8, (2015).
Tape, C.J. et al., "Oncogenic KRAS regulates tumor cell signaling via stromal reciprocation", Cell, vol. 165, pp. 910-920, (2016).
Product description for "CD8+CD57+ T Cell Isolation Kit, human", Miltenyi Biotec, pp. 1-4, found at www.miltenyibiotec.com/en/products-and-services/macs-cell-separation/cell-separation-reagents/t-cells/cd8-cd57-t-cell-isolation-kit-human.aspx, printed on Aug. 16, 2017.
Warrington, K.J. et al., "CD28 loss in senescent CD4+ T cells: reversal by interleukin-12 stimulation", Blood, vol. 101, No. 9, pp. 3543-3549, (2003).
Kared, H. et al., "CD57 in human natural killer cells and T-lymphocytes", Cancer Immunology, Immunotherapy, vol. 65, issue 4, pp. 441-452, (2016).
Li, Z. et al., "Cdkn2a suppresses metastasis in squamous cell carcinomas induced by the gain- of-function mutant p53R172H", The Journal of Pathology, vol. 240, issue 2, pp. 224-234, (2016). (Abstract Only).
Demaria, M. et al., "Cellular senescence promotes adverse effects of chemotherapy and cancer relapse", Cancer Discovery, vol. 7, pp. 165-176, (2017).
Niu, L. et al., "Free and protein-bound Nε-carboxymethyllysine and $N^\epsilon$-carboxyethyllysine in fish muscle: Biological variation and effects of heat treatment", Journal of Food Composition and Analysis, vol. 57, pp. 56-63, (2017).
Yoon, M-S. et al., "Characterisation of advanced glycation endproducts in saliva from patients with diabetes mellitus", Biochemical and Biophysical Research Communications, vol. 323, issue 2, pp. 377-381, (2004).
Product description for "Carboxymethyl Lysine (CML) Elisa", Kamiya Biomedical Company, pp. 1-7, found at www.k-assay.com/pdf/KT-32428.pdf, printed on Aug. 16, 2017.
Baar, M.P. et al., "Targeted apoptosis of senescent cells restores tissue homeostasis in response to chemotoxicity and aging", Cell, vol. 169, pp. 132-147, (2017).
Kim, Y.H. et al., "Senescent tumor cells lead the collective invasion in thyroid cancer", Nature Communications, pp. 1-14, (2017).
Ciccone, T.G. et al., "Reversing OA-new treatment on the horizon", Practical Pain Management, pp. 1-5, found at www.practicalpainmanage-

(56) References Cited

OTHER PUBLICATIONS ment.com/resources/news-and- research/reversing-oa-new-treatment-horizon, printed on Aug. 17, 2017.
Cook, L.S., "Learning about blood component therapy", Nursing, vol. 39, No. 4, pp. 30-33, (2009).
Landesberg, R. et al., "The expression of the receptor for glycation endproducts (RAGE) in oral squamous cell carcinomas", Oral Surgery Oral Medicine Oral Pathology Oral Radiology, vol. 105, issue 5, pp. 617-624, (2008).
Zhou, H.W., "Recovery of function in osteoarthritic chondrocytes induced by p16INK4$^a$-specific siRNA in vitro", Rheumatology, vol. 43, pp. 555-568, (2004).
Fuijkschot, W.W. et al., "Prevention of age-induced N($\epsilon$)-(carboxymethyl)lysine accumulation in the microvasculature", European Journal of Clinical Investigation, vol. 46, issue 4, pp. 334-341, (2016). (Abstract Only).
Rasheed, Z.A. et al., "Pathology of pancreatic stroma in PDAC", Pancreatic Cancer and Tumor Microenvironment, pp. 1-10, (2012).
Morton, J.P. et al., "Mutant p53 drives metastasis and overcomes growth arrest/senescence in pancreatic cancer", PNAS, vol. 107, No. 1, pp. 246-251, (2010).
Verzijl, N. et al., "AGEing and osteoarthritis: a different perspective", Current Opinion in Rheumatology, vol. 15, issue 5, pp. 616-622, (2003).
Frescas, D. et al., "Senescent cells expose and secrete an oxidized form of membrane-bound vimentin as revealed by a natural polyreactive antibody", PNAS, vol. 114, No. 9, pp. E1668- E1677, (2017).
Oren, M. et al., "Mutant p53 gain-of-function in cancer", Cold Spring Harbor Perspectives in Biology, vol. 2, pp. 1-15, (2010).
"Senescence promotes chemotherapy side effects and cancer relapse", Medical Xpress, pp. 1-4, found at https://m.medicalxpress.com/news/2017-01-senescence-chemotherapy-side- effects-cancer.html, (2017).
Oh, J. et al., "Local clearance of senescent cells attenuates the development of post-traumatic osteoarthritis and creates a pro-regenerative environment", Nature Medicine, vol. 23, No. 6, pp. 1-9, (2017).
Protocols for "Isolation of untouched human T cells from peripheral blood mononuclear cells (PBMC)", Thermo Fisher Scientific, pp. 1-4, found at www.thermofisher.com/us/en/home/references/protocols/proteins-expression-isolation-and-human-t-cells-.html, printed on Aug. 17, 2017.
Henrich, C.J. et al., "Isolation and characterization of a glycopeptide from human senescent erythrocytes", Carbohydrate Research, vol. 120, pp. 55-66, (1983).
Tsai, K.K.C. et al., "Low-dose radiation-induced senescent stromal fibroblasts render nearby breast cancer cells radioresistant", Radiation Research, vol. 172, pp. 306-313, (2009).
Nie, H et al., "Impaired glial glutamate uptake induces extrasynaptic glutamate spillover in the spinal sensory synapses of neuropathic rats", Journal of Neurophysiology, vol. 103, pp. 2570-2580, (2010).
Garcia-Matas, S. et al., "Dysfunction of astrocytes in senescence-accelerated mice SAMP8 reduces their neuroprotective capacity", Aging Cell, vol. 7, pp. 630-640, (2008).
Danysz, W. et al., "Alzheimer's disease, B-amyloid, glutamate, NMDA receptors and memantine-searching for the connections", British Journal of Pharmacology, vol. 167, pp. 324-352, (2012).
Blasko, I. et al., "Glial cells: Astrocytes and oligodendrocytes during normal brain aging", Encyclopedia of Neuroscience, pp. 743-747, (2009).
Leonard, B.W. et al., "Subventricular zone neural progenitors from rapid brain autopsies of elderly subjects with and without neurodegenerative disease", The Journal of Comparative Neurology, vol. 515, pp. 269-294, (2009).
Louveau, A. et al., "Structural and functional features of central nervous system lymphatic vessels", Nature, vol. 523, issue 7560, pp. 337-341, (2015).

Torgan, C., "Lymphatic vessels discovered in central nervous system", NIH Research Matters, pp. 1-4, found at www.nih.gov/news-events/nih-research-matters/lymphatic-vessels- discovered-central-nervous-system, Jun. 15, 2015.
Boskovitz, A. et al., "Monoclonal antibodies for brain tumour treatment", Expert Opinion on Biological Therapy, vol. 4, No. 9, pp. 1453-1471, (2004).
Takami, A. et al., "Treatment of primary central nervous system lymphoma with induction of complement-dependent cytotoxicity by intraventricular administration of autologous-serum-supplemented rituximab", Cancer Science, vol. 97, No. 1, pp. 80-83, (2006).
Biran, A et al., "Senescent cells communicate via intercellular protein transfer", Genes & Development, vol. 29, pp. 791-802, (2015).
Golde, T.E. et al., "Proteinopathy-induced neuronal senescence: a hypothesis for brain failure in Alzheimer's and other neurodegenerative diseases", Alzheimer's Research & Therapy, vol. 1, No. 2, pp. 1-12, (2009).
Ouroboros, "Sweet madness: Sporadic prion disease and age-related changes in protein glycosylation", Research in the Biology of Aging, pp. 1-4, found at https://ouroboros.wordpress.com/2006/12/14/sweet-madness-sporadic-prion-disease-and-age- related-changes-in-protein-glycosylation/, (2006).
Xellbiogene, "Amyotrophic lateral sclerosis, immunotherapy is offering some hope", Xellbiogene.com, pp. 1-3, (2014).
Definition of "Complement system" printed from Wikipedia, the free encyclopedia on Aug. 4, 2015 found at http://en.wikipedia.org/wiki/Complement_system.
Definition of "Ventricular system" printed from Wikipedia, the free encyclopedia on Oct. 30, 2017 found at http://en.wikipedia.org/wiki/Ventricular_system.
Urushitani, M., "Future perspectives of immunotherapy against ALS", Rinsho Shinkeigaku, vol. 49, No. 11, pp. 818-820, (2009). (Abstract Only).
Cabezas, I.L. et al., "The role of glial cells in Alzheimer disease: potential therapeutic implications", Neurologia, vol. 29, No. 5, pp. 305-309, (2014).
Definition of "Prion" printed from Wikipedia, the free encyclopedia on Nov. 17, 2015 found at http://en.wikipedia.org/wiki/Prion.
"Prion Diseases", National Institute of Allergy and Infectious Diseases, pp. 1-2, found at www.niaid.nih.gov/diseases-conditions/prion-diseases, printed on Oct. 30, 2017.
"Alzheimer basics: Plaques and tangles", ALZ.org, pp. 1-2, found at. Www.alz.org/norcal/in_my_community 20545.asp, printed on Nov. 17, 2015.
Definition of "Lewy body" printed from Wikipedia, the free encyclopedia on Nov. 17, 2015 found at http://en.wikipedia.org/wiki/Lewy_body.
Definition of "Myocyte" printed from Wikipedia, the free encyclopedia on Nov. 17, 2015 found at http://en.wikipedia.org/wiki/Myocyte.
Definition of "Myosatellite cell" printed from Wikipedia, the free encyclopedia on Nov. 17, 2015 found at http://en.wikipedia.org/wiki/Myosatellite_cell.
Definition of "Microglia" printed from Wikipedia, the free encyclopedia on Oct. 30, 2017 found at http://en.wikipedia.org/wiki/Microglia.
Definition of "Astrocyte" printed from Wikipedia, the free encyclopedia on Oct. 30, 2017 found at http://en.wikipedia.org/wiki/Astrocyte.
Ouroboros, "A role for microglial senescence in Alzheimer's?", Research in the Biology of Aging, pp. 1-3, found at https://ouroboros.wordpress.com/?s=a+role+for+microglial, (2007).
Chen, K.S. et al., "Monoclonal antibody therapy for malignant glioma", Glioma: Immunotherapeutic Approaches, chapter 10, pp. 121-141, (2012).
Reardon, S., "Alzheimer's drug sneaks through blood-brain barrier", Nature News, pp. 1-4, (2014).
"Astrocytes as a novel target in Alzheimer's disease", Expertsvar, pp. 1-2, (2012).
Myslinski, N., "Alzheimer's disease and the blood-brain barrier", Today's Geriatric Medicine, vol. 7, No. 1, pp. 1-10, (2014).

(56) References Cited

OTHER PUBLICATIONS

Hutter-Saunders, J.A.L. et al., "Pathways towards an effective immunotherapy for Parkinson's disease", Expert Reviews in Neurotherapeutics, vol. 11, No. 12, pp. 1703-1715, (2011).
Definition of "Intrathecal administration" printed from Wikipedia, the free encyclopedia on Oct. 30, 2017 found at http://en.wikipedia.org/wiki/Intrathecal_administration.
"What is ALS?", ALSA.org, found at www.alsa.org/2015-non-responsive-pages/about-als/what- is-als.html, printed on Mar. 31, 2016.
Rouger, K. et al., "Systemic delivery of allogenic muscle stem cells induces long-term muscle repair and clinical efficacy in Duchenne muscular dystrophy dogs", The American Journal of Pathology, vol. 179, No. 5, pp. 2501-2518, (2011).
Anderson, J.L. et al., "Brain function in Duchenne muscular dystrophy", Brain, vol. 125, pp. 4-13, (2002).
Jarius, S. et al., "AQP4 antibodies in neuromyelitis optica: diagnostic and pathogenetic relevance", Nature Reviews, vol. 6, pp. 383-392, (2010).
Wesolowski, J. et al., "Single domain antibodies: promising experimental and therapeutic tools in infection and immunity", Medical Microbiology and Immunology, vol. 198, pp. 157-174, (2009).
Definition of "Antibody" printed from Wikipedia, the free encyclopedia on Sep. 21, 2015 found at http://en.wikipedia.org/wiki/Antibody.
Definition of "Antibody-dependent cell-mediated cytotoxicity" printed from Wikipedia, the free encyclopedia on Dec. 28, 2015 found at http://en.wikipedia.org/wiki/Antibody- dependent_cell-mediated_cytotoxicity.
Definition of "Blocking antibody" printed from Wikipedia, the free encyclopedia on Dec. 28, 2015 found at http://en.wikipedia.org/wiki/Blocking_antibody.
Definition of "Fc receptor" printed from Wikipedia, the free encyclopedia on Dec. 28, 2015 found at http://en.wikipedia.org/wiki/Fc_receptor.
Definition of "Fragment crystallizable region" printed from Wikipedia, the free encyclopedia on Dec. 28, 2015 found at http://en.wikipedia.org/wiki/Fragment_crystallizable_region.
Definition of "Neutralizing antibody" printed from Wikipedia, the free encyclopedia on Dec. 28, 2015 found at http://en.wikipedia.org/wiki/Neutralizing_antibody.
Company Information on "NantKwest", pp. 1-4, found at www.nantkwest.com, printed on Apr. 1, 2016.
Forbes, J.M. et al., "Below the radar: Advanced glycation end products that detour "around the side, Clinical Biochemist Reviews, vol. 26, pp. 123-134, (2005).
X419 Paul, W.E., "Fundamental immunology, third edition", Raven Press New York, chapter 9, pp. 292-295, (1993).
Rudikoff, S. et al., "Single amino acid substitution altering antigen-binding specificity", Proceedings of the National Academy of Science USA, vol. 79, pp. 1979-1983, (1982).
Wu, H. et al., "Humanization of a murine monoclonal antibody by simultaneous optimization of framework and CDR residues", Journal of Molecular Biology, vol. 294, pp. 151-162, (1999).
Golay, J. et al., "Mechanism of action of therapeutic monoclonal antibodies: Promises and pitfalls of in vitro and in vivo assays", Archives of Biochemistry and Biophysics, vol. 526, pp. 146-153, (2012).
Tang, S-S. et al., "Reaction of aortic lysyl oxidase with β-Aminopropionitrile", The Journal of Biological Chemistry, vol. 258, No. 7, pp. 4331-4338, (1983).
Saito, H. et al., "Regulation of a novel gene encoding a lysyl oxidase-related protein in cellular adhesion and senescence", The Journal of Biological Chemistry, vol. 272, No. 13, pp. 8157-8160, (1997).
Choi, Y-G. et al., "$N^\varepsilon$-carboxymethyl modification of lysine residues in pathogenic prion isoforms", Molecular Neurobiology, vol. 53, pp. 3102-3112, (2016).
Wendel, U. et al., "A novel monoclonal antibody targeting carboxymethyllysine, an advanced glycation end product in atherosclerosis and pancreatic cancer", PLoS One, vol. 13, No. 2, pp. 1-22, (2018).
Hsia, T-C. et al., "Carboxymethyllysine, an advanced glycation end-product, promotes the invasion and migration of lung cancer A549 cells", Clinical Medicine Research, vol. 6, No. 5, pp. 149-156, (2017).
Nowotny, K. et al., "Advanced glycation end products and oxidative stress in type 2 diabetes mellitus", Biomolecules, vol. 5, pp. 194-222, (2015).
Yun, M.H. et al., "Recurrent turnover of senescent cells during regeneration of a complex structure", eLIFE, elifesciences.org, pp. 1-16, (2015).
Barja, G., "Aging in vertebrates, and the effect of caloric restriction: a mitochondrial free radical production-DNA damage mechanism?", Biological Reviews, vol. 79, No. 2, pp. 235-251, (2004). Abstract Only.
Pamplona, R. et al., "Aging increases nepsilon-(carboxymethyl)lysine and caloric restriction decreases nepsilon-(carboxyethyl)lysine and nepsilon-(malondialdehyde)lysine in rat heart mitochondrial proteins", Free Radical Research, vol. 36, No. 1, pp. 47-54, (2002). Abstract Only.
Yun, M.H., "Cellular senescence in regeneration", The Node, pp. 1-8, found at http://thenode.biologists.com/cellular-senescence-in-regeneration/research/, Jun. 28, 2015.
Kasper, M. et al., "Age-related changes in cells and tissues due to advanced glycation end products (AGEs)", Archives of Gerontology and Geriatrics, vol. 32, issue 3, pp. 233-243, (2001).
Wang, Z. et al., "Advanced glycation end-product Ne-carboxymethyl-Lysine accelerates progression of atherosclerotic calcification in diabetes", Atherosclerosis, vol. 221, issue 2, pp. 387-396, (2012). Abstract Only.
Draber, P. et al., "Stability of monoclonal IgM antibodies freeze-dried in the presence of trehalose", Journal of Immunological Methods, vol. 181, issue 1, pp. 37-43, (1995).
Kesari, S. et al., "Pritumumab binding to glioma cells induces ADCC and inhibits tumor growth", Journal of Clinical Oncology, vol. 35, No. 15 Supplemental, e14004-e14004, (2017). Abstract Only.
Babic, I. et al., "Pritumumab, the first therapeutic antibody for glioma patients", Human Antibodies, vol. 26, No. 2, pp. 95-101, (2017). Abstract Only.
Riva, P. et al., "Treatment of intracranial human glioblastoma by direct intratumoral administration of 131I-labelled anti-tenascin monoclonal antibody BC-2", International Journal of Cancer, vol. 51, No. 1, pp. 7-13, (1992). Abstract Only.
Ruster, M. et al., "Detection of elevated NE-carboxymethyllysine levels in muscular tissue and in serum of patients with fibromyalgia", Scandinavian Journal of Rheumatology, vol. 34, issue 6, pp. 460-463, (2005). Abstract Only.
Niwa, H. et al., "Accelerated formation of $N^\varepsilon$-(carboxymethyl) lysine, an advanced glycation end product, by glyoxal and 3-deoxyglucosone in cultured rat sensory neurons", Biochemical and Biophysical Research Communications, vol. 248, issue 1, pp. 93-97, (1998). Abstract Only.
Daly, C. et al., "Monocyte chemoattractant protein-1 (CCL2) in inflammatory disease and adaptive immunity: Therapeutic opportunities and controversies", Microcirculation, vol. 10, pp. 247-257, (2003).
Lee, S.T. et al., "Decreased number and function of endothelial progenitor cells in patients with migraine", Neurology, vol. 70, No. 17, pp. 1510-1517, (2008). Abstract Only.
Brown, J.N. et al., "Class effect of erythropoietin therapy on hemoglobin Aic in a patient with diabetes mellitus and chronic kidney disease not undergoing hemodialysis", Pharmacotherapy, The Journal of Human Pharmacology and Drug Therapy, vol. 29, No. 4, pp. 468-472, (2009). Abstract Only.
Liu, J. et al., "Accelerated senescence of renal tubular epithelial cells is associated with disease progression of patients with immunoglobulin A (IgA) nephropathy", Translational Research, vol. 159, issue 6, pp. 454-463, (2012). Abstract Only.

(56) References Cited

OTHER PUBLICATIONS

Khaw, K-T. et al., "Association of hemoglobin Ac with cardiovascular disease and mortality in adults: The European prospective investigation into cancer in Norfolk", Annals of Internal Medicine, vol. 141, pp. 413-420, (2004).
Kohnert, K.D. et al., "Destruction of pancreatic beta cells in rats by complete Freund's adjuvant combined with non-diabetogenic doses of streptozotocin", Diabetes Research, vol. 5, No. 1, pp. 1-11, (1987). Abstract Only.
Staud, R., "Fibromyalgia pain: do we know the source?", Current Opinion in Rheumatology, vol. 16, issue 2, pp. 157-163, (2004). Abstract Only.
Fleurence, J. et al., "Targeting and killing glioblastoma with monoclonal antibody to O-acetyl GD2 ganglioside", Oncotarget, vol. 7, No. 27, pp. 41172-41185, (2016).
Velarde, M.C. et al., "Senescent cells and their secretory phenotype as targets for cancer therapy", Interdisciplinary Topics in Gerontology, vol. 38, pp. 17-27, (2013).
Wang, Z. et al., "CML/RAGE signal induces calcification cascade in diabetes", Diabetology & Metabolic Syndrome, vol. 8, No. 83, pp. 1-12, (2016).
Freise, A.C. et al., "In vivo imaging with antibodies and engineered fragments", Molecular Immunology, vol. 67, issue 2, pp. 142-152, (2015).
Pavlides, S. et al., "The reverse Warburg effect: Aerobic glycolysis in cancer associated fibroblasts and the tumor stroma", Cell Cycle, vol. 8, No. 23, pp. 3984-4001, (2009). Dunn, G.P et al., "Principles of immunology and its nuances in the central nervous system", Neuro-Oncology, vol. 17, p. vii3-vii8, (2015).
Rettig, M.P. et al., "Evaluation of biochemical changes during in vivo erythrocyte senescence in the dog", Blood, vol. 93, No. 1, pp. 376-384, (1999).
Baraibar, M.A. et al., "Proteomic quantification and identification of carbonylated proteins upon oxidative stress and during cellular aging", Journal of Proteomics, vol. 92, pp. 63-70, (2013). Abstract Only.
Chaudhuri, J. et al., "A Caenorhabditis elegans model elucidates a conserved role for TRPA1- Nrf signaling in reactive a-dicarbonyl detoxification", Current Biology, vol. 26, pp. 3014-3025, (2016).
Saleh, T. et al., "Reversibility of chemotherapy-induced senescence is independent of autophagy and a potential model for tumor dormancy and cancer recurrence", bioRxiv, pp. 1-29, 5 figures, (2017).
Hubert, P. et al., "Antibody-dependent cell cytotoxicity in monoclonal antibody-mediated tumor immunotherapy", OncoImmunology, vol. 1, issue 1, pp. 103-105, (2012).
Ouchi, R. et al., "Senescence from glioma stem cell differentiation promotes tumor growth", Biochemical and Biophysical Research Communications, vol. 470, No. 2, pp. 275-281, (2016).
Evans, A. et al., "Differentiating benign from malignant solid breast masses: value of shear wave elastography according to lesion stiffness combined with greyscale ultrasound according to BI-RADS classification", British Journal of Cancer, vol. 107, pp. 224-229, (2012).
Walen, K.H., "Normal human cell conversion to 3-D cancer-like growth: Genome damage, endopolyploidy, senescence escape, and cell polarity change/loss", Journal of Cancer Therapy, vol. 2, pp. 181-189, (2011).
Virella, G. et al., "Development of capture assays for different modifications of human low- density lipoprotein", Clinical and Diagnostic Laboratory Immunology, vol. 12, No. 1, pp. 68-75, (2005).
Moghaddam, A.E. et al., "Reactive carbonyls are a major Th2-inducing damage-associated molecular pattern generated by oxidative stress", The Journal of Immunology, vol. 187, pp. 1626-1633, (2011).
Kuilman, T. et al., "The essence of senescence", Genes & Development, vol. 24, pp. 2463-2479, (2010).
James, E.L. et al., "Senescent human fibroblasts show increased glycolysis and redox homeostasis with extracellular metabolomes that overlap with those of irreparable DNA damage, aging, and disease", Journal of Proteome Research, vol. 14, pp. 1854-1871, (2015).
Hein, G. et al., "Are advanced glycation end-product-modified proteins of pathogenetic importance in fibromyalgia?" Rheumatology, vol. 41, pp. 1163-1167, (2002).
Beausejour, C.M. et al., "Reversal of human cellular senescence: roles of the p53 and p16 pathways", The EMBO Journal, vol. 22, No. 16, pp. 4212-4222, (2003).
Simpson, R.J., "Aging, persistent viral infections, and immunosenescence: Can exercise "make space"?", Exercise and Sport Sciences Reviews, vol. 39, No. 1, pp. 23-33, (2011).
Gudkov, A., "Andrei Gudkov taped an expanded presentation of the slides he presented at 2017 Biology of Aging conference at Scripps, Florida, 22-27 January", Everon Biosciences, found at everonbio.com/Andrei-gudkov-taped-an-expanded-presentation-of-the-slides-he-presented-at-2017-biology-of-aging-conference-at-scripps-florida-22-27-january, 2 pages, Mar. 21, 2017. Abstract Only.
Radoi, V. et al., "Advanced glycation end products in diabetes mellitus: Mechanism of action and focused treatment", Proceedings of the Romanian Academy, Series B, vol. 1, pp. 9-19, (2012).
Sieben, C.J. et al., "Two-step senescence-focused cancer therapies", Trends in Cell Biology, pp. 1-15, (2018).
Gaens, K.H.J. et al., "$N^\varepsilon$-(carboxymethyl)lysine-receptor for advanced glycation end product axis is a key modulator of obesity-induced dysregulation of adipokine expression and insulin resistance", Arteriosclerosis, Thrombosis, and Vascular Biology, vol. 34, issue 6, pp. 1199-1208, p. s1-s9, (2014).
Semba, R.D. et al., "Relationship of an advanced glycation end product, plasma carboxymethyl-lysine, with slow walking speed in older adults: the inCHIANTI study", European Journal of Applied Physiology, vol. 108, No. 1, pp. 191-195, (2010).
Wu, J. et al., "Sonoporation, anti-cancer drug and antibody delivery using ultrasound", Ultrasonics, vol. 44, supplement, pp. e21-e25, (2006). Abstract Only.
Meerwaldt, R. et al., "Skin autofluorescence is a strong predictor of cardiac mortality in diabetes", Diabetes Care, vol. 30, No. 1, pp. 107-112, (2007).
Nagai, R. et al., "Antibody-based detection of advanced glycation end-products: promises vs. limitations", Glycoconjugate Journal, vol. 33, No. 4, pp. 545-552, (2016).
Schmidt, A.M. et al., "The biology of the receptor for advanced glycation end products and its ligands", Biochimica et Biophysica Acta, vol. 1498, pp. 99-111, (2000).
Berens, M.E. et al., "". . . those left behind." Biology and oncology of invasive glioma cells", Neoplasia, vol. 1, No. 3, pp. 208-219, (1999).
Hansen, K. et al., "Microneedle enabled intradermal delivery of biologics", 3M Drug Delivery Systems, 1 page, printed on Jul. 25, 2018.
Ikeda, K. et al., "Immunochemical approaches to AGE-structures: characterization of anti-AGE antibodies", Journal of Immunological Methods, vol. 215, No. 1-2, pp. 95-104, (1998).
De Vriese, A.S. et al., "Inhibition of the interaction of AGE-RAGE prevents hyperglycemia- induced fibrosis of the peritoneal membrane", Journal of the American Society of Nephrology, vol. 14, pp. 2109-2118, (2003).
Ott, C. et al., "Role of advanced glycation end products in cellular signaling", Redox Biology, vol. 2, pp. 411-429, (2014).
International Search Report and Written Opinion dated Aug. 7, 2018 for PCT application No. PCT/US2018/027653.
International Search Report and Written Opinion dated Sep. 10, 2018 for PCT application No. PCT/US2018/030931.
Edwards, B.M. et al., "The remarkable flexibility of the human antibody repertoire; Isolation of over one thousand different antibodies to a single protein, BLyS", The Journal of Molecular Biology, vol. 334, pp. 103-118, (2003).
Lloyd, C. et al., "Modelling the human immune response: performance of a 1011 human antibody repertoire against a broad panel of therapeutically relevant antigens", Protein Engineering, Design & Selection, vol. 22, No. 3, pp. 159-168, (2009).

(56) References Cited

OTHER PUBLICATIONS

Ansari, N.A. et al., "Glycated lysine residues: A marker for non-enzymatic protein glycation in age-related diseases", Disease Markers, vol. 30, pp. 317-324, (2011).
Blagosklonny, M.V. et al., "Cancer and aging", Cell Cycle, vol. 7, No. 17, pp. 2615-2618, (2008).
Chow, H-M. et al., "Senescent neurons in the alzheimer's brain kill nearby healthy neurons by blocking their WNT lifeline: The continuing saga of the zombie apocalypse", Alzheimer's & Dementia, vol. 12, No. 7(S), p. P658, (2016).
Dvorakova, E. et al., "Development of monoclonal antibodies specific for glycated prion protein", Journal of Toxicology and Environmental Health, Part A, vol. 74, pp. 1469-1475, (2011).
Search Results for "Carboxy Methyl Lysine Anitbody", 7 pages, antibodies-online.com, (2018).
Awwad, S. et al., "Overview of antibody drug delivery", Pharmaceutics, vol. 10, No. 83, pp. 1-24, (2018).
Farr, J.N. et al., "Targeting cellular senescence prevents age-related bone loss in mice", Nature Medicine, vol. 23, No. 9, pp. 1072-1079, (2017).
Hoenicke, L. et al., "Immune surveillance of senescent cells-biological significance in cancer- and non-cancer pathologies", Carcinogenesis, vol. 33, No. 6, pp. 1123-1126, (2012).
Kemmler, W. et al., "Prevalence of sarcopenia in Germany and the corresponding effect of osteoarthritis in females 70 years and older living in the community: results of the FORMOSA study", Clinical Interventions in Aging, vol. 10, pp. 1565-1573, (2015).
Myrianthopoulos, V. et al., "Senescence and senotherapeutics: a new field in cancer therapy", Pharmacology & Therapeutics, vol. 193, pp. 31-49, (2019).
Salahuddin, P. et al., "The role of advanced glycation end products in various types of neurodegenerative disease: A therapeutic approach", Cellular & Molecular Biology Letters, vol. 19, pp. 407-437, (2014).
Schosserer, M. et al., "The dual role of cellular senescence in developing tumors and their response to cancer therapy", Frontiers in Oncology, vol. 7, article 278, pp. 1-13, (2017).
Bussian, T.J. et al., "Clearance of senescent glial cells prevents tau-dependent pathology and cognitive decline", Nature Letters, vol. 562, pp. 578-582, (2018).
Penney, J. et al., "Senescence mediates neurodegeneration", Nature, vol. 562, pp. 503-504, (2018).
Trivedi, P. M. et al., "Repurposed JAK1/JAK2 inhibitor reverses established autoimmune insulitis in NOD mice", Diabetes, vol. 66, pp. 1650-1660, (2017).
Wang, C. et al., "DNA damage response and cellular senescence in tissues of aging mice", Aging Cell, vol. 8, pp. 311-323, (2009).
Lizuka, K. et al., "Dasatinib improves insulin sensitivity and affects lipid metabolism in a patient with chronic myeloid leukaemia", BMJ Case Rep, pp. 1-3, (2016).
Jeon, O.H. et al., "Local clearance of senescent cells attenuates the development of post- traumatic osteoarthritis and creates a pro-regenerative environment", Nature Medicine, vol. 23, pp. 775-781, (2017). Abstract Only.
Duke Health News & Media, "Duke team finds missing immune cells that could fight lethal brain tumors", Duke University School of Medicine, pp. 1-5, (2018).
Apple, S., "An old idea, revived: Starve cancer to death", NYTimes.com, pp. 1-15, (2016).
Dock, J.N. et al., "Role of CD8 T cell replicative senescence in human aging and in HIV-mediated immunosenescence", Aging and Disease, vol. 2, No. 5, pp. 382-397, (2011).
Rayavarapu, S. et al., "Idiopathic inflammatory myopathies: pathogenic mechanisms of muscle weakness", Skeletal Muscle, vol. 3, No. 13, pp. 1-13, (2013).
Kudryashova, E. et al., "Satellite cell senescence underlies myopathy in a mouse model of limb-girdle muscular dystrophy 2H", The Journal of Clinical Investigation, vol. 122, No. 5, pp. 1764-1776, (2012).

Ratelade, J. et al., "Neuromyelitis optica IgG and natural killer cells produce NMO lesions in mice without myelin loss", Acta Neuropathologica, vol. 123, issue 6, pp. 861-872, (2012).
Vincent, T. et al., "Functional consequences of neuromyelitis optica-IgG astrocyte interactions on blood-brain barrier permeability and granulocyte recruitment", The Journal of Immunology, vol. 181, pp. 5730-5737, (2008).
Baarine, M. et al., "ABCD1 deletion-induced mitochondrial dysfunction is corrected by SAHA: implication for adrenoleukodystrophy", Journal of Neurochemistry, vol. 133, pp. 380-396, (2015).
Durieu, I. et al., "Subepithelial fibrosis and degradation of the bronchial extracellular matrix in cystic fibrosis", American Journal of Respiratory and Critical Care Medicine, vol. 158, No. 2, pp. 580-588, (1998).
Shapiro, B.L. et al., "Premature senescence in cultured skin fibroblasts from subjects with cystic fibrosis", Science, vol. 203, issue 4386, pp. 1251-1253, (1979). Abstract Only.
Fischer, B.M. et al., "Increased expression of senescence markers in cystic fibrosis airways", American Journal of Physiology Lung Cellular and Molecular Physiology, vol. 304, No. 6, pp. L394-L400, (2013).
Thom, M. et al., "An investigation of the expression of G1-phase cell cycle proteins in focal cortical dysplasia type IIB", Journal of Neuropathology and Experimental Neurology, vol. 66, No. 11, pp. 1045-1055, (2007).
Valdivieso, A.G. et al., "CFTR activity and mitochondrial function", Redox Biology, vol. 1, pp. 190-202, (2013).
Chilosi, M. et al., "Premature lung aging and cellular senescence in the pathogenesis of idiopathic pulmonary fibrosis and COPD/emphysema", Translational Research, vol. 162, issue 3, pp. 156-173, (2013). Abstract Only.
Ribeiro, C.M.P., "The role of intracellular calcium signals in inflammatory responses of polarized cystic fibrosis human airway epithelia", Drugs in R&D, vol. 7, issue 1, pp. 17-31, (2006). Abstract Only.
Velisek L. et al., "Aging: effects of aging on seizures and epilepsy", Encyclopedia of Basic Epilepsy Research, pp. 37-40, (2009). Abstract Only.
Muller, S. et al., "Analysis of senescence markers in rodent pancreatic stellate cells", The Pancreapedia, pp. 1-8, (2013).
Lim, M., "Acute immunology, temporal lobe epilepsy and other disorders", YoungEpilepsy.Org, pp. 1-70, found at http://youngepilepsy.org.uk/dmdocuments/MIND-THE- GAP2015_Ming%20Lim.pdf, (2015).
Definition of "Cachexia" printed from Wikipedia, the free encyclopedia on Dec. 28, 2015 found at http://en.wikipedia.org/wiki/Cachexia.
Lok, C., "The last illness, researchers are gaining insight into the causes of Cachexia-a devastating form of muscle wasting that is often the final stage of cancer and other diseases", Nature, vol. 528, pp. 182-183, (2015).
da Rocha, O.M. et al., "Sarcopenia in rheumatoid cachexia: definition, mechanisms, clinical consequences and potential therapies", Revista Brasileira de Reumatologia, vol. 49, No. 3, pp. 294-301, (2009).
Tisdale, M.J., "Biology of Cachexia", Journal of the National Cancer Institute, vol. 89, No. 23, pp. 1763-1773, (1997).
Romanick, M. et al., "Murine models of atrophy, cachexia, and sarcopenia in skeletal muscle", Biochimica et Biophysica Acta—Molecular Basis of Disease, vol. 1832, issue 9, pp. 1410-1420, (2013).
Ali, S. et al., "Sarcopenia, cachexia and aging: Diagnosis, mechanisms and therapeutic options", Gerontology, vol. 60, No. 4, pp. 294-305, (2014).
Angelini, P. D. et al., "Constitutive HER2 signaling promotes breast cancer metastasis through cellular senescence", Cancer Research, vol. 73, No. 1, pp. 450-458, (2013).
Arai, Y. et al., "Inflammation, but not telomere length, predicts successful ageing at extreme old age: A longitudinal study of semi-supercentenarians", EBioMedicine, vol. 2, pp. 1549-1558, (2015).

(56) References Cited

OTHER PUBLICATIONS

Bedard, N. et al., "Inactivation of the ubiquitin-specific protease 19 deubiquitinating enzyme protects against muscle wasting", The FASEB Journal, vol. 29, No. 9, pp. 3889-3898, (2016).
Figueroa-Clarevega, A. et al., "Malignant drosophila tumors interrupt insulin signaling to induce cachexia-like wasting", Developmental Cell, vol. 33, pp. 47-55, (2015).
Giacconi, R. et al., "Cellular senescence and inflammatory burden as determinants of mortality in elderly people until the extreme old age", EBioMedicine, vol. 2, pp. 1316-1317, (2015).
Jin, H. et al., "Protein modifications as potential biomarkers in breast cancer", Biomarker Insights, vol. 4, pp. 191-200, (2009).
Lee, S-J. et al., "Treating cancer cachexia to treat cancer", Skeletal Muscle, vol. 1, No. 2, pp. 1-5, (2011).
Mohamed, M.M. et al., "Human monocytes augment invasiveness and proteolytic activity of inflammatory breast cancer", Biological Chemistry, vol. 389, No. 8, pp. 1117-1121, (2008).
Pare, R. et al., "The significance of the senescence pathway in breast cancer progression", Journal of Clinical Pathology, vol. 66, pp. 491-495, (2013). Abstract Only.
Pinto, N.I. et al., "Cancer as a proinflammatory environment: Metastasis and cachexia", Mediators of Inflammation, vol. 2015, pp. 1-13, (2015).
Tesarova, P. et al., "Carbonyl and oxidative stress in patients with breast cancer—is there a relation to the stage of the disease?", Neoplasma, vol. 54, No. 3, pp. 219-224, (2007).
Tseng, Y-C., et al., "Preclinical investigation of the novel histone deacetylase inhibitor AR-42 in the treatment of cancer-induced cachexia", Journal of the National Cancer Institute, vol. 107, No. 12, pp. 1-14, (2015).
Wang, S. et al., "Characterization of IGFBP-3, PAI-1 and SPARC mRNA expression in senescent fibroblasts", Mechanisms of Ageing and Development, vol. 92, issues 2-3, pp. 121-132, (1996). Abstract Only.
Yang, S. et al., "Impact of oxidative stress biomarkers and carboxymethyllysine (an advanced glycation end product) on prostate cancer: A prospective study", Clinical Genitourinary Cancer, vol. 13, issue 5, pp. e347-e351, (2015).
"Global Arthritis Research Network: 4th World Congress on Arthritis in Montreal", Arthritis Research & Therapy, vol. 6, supplement 3, meeting abstracts, pp. S1-S41, September 20-22, (2004).
Miller, R.E. et al., "Osteoarthritis joint pain: The cytokine connection", Cytokine, vol. 70, No. 2, pp. 185-193, (2014).
Lifeextension, "Chronic Pain", Lifeextension.com, pp. 1-18, found at www.lifeextension.com/protocols/health-concerns/chronic-pain/ p. 03, (2016).
Rush University Medical Center, "Scientists home in on cause of osteoarthritis pain". Science Daily, found at www.sciencedaily.com/releases/2012/12/121227173053.htm, pp. 1-4, (2012).
Kidd, B.L. et al., "Mechanisms of inflammatory pain", British Journal of Anesthesia, vol. 87, No. 1, pp. 3-11, (2001).
Price, U.S et al., "The role of chondrocyte senescence in osteoarthritis", Aging Cell, vol. 1, pp. 57-65, (2002).
Morales, T.I., "Chondrocyte moves: clever strategies?", OsteoArthritis and Cartilage, vol. 15, pp. 861-871, (2007).
Martin, J.A. et al., "Effects of oxidative damage and telomerase activity on human articular cartilage chondrocyte senescence", Journal of Gerontology: Biological Sciences, vol. 59A, No. 4, pp. 324-337, (2004).
Ang, D.C. et al., "MCP-1 and IL-8 as pain biomarkers in fibromyalgia: A pilot study", Pain Medicine, vol. 12, pp. 1154-1161, (2011).
Burton, D.G.A. et al., "Microarray analysis of senescent vascular smooth muscle cells: A link to atherosclerosis and vascular calcification", Experimental Gerontology, vol. 44, issue 10, pp. 659-665, (2009).
Konttinen, Y.T. et al., "Chondrocyte-mediated collagenolysis correlates with cartilage destruction grades in osteoarthritis", Clinical and Experimental Rheumatology, vol. 23, pp. 19-26, (2005).
"Low back pain", U.S. Department of Health and Human Services, Public Health Service National Institutes of Health, 1-28, (2014).
Bicer, F. "CCL2 (MCP-1) mediates chronic pelvic pain through mast cells in experimental autoimmune cystitis", ETD Archive, pp. 1-120, (2012).
Loeser, R.F. "Aging and osteoarthritis: The role of chondrocyte senescence and aging changes in the cartilage matrix", Osteoarthritis and Cartilage, vol. 17, No. 8, pp. 971-979, (2009).
Zhou, H-W. et al., "Expressions of p16INK4a in healthy and osteoarthritic human articular cartilage and difference analysis", Research Gate, pp. 2148-2149, found at www.researchgate.net/publication/290275008_Expressions_of_p16INK4a_in_healthy_and_ost eoarthritic_human_articular_cartilage_and_difference_analysis, (2004). Abstract Only.
Martin, J.A. et al., "Post-traumatic osteoarthritis: the role of accelerated chondrocyte senescence", Biorheology, vol. 41, pp. 479-491, (2004).
Martin, J.A. et al., "Human chondrocyte senescence and osteoarthritis", Biorheology, vol. 39, No. 1,2, pp. 145-152, (2002). Abstract Only.
Forliti, M., "Mayo clinic researchers link senescent cells to most common form of arthritis", Mayo Clinic, pp. 1-2, found at www.eurekalert.org/pub_releases/2016-08/mc-mcr081016.php, (2016).
Roubenoff, R., "Sarcopenic obesity: Does muscle loss cause fat gain? Lessons from Rheumatoid arthritis and osteoarthritis", Annals of the New York Academy of Sciences, vol. 904, pp. 553-557, (2000). Abstract Only.
De Ceuninck, F. et al., "Bearing arms against osteoarthritis and sarcopenia: When cartilage and skeletal muscle find common interest in talking together", Drug Discovery Today, vol. 19, issue 3, pp. 305-311, (2014). Abstract Only.
Chatterjea, D. "Mast cells and pain", Mastcell Basophil, pp. 1-5, found at www.mastcell-basophil.net/wiki/wiki-start/mast-cells-and-pain/, (2013).
Bach, B. "New drug promises relief for inflammatory pain, scientists say", News Center, Stanford Medicine PASIN, found at med.stanford.edu/news/all-news/2014/08/new-drug-promises-relief-for-inflammatory-pain-scientists-say.html, 3 pages, (2014).
Daly, C. et al., "Monocyte chemoattractant protein-1 (CCL2) in inflammatory disease and adaptive immunity: Therapeutic opportunities and controversies", Microcirculation, vol. 10, issue 3-4, pp. 247-257, (2003).
"MMP13 gene", Nih U.S. National Library of Medicine, found at ghr.nlm.nih.gov/gene/MMP13, 4 pages, (2016).
Hayami, T. et al., "MMP-1 (Collagenase-1) and MMP-13 (Collagenase-3) differentially regulate markers of osteoblastic differentiation in osteogenic cells", Matrix Biology, vol. 27, issue 8, pp. 682-692, (2008).
Attur, M.G. et al., "Autocrine production of IL-1 beta by human osteoarthritis-affected cartilage and differential regulation of endogenous nitric oxide, IL-6, prostaglandin E2, and IL-8", Proceedings of the Association of American Physicians, vol. 110, No. 1, pp. 65-72, (1998). Abstract Only.
Xu, Y-K. et al., "The role of MCP-1-CCR2 ligand-receptor axis in chondrocyte degradation and disease progress in knee osteoarthritis", Biological Research, vol. 48, No. 64, pp. 1-8, (2015).
Goldring, M.B., "The role of the chondrocyte in osteoarthritis", Arthritis & Rheumatism, vol. 43, No. 9, pp. 1916-1926, (2000).
Mobasheri, A. et al., "Chondrocyte and mesenchymal stem cell-based therapies for cartilage repair in osteoarthritis and related orthopaedic conditions", Maturitas, vol. 78, pp. 188-198, (2014).
"What are chondrocytes?", wiseGeek, found at www.wisegeek.org/what-are-chondrocytes.htm, 1 page, printed on Nov. 29, 2016.
Woolf, A.D. et al., "Burden of major musculoskeletal conditions", Bulletin of the World Health Organization, vol. 81, No. 9, pp. 646-656, (2003).
Pereira, D. et al., "The effect of osteoarthritis definition on prevalence and incidence estimates: a systematic review", Osteoarthritis and Cartilage, vol. 19, pp. 1270-1285, (2011).
Martin, J.A. et al., "Aging, articular cartilage chondrocyte senescence and osteoarthritis", Biogerontology, vol. 3, pp. 257-264, (2002).
"What is osteoarthritis?", NIH National Institute of Arthritis and Musculoskeletal and Skin Diseases, pp. 1-4, (2014).

(56) References Cited

OTHER PUBLICATIONS

Definition of "Osteoarthritis" printed from Wikipedia, the free encyclopedia, found at en.wikipedia.org/wiki/Osteoarthritis, Dec. 13, 2016.
"At a glance 2016, Arthritis, Improving the quality of life for people with arthritis", National Center for Chronic Disease Prevention and Health Promotion, pp. 1-4, (2016).
"IASP Taxonomy", International Association for the Study of Pain, found at www.iasp- pain.org/Taxonomy, pp. 1-9, (2014).
"Pain: Hope through research", National Institute of Neurological Disorders and Stroke, National Institutes of Health, pp. 1-46, (2014).
Definition of "Allodynia" printed from Wikipedia, the free encyclopedia, found at en.wikipedia.org/wiki/Allodynia, Dec. 13, 2016.
Quadros, A.U. et al., "Dynamic weight bearing is an efficient and predictable method for evaluation of arthritic nociception and its pathophysiological mechanisms in mice", Nature, Scientific Reports, pp. 1-11, (2015).
Leung, L. et al., "TNF-α and neuropathic pain - a review", Journal of Neuroinflammation, vol. 7, No. 27, pp. 1-11, (2010).
Schafers, M. et al., "Tumor necrosis factor-a induces mechanical allodynia after spinal nerve ligation by activation of p38 MAPK in primary sensory neurons", The Journal of Neuroscience, vol. 23, No. 7, pp. 2517-2521, (2003).
Sun, J.L. et al., "CX3CL1/CX3CR1 regulates nerve injury-induced pain hypersensitivity through the ERK5 signaling pathway", Journal of Neuroscience Research, vol. 91, No. 4, pp. 545-553, (2013). Abstract Only.
American Diabetes Association, "Diagnosis and classification of diabetes mellitus", Diabetes Care, vol. 31, supp. 1, pp. S55-S60, (2008).
Watkins, L.R. et al., "Mechanisms of tumor necrosis factor-a (TNF-α) hyperalgesia", Brain Research, vol. 692, issues 1-2, pp. 244-250, (1995). Abstract Only.
"Global report on diabetes", World Health Organization, pp. 1-88, (2016).
"National diabetes statistics report, 2017: Estimates of diabetes and its burden in the United States", U.S. Department of Health and Human Services, Centers for Disease Control and Prevention, pp. 1-20, (2017).
O'Brien, P.D. et al., "Mouse models of diabetic neuropathy", Institute for Laboratory Animal Research Journal, vol. 54, No. 3, pp. 259-272, (2014).
O'Brien, P.D. et al., "BTBR ob/ob mice as a novel diabetic neuropathy model: Neurological characterization and gene expression analyses", Neurobiology of Disease, vol. 73, pp. 348-355, (2015).
Alpers, C.E. et al., "Mouse models of diabetic nephropathy", Current Opinion in Nephrology and Hypertension, vol. 20, No. 3, pp. 278-284, (2011).
Hudkins, K.L. et al., "BTBR ob/ob mutant mice model progressive diabetic nephropathy", Journal of the American Society of Nephrology, vol. 21, pp. 1533-1542, (2010).
O'Brien, K.D et al., "Divergent effects of vasodilators on cardiac hypertrophy and inflammation in a murine model of diabetic cardiomyopathy", Journal of the American College of Cardiology, vol. 57, issue 17, p. e193, (2011). Abstract Only.
Lee, J-T. et al., "Macrophage metalloelastase (MMP12) regulates adipose tissue expansion, insulin sensitivity, and expression of inducible nitric oxide synthase", Endocrinology, vol. 155, No. 9, pp. 3409-3420, (2014).
Xu, X. et al., "A glimpse of matrix metalloproteinases in diabetic nephropathy", Current Medicinal Chemistry, vol. 21, No. 28, pp. 3244-3260, (2014).
Tsioufis, C. et al., "The role of matrix metalloproteinases in diabetes mellitus", Current Topics in Medicinal Chemistry, vol. 12, No. 10, pp. 1159-1165, (2012). Abstract Only.

Pechhold, K. et al., "Blood glucose levels regulate pancreatic β-cell proliferation during experimentally-induced and spontaneous autoimmune diabetes in mice", PLOS One, vol. 4, No. 3, pp. e4827, (2009).
Oh, K.-J. et al., "Metabolic adaptation in obesity and type II diabetes: myokines, adipokines and hepatokines", International Journal of Molecular Sciences, vol. 18, No. 1, article 8, pp. 1-31, (2017).
Micov, A. et al., "Levetiracetam synergises with common analgesics in producing antinociception in a mouse model of painful diabetic neuropathy", Pharmacological Research, vol. 97, pp. 131-142, (2015). Abstract Only.
Feldman, E., "Tail flick assay", Animal Models of Diabetic Complications Consortium, pp. 1-3, (2004).
Bratwur, W., "Abt 263 was formulated in 10 ethano", found at www.selleckchem.com/blog/ABT-263-was-formulated-in-10-ethano. html, (2013). Abstract Only "Beta cell dysfunction", Diabetes and the Environment, found at www.diabetesandenvironment.org/home/mech/betacells, pp. 1-7, printed on Feb. 27, 2019.
Edelman, D., "Understanding beta cell exhaustion in Type 2 diabetics", Diabetes Daily, found at www.diabetesdaily.com/blog/2008/06/podcast-understanding-beta-cell-exhaustion-in-type-2- diabetics, pp. 1-6, (2008).
Cao, Y. et al., "Mechanisms of endothelial to mesenchymal transition in the retina in diabetes", Investigative Ophthalmology & Visual Science, vol. 55, pp. 7321-7331, (2014).
Palmer, A.K. et al., "Cellular senescence in Type 2 diabetes: a therapeutic opportunity", Diabetes, vol. 64, pp. 2289-2298, (2015).
Cummings, B.P. et al., "Maternal ileal interposition surgery confers metabolic improvements to offspring independent of effects on maternal body weight in UCD-T2DM rats", Obesity Surgery, vol. 23, No. 12, pp. 2042-2049, (2013).
Cummings, B.P. et al., "Development and characterization of a novel rat model of type 2 diabetes mellitus: the UC Davis type 2 diabetes mellitus UCD-T2DM rat", American Journal of Physiology Regulatory, Integrative and Comparative Physiology, vol. 295, pp. R1782-R1793, (2008).
Cummings, B.P. et al., "Bile-acid-mediated decrease in endoplasmic reticulum stress: a potential contributor to the metabolic benefits of ileal interposition surgery in UCD-T2DM rats", Disease Models & Mechanisms, vol. 6, No. 2, pp. 443-456, (2013).
Cummings, B.P. et al., "Vertical sleeve gastrectomy improves glucose and lipid metabolism and delays diabetes onset in the UCD-T2DM rats", Endocrinology, vol. 153, No. 8, pp. 3620-3632, (2012).
Cummings, B.P. et al., "Ileal interposition surgery improves glucose and lipid metabolism and delays diabetes onset in the UCD-T2DM rat", Gastroenterology, vol. 138, pp. 2437-2446, (2010).
American Diabetes Association, "Standards of medical care in diabetes—2016 abridged for primary care providers", Diabetes, vol. 34, No. 1, pp. 3-21, (2016).
Definition of "Methylglyoxal" printed from Wikipedia, the free encyclopedia, found at en.wikipedia.org/wiki/Methylglyoxal, Jun. 5, 2017.
Boesten, D.M.P.H.J. et al., "Effect of Na-carboxymethyllysine on oxidative stress and the glutathione system in beta cells", Toxicology Reports, vol. 1, pp. 973-980, (2014).
Molla, B. et al., "Two different pathogenic mechanisms, dying-back axonal neuropathy and pancreatic senescence, are present in the YG8R mouse model of Friedreich ataxia", Disease Models & Mechanisms, vol. 9, pp. 647-657, (2016).
Kender, Z. et al., "Effect of metformin on methylglyoxal metabolism in patients with type 2 diabetes", Experimental and Clinical Endocrinology & Diabetes, vol. 122, No. 5, pp. 316-319, (2014). Abstract Only.
Ehrenmann, F. et al., "IMGT/3Dstructure-DB and IMGT/DomainGapAlign: a database and a tool for immunoglobulins or antibodies, T cell receptors, MHC, IgSF and MhcSF", Nucleic Acids Research, vol. 38, pp. D301-D307, (2010).
Glover, A., "Of mice and men", European Biophamaceutical Review, pp. 30-34, (2016).

(56) References Cited

OTHER PUBLICATIONS

"The basic guide to magnetic bead cell separation", Sepmag.eu, pp. 1-15, found at www.sepmag.eu/free-basic-guide-magnetic-bead-cell-separation, (2017).
Su, W-S. et al., "Controllable permeability of blood-brain barrier and reduced brain injury through low-intensity pulsed ultrasound stimulation", Oncotarget, vol. 6, No. 39, p. 42290- 42299, (2015).
Haslbeck, K.M. et al., "The RAGE pathway in inflammatory myopathies and limb girdle muscular dystrophy", Acta Neuropathologica, vol. 110, issue 3, pp. 247-254, (2005).
Sternberg, Z. et al., "AGE-RAGE in multiple sclerosis brain", Immunological Investigations, vol. 40, issue 2, pp. 197-205, (2011). Abstract Only.
Miyata, T. et al., "Increased pentosidine, an advanced glycation end product, in plasma and synovial fluid from patients with rheumatoid arthritis and its relation with inflammatory markers", Biochemical and Biophysical Research Communications, vol. 244, pp. 45-49, (1998).
Mulrennan, S. et al., "The role of receptor for advanced glycation end products in airway inflammation in CF and CF related diabetes", Scientific Reports, vol. 5, No. 8931, pp. 1-9, (2015).
Weber, K. et al., "Distribution of advanced glycation end products in the cerebellar neurons of dogs", Brain Research, vol. 791, pp. 11-17, (1998).
Berg, T.J. et al., "The advanced glycation end product $N^{\alpha}$-(carboxymethyl)lysine is increased in serum from children and adolescents with type 1 diabetes", Diabetes Care, vol. 21, No. 11, pp. 1997-2002, (1998).
Degenhardt, T.P. et al., "The serum concentration of the advanced glycation end-product $N^{\epsilon}$- (carboxymethyl)lysine is increased in uremia", Kidney International, vol. 52, pp. 1064-1067, (1997).
Hayase, F. et al., "Aging of proteins: Immunological detection of a glucose-derived pyrrole formed during maillard reaction in vivo", The Journal of Biological Chemistry, vol. 263, No. 7, pp. 3758-3764, (1989).
Ikeda, K. et al., "Immunochemical approaches to AGE-structures: characterization of anti-AGE antibodies", The Maillard Reaction in Foods and Medicine, pp. 310-315, (1998).
Kume, S. et al., "Immunohistochemical and ultrastructural detection of advanced glycation end products in atherosclerotic lesions of human aorta with a novel specific monoclonal antibody", American Journal of Pathology, vol. 147, No. 3, pp. 654-667, (1995).
Makita, A. et al., "Immunochemical detection of advanced glycosylation end products in vivo", The Journal of Biological Chemistry, vol. 267, No. 8, pp. 5133-5138, (1992).
Niwa, T. et al., "Immunohistochemical detection of advanced glycation end products in dialysis- related amyloidosis", Kidney International, vol. 48, pp. 771-778, (1995).
Papanastasiou, P. et al., "Immunological quantification of advanced glycosylation end-products in the serum of patients on hemodialysis of CAPD", Kidney International, vol. 46, pp. 216-222, (1994).
Schleicher, E.D. et al., "Increased accumulation of the glycoxidation product N(epsilon)- (carboxymethyl)lysine in human tissues in diabetes and aging", The Journal of Clinical Investigation, vol. 99, No. 3, pp. 457-468, (1997).
Takeuchi, M. et al., "Immunological detection of a novel advanced glycation end-product", Molecular Medicine, vol. 7, No. 11, pp. 783-791, (2001).
Kobayashi, S. et al., "$N^{\epsilon}$-(Carboxymethyl)lysine-induced choroidal angiogenic potential facilitates retinal neovascularization in advanced-diabetic rat in vitro", The Open Pharmacology Journal vol. 2, pp. 79-85, (2008).
Tamemoto, H. et al., "AGE inhibitor-recent development", Diabetes Frontier, vol. 16, No. 5, pp. 541-546, (2005).
Nagai, R. et al., "Prevention of diabetic complication by AGE inhibitors", Progress of Medicine, vol. 207, No. 9, pp. 663-667, (2003).
Vistoli, G. et al., "Advanced glycoxidation and lipoxidation end products (AGEs and ALEs): an overview of their mechanisms of formation", Free Radical Research, vol. 47, supple. 1, pp. 3-27, (2013).
Bachmeier, B.E. et al., "Maillard products as biomarkers in cancer", Annals of the New York Academy of Sciences, vol. 1126, No. 1, pp. 283-287, (2008). Abstract Only.
Chen, Z. et al., "Senescent cells re-engineered to express soluble programmed death receptor- 1 for inhibiting programmed death receptor-1/programmed death ligand-1 as a vaccination approach against breast cancer", Cancer Science, vol. 109, pp. 1753-1763, (2018).
Leontieva, O.V. et al., "Yeast-like chronological senescence in mammalian cells: phenomenon, mechanism and pharmacological suppression", Aging, vol. 3, No. 11, pp. 1-14, (2011).
Moser, A.C. et al., "Immunoaffinity chromatography: an introduction to applications and recent developments", Bioanalysis, vol. 2, No. 4, pp. 769-790, (2010).
Prosser, C.G. et al., "$N^{\epsilon}$-carboxymethyllysine in nutritional milk formulas for infants", Food Chemistry, vol. 274, pp. 886-890, (2019).
Takeuchi, M. et al., "Detection of noncarboxymethyllysine and carboxymethyllysine advanced glycation end products (AGE) in serum of diabetic patients", Molecular Medicine, vol. 5, pp. 393-405, (1999).
Teodorowicz, M. et al., Immunomodulation by processed animal feed: The role of maillard reaction products and advanced glycation end-products (AGEs), Frontiers in Immunology, vol. 9, article 2088, pp. 1-15, (2018).
Kwak, T. et al., "Targeting of RAGE-ligand signaling impairs breast cancer cell invasion and metastasis", Oncogene, vol. 11, pp. 1559-1572, (2017). Abstract Only.
Inui, H. et al., "A scFv antibody-based immunoaffinity chromatography column for clean-up of bisphenol a-contaminated water samples", Journal of Agricultural and Food Chemistry, vol. 57, No. 2, pp. 353-358, (2009). Abstract Only.
Casset, F. et al., "A peptide mimetic of an anti-CD4 monoclonal antibody by rational design", Biochemical and Biophysical Research Communications, vol. 307, pp. 198-205, (2003).
Chikazawa, M. et al., "Multispecificity of immunoglobulin M antibodies raised against advanced glycation end products", The Journal of Biological Chemistry, vol. 288, No. 19, p. 13204- 13214, (2013).
De Pascalis, R. et al., "Grafting of "abbreviated" complementarity-determining regions containing specificity-determining residues essential for ligand contact to engineer a less immunogenic humanized monoclonal antibody", The Journal of Immunology, vol. 169, pp. 3076-3084, (2002).
Hirose, J. et al., "Immunohistochemical distribution of advanced glycation end products (AFEs) in human osteoarthritic cartilage", Acta Histochemica, vol. 113, No. 6, pp. 613-618, (2011).
Kumar, S. et al., "Molecular cloning and expression of the fabs of human autoantibodies in escherichia coli", The Journal of Biological Chemistry, vol. 275, No. 45, p. 35129-35136, (2000).
Lamminmaki, U. et al., "Crystal structure of a recombinant anti-estradiol fab fragment in complex with 17B-estradiol", The Journal of Biological Chemistry, vol. 276, No. 39, p. 36687- 36694, (2001).
Padlan, E.A. et al., "Structure of an antibody-antigen complex: Crystal structure of the hyhel-10 fab-lysozyme complex", Proceedings of the National Academy of Science, fol. 86, pp. 5938-5942, (1989).
Schwab, W. et al., "Immunohistochemical demonstration of $N^{\epsilon}$-(carboxymethyl)lysine protein adducts in normal and osteoarthritic cartilage", Histochemistry and Cell Biology, vol. 117, issue 6, pp. 541-546, (2002).
Smith-Gill, S.J. et al., "Contributions of immunoglobulin heavy and light chains to antibody specificity for lysozyme and two haptens" The Journal of Immunology, vol. 139, No. 12, pp. 4135-4144, (1987).
Song, M-K, et al., "Light chain of natural antibody plays a dominant role in protein antigen binding", Biochemical and Biophysical Research Communications, vol. 268, pp. 390-394, (2000).

(56) References Cited

OTHER PUBLICATIONS

Ward, E.S. et al., "Binding activities of a repertoire of single immunoglobulin variable domains secreted from *escherichia coli*", Nature, vol. 341, pp. 544-546, (1989).
Jeon O.H. et al., "Senescent cells and osteoarthritis: a painful connection", The Journal of Clinical Investigation, vol. 128, No. 4, pp. 1229-1237, (2018).
Guan, Z. et al., "Contemporary views on inflammatory pain mechanisms: TRPing over innate and microglial pathways", F1000Research, vol. 5, pp. 1-11, (2016).
Musi, N. et al., "Tau protein aggregation is associated with cellular senescence in the brain", Aging Cell, vol. 17, pp. 1-13, (2018).
International Search Report and Written Opinion dated Nov. 25, 2019 for PCT application No. PCT/US2019/047762.
Dillon, P., "Focused ultrasound and pembrolizumab in metastatic breast cancer (breast-48)", ClinicalTrials.gov, pp. 1-7. (2017).
Masui, T. et al., "Low-intensity ultrasound enhances the anticancer activity of cetuximab in human head and neck cancer cells", Experimental and Therapeutic Medicine, vol. 5, pp. 11-16, (2013).
Khaibullina, A. et al., "Pulsed high-intensity focused ultrasound enhances uptake of radiolabeled monoclonal antibody to human epidermoid tumor in nude mice", The Journal of Nuclear Medicine, vol. 49, pp. 295-302, (2008).
Liao, A-H. et al., "Enhanced therapeutic epidermal growth factor receptor (EGFR) antibody delivery via pulsed ultrasound with targeting microbubbles for glioma treatment", Journal of Medical and Biological Engineering, vol. 35, pp. 156-164, (2015).
Liu, H-L. et al., "Focused ultrasound enhances central nervous system delivery of bevacizumab for malignant glioma treatment", Radiology, vol. 281, No. 1, pp. 99-108, (2016).
Kobus, T. et al., "Growth inhibition in a brain metastasis model by antibody delivery using focused ultrasound-mediated blood-brain barrier disruption", Journal of Controlled Release, vol. 238, pp. 281-288, (2016).
Linetsky, M. et al., "UVA light-excited kynurenines oxidize ascorbate and modify lens proteins through the formation of advanced glycation end products, Implications for Human Lens Aging and Cataract Formation", Journal of Biological Chemistry, vol. 289, No. 24, p. 17111-17123, (2014).
Chaudhary, M.K. et al., "Redox imbalance in a model of rat mimicking Hutchinson-Gilford progeria syndrome", Biochemical and Biophysical Research Communications, vol. 491, No. 2, pp. 361-367, (2017). Abstract Only.
Hause F. et al., "Accumulation of glycated proteins suggesting premature ageing in lamin B receptor deficient mice", Biogerontology, vol. 19, no. 1, pp. 95-100, (2017). Abstract Only.
International Search Report and Written Opinion dated Nov. 27, 2019 for PCT application No. PCT/US2019/043071.
Zhang, J-M. et al., "Cytokines, Inflammation and Pain", International Anesthesiology Clinics, vol. 45, No. 2, pp. 27-37, (2007).
Bhatt A.N. et al., "Transient elevation of glycolysis confers radioresistance by facilitating DNA repair in cells", BMC Cancer, vol. 15, Article 335, pp. 1-12, (2015).
Callier, V., "Cancer cells can't proliferate and invade at the same time", Scientific American, pp. 1-5, (2016), found at www.scientificamerican.com/article/cancer-cells-can-t-proliferate-and-invade-at-the-same-time.
Drews, G. et al., "Oxidative stress and beta-cell dysfunction", European Journal of Physiology, vol. 460, pp. 703-718, (2010).
Huang, C-C. et al., "Glycolytic inhibitor 2-deoxyglucose simultaneously targets cancer and endothelial cells to suppress neuroblastoma growth in mice", Disease Models and Mechanisms, vol. 8, pp. 1247-1254, (2015).
Kehm, R. et al., "age-related oxidative changes in pancreatic islets are predominantly located in the vascular system", Redox Biology, vol. 15, pp. 387-393, (2018).
Kohrman, A.Q. et al., "Divide or conquer: Cell cycle regulation of invasive behavior", Trends in Cell Biology, vol. 27, issue 1, pp. 12-25, (2017).

Menini, S. et al., "The advanced glycation end-product $N^\epsilon$-carboxymethyllysine promotes progression of pancreatic cancer: implications for diabetes-associated risk and its prevention", Journal of Pathology, vol. 245, pp. 197-208, (2018).
Wang, J. et al., "Oxidative stress in pancreatic beta cell regeneration", Oxidative Medicine and Cellular Longevity, vol. 2017, Article id 1930261, pp. 1-9, (2017).
Nerlich, A.G. et al., "$N^\epsilon$-(carboxymethyl)lysine in atherosclerotic vascular lesions as a marker for local oxidative stress", Atherosclerosis, vol. 144, issue 1, pp. 41-47, (1999). Abstract Only.
Soreide, K. et al., "Epidemiological-molecular evidence of metabolic reprogramming on proliferation, autophagy and cell signaling in pancreas cancer", Cancer Letters, vol. 356, issue 2, part A, pp. 281-288, (2015) Abstract Only.
Krautwald, M. et al., "Advanced glycation end products as biomarkers and gerontotoxins—a basis to explore methylglyoxal-lowering agents for Alzheimer's disease?", Experimental Gerontology, vol. 45, issue 10, pp. 744-751, (2010). Abstract Only.
Leclerc, E., "Development of monoclonal antibodies to inhibit RAGE activation in pancreatic tumors", North Dakota State University, Center for diagnostic and therapeutic strategies in pancreatic cancer, 1 page, (2019), found at www.ndsu.edu/centers/pancreaticcancer/former_investigators/leclerc_project/.
Yamagishi, S-I., et al., "DNA-aptamers raised against AGEs as a blocker of various aging- related disorders", Glycoconjugate Journal, vol. 33, pp. 683-690, (2016).
Kawaguchi, M. et al., "Glyoxal inactivates glutamate transporter-1 in cultured rat astrocytes", Neuropathology, vol. 25, pp. 27-36, (2005).
Scicchitano, B.M. et al., "Counteracting muscle wasting in aging and neuromuscular diseases: the critical role of IGF-1", Aging, vol. 1, No. 5, pp. 451-457, (2009).
Hanssen, N.M.J et al., "Higher levels of advanced glycation endproducts in human carotid atherosclerotic plaques are associated with a rupture-prone phenotype", European Heart Journal, vol. 35, pp. 1137-1146, (2014).
Southern, L. et al., "Immunohistochemical study of N-epsilon-carboxymethyl lysine (CML) in human brain: relation to vascular dementia", BMC Neuology, vol. 7, article No. 35, pp. 1-8, (2007).
Ramunas, J. et al., "Transient delivery of modified mRNA encoding TERT rapidly extends telomeres in human cells", The FASEB Journal, vol. 29, No. 5, pp. 1930-1939, (2015).
Gutierrez-Reyes, G. et al., "Cellular senescence in livers from children with end stage liver disease", Plos One, vol. 5, issue 4, pp. 1-5, (2010).
Extended European Search Report dated May 29, 2020 for European application No. 19210193.9-1111, 8 pages.
Taguchi, A. et al., "Blockade of RAGE-amphoterin signalling suppresses tumour growth and metastases", Nature, vol. 405, pp. 354-360, (2000).
Janeway, C.A. Jr. et al., "Appendix I. Immunologists' toolbox", Immunobiology: The immune system in health and disease, 5th edition, Garland Science, (2001), found at www.ncbi.nim.nih.gov/books/NBK10755/, (2001).
Haus, J.M. et al., "Collagen, cross-linking, and advanced glycation end products in aging human skeletal muscle", Journal of Applied Physiology, vol. 103, pp. 2068-2076, (2007).
Yi, H-S. et al., "T-cell senescence contributes to abnormal glucose homeostasis in humans and mice", Cell Death and Disease, vol. 10, No. 249, pp. 1-15, (2019).
Al-Motawa, M. et al., "Vulnerabilities of the SARS-CoV-2 virus to proteotoxicity—opportunity for repurposed chemotherapy of COVID-19 infection", Cell-Reports, 43 pages, found at www.ssrn.com/abstract=3582068, (2020).
D'Adda di Fagagna, F., "Living on a break: cellular senescence as a DNA-damage response", Nature Reviews Cancer, vol. 8, pp. 512-522, (2008).
"New biomarker for the prevention of arteriosclerosis", Atherosclerosis Prevention, vol. 14, No. 1, pp. 22-27, (2015).
Baxevanis, C.N. "Antibody-based cancer therapy", Expert Opinion Drug Discovery, vol. 3, No. 4, pp. 441-452, (2008).

(56) References Cited

OTHER PUBLICATIONS

Malatesta, M. "skeletal muscle features in myotonic dystrophy and sarcopenia: do similar nuclear mechanisms lead to skeletal wasting?", European Journal of Histochemistry, vol. 56, pp. 228-230, (2012).
Wingerchuk, D.M. et al., "Multiple sclerosis: Current and emerging disease-modifying therapies and treatment strategies", Mayo Clinic Proceedings, vol. 89, No. 2, pp. 225-240, (2014).
Matias-Guiu J.A. et al., "Amyloid proteins and their role in multiple sclerosis. Considerations in the use of amyloid-PET imaging", Frontiers in Neurology, vol. 7, article 53, pp. 1-7, (2016).
Sternberg, Z. et al., "Diagnostic potential of plasma carbxymethyllysine and carboxyethyllysine in multiple sclerosis", Journal of Neuroinflammation, vol. 7, No. 72, pp. 1-8, (2010).
Gunawan, M. et al., "A novel human systemic lupus erythematosus model in humanised mice", Nature Scientific Reports, vol. 7, pp. 1-11, (2017).
"Grants for Health Science of the Ministry of Health and Welfare, Comprehensive Research Project on Longevity Science", Long-Term Longitudinal Epidemiology, vol. 5, pp. 223-227, (1998).
Office Action dated Dec. 21, 2020 for Japanese application No. 2019-230026.
Shi, M. et al., "Low intensity-pulsed ultrasound induced apoptosis of human hepatocellular carcinoma cells in vitro", Ultrasonics, vol. 64, pp. 43-53, (2016). abstract only.
Myers, R. et al., "Ultrasound-mediated cavitation does not decrease the activity of small molecule, antibody or viral-based medicines", International Journal of Nanomedicine, vol. 13, pp. 337-349, (2018).
Danno, D. et al., "Effects of ultrasound on apoptosis induced by anti-CD20 antibody in CD20- positive B lymphoma cells", Ultrasonics Sonochemistry, vol. 15, pp. 463-471, (2008). abstract only.
Nande, R. et al., "Ultrasound-mediated oncolytic virus delivery and uptake for increased therapeutic efficacy: state of art", Oncolytic Virotherapy, vol. 4, pp. 193-205, (2015).
Abe, H. et al., "Targeted sonodynamic therapy of cancer using a photosensitizer conjugated with antibody against carcinoembryonic antigen", Anticancer Research, vol. 22, No. 3, pp. 1575-1580, (2002).
Jordao, J.F. et al., "Antibodies targeted to the brain with image-guided focused ultrasound reduces amyloid-ß plaque load in the TgCRND8 mouse model of alzheimer's disease", Plos One, vol. 5, issue 5, pp. 1-8, (2010).
Idbaih, A. et al., "Phase I/II study of an implantable device delivering low intensity pulsed ultrasound (LIPU) to disrupt the blood-brain barrier (BBB) followed by intravenous carboplatin chemotherapy in patients with recurrent glioblastoma (GBM)", Journal of Clinical Oncology, vol. 35, issue 15, supplemental 2034, pp. 1-6, (2017). abstract only.
Etame, A.B. et al., "Focused ultrasound disruption of the blood brain barrier: a new frontier for therapeutic delivery in molecular neuro-oncology", Neurosurg Focus, vol. 32, No. 1, pp. 1-17, (2012).
Wang, S. et al., "Pulsed high intensity focused ultrasound increases penetration and therapeutic efficacy of monoclonal antibodies in murine xenograft tumors", Journal of Controlled Release, vol. 162, No. 1, pp. 218-224, (2012).
Miller, D. et al., "Overview of therapeutic ultrasound applications and safety considerations", Journal of Ultrasound in Medicine, vol. 31, No. 4, pp. 623-634, (2012).
Udroiu, I., "Ultrasonic drug delivery in oncology", Journal of the Balkan Union of Oncology, vol. 20, No. 2, pp. 381-390, (2015).
Yu, T. et al., "Ultrasound: A chemotherapy sensitizer", Technology in Cancer Research and Treatment, vol. 5, No. 1, pp. 51-60, (2006).
Zhang, Z. et al., "Low intensity ultrasound promotes the sensitivity of rat brain glioma to doxorubicin by down-regulating the expressions of P-Glucoprotein and multidrug resistance protein 1 in vitro and in vivo", PLOS One, vol. 8, issue 8, pp. 1-13, (2013).
Sawai, Y. et al., "Effects of low-intensity pulsed ultrasound on osteosarcoma and cancer cells", Oncology Reports, vol. 28, pp. 481-486, (2012).
Takeuchi, R. et al., "Low-intensity pulsed ultrasound activates the phosphatidylinositol 3 kinase/Akt pathway and stimulates the growth of chondrocytes in three-dimensional cultures: a basic science study", Arthritis Research & Therapy, vol. 10, pp. 1-11, (2008).
Cui, J.H. et al., "Effects of low-intensity ultrasound on chondrogenic differentiation of mesenchymal stem cells embedded in polyglycolic acid: an in vivo study", Tissue Engineering, vol. 12, No. 1, pp. 75-82, (2006).
Muhlfeld, J. et al., "Influence of ultrasonic waves and enzymes on antigenic properties of human erythrocytes. I. Ultrasonic waves", Blut., vol. 30, No. 5, pp. 349-352, (1975). Abstract Only.
Rosenfeld, E. et al., "Positive and negative effects of diagnostic intensities of ultrasound on erythrocyte blood group markers", Ultrasonics, vol. 28, issue 3, pp. 155-158, (1990). Abstract Only.
Aviles Jr., F., "Contact low-frequency ultrasound used to accelerate granulation tissue proliferation and rapid removal of nonviable tissue in colonized wounds: A case study", Wound Management and Prevention, pp. 1-6, (2011).
Chen, R. et al., "Ultrasound-accelerated immunoassay, as exemplified by enzyme immunoassay of choriogonadotropin", Clinical Chemistry, vol. 30, No. 9, pp. 1446-1451, (1984).
Lin, C-H. et al., "Advanced glycosylation end products induce nitric oxide synthase expression in C6 glioma cells involvement of a p38 MAP kinase-dependent mechanism", Life Sciences, vol. 69, pp. 2503-2515, (2001).
Stoczynska-Fidelus, E. et al., "Spontaneous in vitro senescence of glioma cells confirmed by an antibody against IDH1R132H" Anticancer Research, vol. 34, pp. 2859-2868, (2014).
Kinoshita, M. et al., "Noninvasive localized delivery of Herceptin to the mouse brain by MRI- guided focused ultrasound-induced blood-brain barrier disruption", Proceedings of the National Academy of Science, vol. 103, No. 31, p. 11719-11723, (2006).
Nisbet, R.M. et al., "Combined effects of scanning ultrasound and a tau-specific single chain antibody in a tau transgenic mouse model", Brain, A Journal of Neurology, vol. 140, pp. 1220-1230, (2017).
Sun, T. et al., "Closed-loop control of targeted ultrasound drug delivery across the blood- brain/tumor barriers in a rat glioma model", Proceedings of the National Academy of Science, pp. e10281-e10290, (2017).
Liu, H-L. et al., "Blood-brain barrier disruption with focused ultrasound enhances delivery of chemotherapeutic drugs for glioblastoma treatment", Radiology, vol. 255, No. 2, pp. 415-425, (2010).
Zhao, B. et al., "Blood-brain barrier disruption induced by diagnostic ultrasound combined with microbubbles in mice", Oncotarget, vol. 9, No. 4, pp. 4897-4914, (2018).
Neergaard, L., "Ultrasound opens brain barrier, a step to better care", AZCentral.com, p. 1, (2018).
Houston-Edwards, K., "Wave of the Future?", PBS.org, pp. 1-6, found at www.pbs.org/wgbh/nova/article/hifu/, (2016).
Allen, K.D. et al., "Evaluating intra-articular drug delivery for the treatment of osteoarthritis in a rat model", Tissue Engineering: Part B, vol. 16, No. 1, pp. 81-92, (2010).
Eguchi, K. et al., "Whole-brain low-intensity pulsed ultrasound therapy markedly improves cognitive dysfunctions in mouse models of dementia—crucial roles of endothelial nitric oxide synthase", Brain Stimulation, vol. 11, pp. 959-973, (2018).
Ninomiya, K. et al., "Targeted sonodynamic therapy using protein-modified TiOz nanoparticles", Ultrasonics Sonochemistry, vol. 19, pp. 607-614, (2012).
Watson, K.D. et al., "Ultrasound increases nanoparticle delivery by reducing intratumoral pressure and increasing transport in epithelial and epithelial-mesenchymal transition tumors", Cancer Research, vol. 72, No. 6, pp. 1485-1493, (2012).
Endo, S. et al., "Porphyrin derivatives-mediated sonodynamic therapy for malignant gliomas in vitro", Ultrasound in Medicine and Biology, vol. 41, issue 9, pp. 2458-2465, (2015).
Zhang, Z. et al., "Low frequency and intensity ultrasound induces apoptosis of brain glioma in rats mediated by caspase-3, Bcl-2, and survivin", Brain Research, vol. 1473, pp. 25-34, (2012). Abstract Only.
Wang, P. et al., "Membrane damage effect of continuous wave ultrasound on K562 human leukemia cells", Journal of Ultrasound in Medicine, vol. 31, pp. 1977-1986, (2012).

(56) References Cited

OTHER PUBLICATIONS

Wood, A.K.W. et al., "A review of low-intensity ultrasound for cancer therapy", Ultrasound in Medicine and Biology, vol. 41, No. 4, pp. 905-928, (2015).
Lejbkowicz, F. et al., "Distinct sensitivity of normal and malignant cells to ultrasound in vitro", Environmental Health Perspectives, vol. 105, supplement 6, pp. 1575-1578, (1997).
Purkayastha, S. et al., "Transcranial doppler ultrasound: Technique and application", Seminars in Neurology, vol. 32, No. 4, pp. 411-420, (2012).
Liman, J. et al., "Transcranial ultrasound in adults and children with movement disorders", Perspectives in Medicine, vol. 1, pp. 349-352, (2012).
Product Description of "US 1000 3rd Edition Portable Ultrasound Unit 1-mHz", TENSpros, found at www.tenspros.com/US-1000-3rd-edition-portable-ultrasound-du1025.html, printed on Oct. 24, 2018.
El-Taieb, M.A. et al., "Oxidative stress and acrosomal morphology: A cause of infertility in patients with normal semen parameters", Middle East Fertility Society Journal, vol. 20, pp. 79-85, (2015).
Liu, D.Y. et al., "Defective sperm-zona pellucida interaction: a major cause of failure of fertilization in clinical in-vitro fertilization", Human Reproduction, vol. 15, No. 3, pp. 702-708, (2000).
Uhler, M.L., "Sperm morphology", Fertility Centers of Illinois, pp. 1-2, printed on Apr. 12, 2018.
Mallidis, C. et al., "Advanced glycation end products accumulate in the reproductive tract of men with diabetes", International Journal of Andrology, vol. 32, pp. 295-305, (2008).
Henkel, R.R. et al., "Sperm preparation for ART", Reproductive Biology and Endocrinology, vol. 1, pp. 1-22, (2003).
Ng, K.K. et al., "Sperm output of older men", Human Reproduction, vol. 19, No. 8, pp. 1811-1815, (2004).
Harris, I.D. et al., "Fertility and the aging male", Reviews in Urology, vol. 13, No. 4, pp. e184-e190, (2011).
Almeida, S. et al., "Fertility and sperm quality in the aging male", Current Pharmaceutical Design, vol. 23, issue 30, pp. 4429-4437, (2017). Abstract Only.
Kidd, S.A. et al., "Effects of male age on semen quality and fertility: a review of the literature", Fertility and Sterility, vol. 75, No. 2, pp. 237-248, (2001).
Sugimoto, K. et al., "The application of life style diseases-animal models to the research for sarcopenia", Clinical Calcium, vol. 24, No. 10, pp. 51-58, (2014).
International Search Report and written opinion dated Jul. 16, 2021 for PCT application No. PCT/US2020/057539.
Lilienthal, G-M, et al., "Potential of murine IgG1 and human IgG4 to inhibit the classical complement and Fcγ receptor activation pathways", Frontiers in Immunology, vol. 9, article 958, pp. 1-9, (2018).
Kiyoshi, M. et al., "Affinity improvement of a therapeutic antibody by structure-based computational design: generation of electrostatic interactions in the transition state stabilizes the antibody-antigen complex", PLOS One, vol. 9, issue 1, pp. 1-9, (2014).
Yamashita, K. et al., "Kotai antibody builder: automated high-resolution structural modeling of antibodies", Bioinofrmatics, vol. 30, No. 22, pp. 3279-3280, (2014).
Ye, J. et al., "IgBLAST: an immunoglobulin variable domain sequence analysis tool", Nucleic Acids Research, vol. 41, pp. W34-W40, (2013).
Esquivel, R.O. et al., "Decoding the building blocks of life from the perspective of quantum information", Advances in Quantum Mechanics, chapter 27, pp. 641-669, (2013).
Chilelli, N.C. et al., "AGEs, rather than hyperglycemia, are responsible for microvascular complications in diabetes: a "glycoxidation-centric" point of view", Nutrition, Metabolism & Cardiovascular Diseases, vol. 23, issue 10, pp. 913-919, (2013).
Palmer, A.K. et al., "Targeting senescent cells alleviates obesity-induced metabolic dysfunction", Aging Cell, vol. 18, pp. 1-15, (2019).

Thompson, P.J. et al., "Targeted elimination of senescent beta cells prevents type 1 diabetes", Cell Metabolism, vol. 29, pp. 1045-1060, (2019).
Bardeesy, N. et al., "Both p16Inkda and the p19$^{Arf}$_p53 pathway constrain progression of pancreatic adenocarcinoma in the mouse", PNAS, vol. 103, No. 15, pp. 5947-5952, (2006).
Sharpless, N.E. et al., "The differential impact of P16$^{Ink4a}$or p19$^{ARF}$deficiency on cell growth and tumorigenesis", Oncogene, vol. 23, pp. 379-385, (2004).
Pan, Q. et al., "Blocking neuropilin-1 function has an additive effect with anti-VEGF to inhibit tumor growth", Cancer Cell, vol. 11, pp. 53-67, (2007).
Hung, L-F. et al., "Advanced glycation end products induce T cell apoptosis: Involvement of oxidative stress, caspase and the mitochondrial pathway", Mechanisms of Ageing and Development, vol. 131, pp. 682-691, (2010).
Son, S. et al., "Advanced glycation end products impair NLRP3 inflammasome-mediated innate immune responses in macrophages", Journal of Biological Chemistry, vol. 292, No. 50, pp. 20437-20448, (2017).
Farboud, B. et al., "Development of a polyclonal antibody with broad epitope specificity for advanced glycation endproducts and localization of these epitopes in bruch's membrane of the aging eye", Molecular Vision, vol. 5, No. 11, 6 pages, (1999).
Invitation to Pay Additional Fee and Partial International Search Report dated Aug. 13, 2021 PCT application No. PCT/US2021/030184.
Tamura, M. et al., "Structural correlates of an anticarcinoma antibody: Identification of specificity-determining residues (SDRs) and development of a minimally immunogenic antibody variant by retention of SDRs only", The Journal of Immunology, vol. 164, No. 3, pp. 1432-1441, (2000).
International Search Report and written opinion dated Oct. 18, 2021 for PCT application No. PCT/US2021/030184.
Yamamoto, Y. et al., "Advanced glycation endproducts-receptor interactions stimulate the growth of human pancreatic cancer cells through the induction of platelet-derived growth factor-B", Biochemical and Biophysical Research Communications, vol. 222, pp. 700-705, (1996).
Sellegounder, D. et al., "Advanced glycation end products (AGEs) and its receptor, RAGE, modulate age-dependent COVID-19 morbidity and mortality. A review and hypothesis", International Immunopharmacology, vol. 98, pp. 107806-1-107806-8, (2021).
International Search Report and written opinion dated Nov. 24, 2021 for PCT application No. PCT/US2021/034777.
Graham, F.L. et al., "Characteristics of a human cell line transformed by DNA from human adenovirus type 5", Journal of General Virology, vol. 36, issue 1, pp. 59-74, (1977).
Munch, G. et al., "Advanced glycation endproducts and their pathogenic roles in neurological disorders", Amino Acids, vol. 42, No. 4, pp. 1221-1236, (2010).
Lin, J-A., et al., "Glycative stress from advanced glycation end products (AGEs) and dicarbonyls: An emerging biological factor in cancer onset and progression", Molecular Nutrition & Food Research, vol. 60, No. 8, pp. 1850-1864, (2016).
Muyldermans, S. et al., "Distinct antibody species: Structural differences creating therapeutic opportunities", Current Opinion in Immunology, vol. 40, pp. 7-13, (2016).
Rosenberg, C. et al., "Age is an important determinant in humoral and T cell responses to immunization with hepatitis B surface antigen", Human Vaccines & Immunotherapeutics, vol. 9, No. 7, pp. 1466-1476, (2013).
Choi, Y-G. et al., "Characterization of anti-advanced glycation end product antibodies to nonenzymatically lysine-derived and arginine-derived glycated products", Journal of Immunoassay and Immunochemistry, vol. 30, No. 4, pp. 386-399, (2009).
Kirkland, J.L. et al., "Senolytic drugs: from discovery to translation", Journal of Internal Medicine, vol. 288, No. 5, pp. 518-536, (2020).
Dunbar, J. et al., "SAbPred: a structure-based antibody prediction server", Nucleic Acids Research, vol. 44, Web Server Issue, pp. W474-W478, (2016).

(56) References Cited

OTHER PUBLICATIONS

Pedotti, M. et al., "Computational docking of antibody-antigen complexes, opportunities and pitfalls illustrated by influenza hemagglutinin", International Journal of Molecular Sciences, vol. 12, pp. 226-251, (2011).
Drevin, V.E. et al., "Biological age and methods for its determination", Volgograd State Agrarian University, Monograph, Volgograd, pp. 1-143, (2015).
Yabuuchi, J. et al., "Association of advanced glycation end products with sarcopenia and frailty in chronic kidney disease", Scientific Reports, pp. 1-12, (2020).
Zhang, C. et al., "FOXO1 mediates advanced glycation end products induced mouse osteocyte-like MLO-Y4 cell apoptosis and dysfunctions", Journal of Diabetes Research, vol. 2019, article id 6757428, pp. 1-11, (2019).
Dubey, N.K. et al., "Adipose-derived stem cells attenuates diabetic osteoarthritis via inhibition of glycation-mediated inflammatory cascade", Aging and Disease, vol. 10, No. 3, pp. 483-496, (2019).
Tanaka, K. et al., "Nϵ-(carboxymethyl) lysine represses hair follicle formation by inhibiting sonic hedgehog expression in a NF-KB-independent manner", International Journal of Dermatology and Clinical Research, vol. 5, No. 1, pp. 006-011, (2019).
Bao, Z. et al., "Nϵ-carboxymethyl-lysine negatively regulates foam cell migration via the vav1/rac1 pathway", Journal of Immunology Research, vol. 2020, article id 1906204, pp. 1-10, (2020).
Upton, J.H. et al., "Oxidative stress-associated senescence in dermal papilla cells of men with androgenetic alopecia", Journal of Investigative Dermatology, vol. 135, pp. 1244-1252, (2015).
Waaijer, M.E.C. et al., "P16INK4a positive cells in human skin are indicative of local elastic fiber morphology, facial wrinkling, and perceived age", Journals of Gerontology: Biological Sciences, vol. 71, No. 8, pp. 1022-1028, (2016).
Scott, A.M. et al., "Antibody therapy of cancer", Nature Reviews, vol. 12, pp. 278-287, (2012).
Allen, T.M. et al., "Humanized immune system mouse models: progress, challenges and opportunities", Nature Immunology, vol. 20, No. 7, pp. 770-774, (2019).
Krtolica, A et al., "Senescent fibroblasts promote epithelial cell growth and tumorigenesis: A link between cancer and aging", Proceedings of the National Academy of Science, vol. 98, No. 21, p. 12072-12077, (2001).
Shaw, T.J et al., "Wound-associated skin fibrosis: mechanisms and treatments based on modulating the inflammatory response", Endocrine, Metabolic & Immune Disorders - Drug Targets, vol. 10, No. 4, pp. 320-330, (2010). Abstract Only.
Bitterman, p. B et al., "Fibroproliferative disorders", Chest, vol. 99, No. 3, p. 81S-84S, (1991).
Pan, J et al., "Inhibition of Bcl-2/xl with ABT-263 selectively kills senescent type II pneumocytes and reverses persistent pulmonary fibrosis induced by ionizing radiation in mice", International Journal of Radiation Oncology, vol. 99, No. 2, pp. 353-361, (2017).
Yilmaz, O et al., "Dasatinib attenuated bleomycin-induced pulmonary fibrosis in mice", Growth Factors, pp. 1-10, (2015).
Kato, M et al., "Dasatinib suppresses TGFB-induced epithelial mesenchymal transition and inhibits pulmonary fibrosis", European Respiratory Journal, vol. 44, pp. 1-4, (2014).
Yagmur, E et al., "Elevation of Nϵ-(carboxymethyl)lysine-modified advanced glycation end products in chronic liver disease is an indicator of liver cirrhosis", Clinical Biochemistry, vol. 39, pp. 39-45, (2006).
Duffield, U.S., "Cellular and molecular mechanisms in kidney fibrosis", The Journal of Clinical Investigation, vol. 124, No. 6, pp. 2299-2306, (2014).
Weiler-Normann, C et al., "Mouse models of liver fibrosis", Z Gastroenterol, vol. 45, pp. 43-50, (2007).
Midgley, A.C et al., "Transforming growth factor-B1 (TGF-31)-stimulated fibroblast to myofibroblast differentiation is mediated by hyaluronan (HA)-facilitated epidermal growth factor receptor (EGFR) and CD44 co-localization in lipid rafts", The Journal of Biological Chemistry, vol. 288, No. 21, p. 14824-14838, (2013).
Schafer, M.J et al., "Cellular senescence mediated fibrotic pulmonary disease", Nature Communications, vol. 8, pp. 1-11, (2017).
Harris, W.T et al., "Myofibroblast differentiation and enhanced Tgf-B signaling in cystic fibrosis lung disease", Plos One, vol. 8, issue 8, pp. 1-8, (2013).
Bataller, R et al., "Liver fibrosis", The Journal of Clinical Investigation, vol. 115, No. 2, pp. 209-218, (2005).
Wynn, T.A., "Fibrotic disease and the TH1/TH2 paradigm", Nature Reviews Immunology, vol. 4, No. 8, pp. 583-594, (2004).
Calhoun, C et al., "Senescent cells contribute to the physiological remodeling of aged lungs", Journals of Gerontology: Biological Sciences, vol. 71, No. 2, pp. 153-160, (2016).
"About PF", The Pulmonary Fibrosis Foundation, pp. 1-9, printed on Jul. 18, 2017.
Definition of "Idiopathic pulmonary fibrosis" printed from Wikipedia, the free encyclopedia on Aug. 4, 2014 found at http://en.wikipedia.org/wiki/Idiopathic_pulmonary_fibrosis.
Definition of "Epithelial-mesenchymal transition" printed from Wikipedia, the free encyclopedia on Apr. 4, 2010 found at http://en.wikipedia.org/wiki/Epithelial-mesenchymal_transition.
Definition of "Pulmonary fibrosis" printed from Wikipedia, the free encyclopedia on Mar. 27, 2022 found at http://en.wikipedia.org/wiki/Pulmonary_fibrosis.
Mayo Clinic Staff, "Myelofibrosis", Mayo Clinic, pp. 1-2, (2017).
Bristol-Myers Squibb, "Safety evaluation of Dasatinib in subjects with scleroderma pulmonary fibrosis", Clinical Trials, 12 pages, (2012).
University of Michigan, "Beneficial effects of quercetin in chronic obstructive pulmonary disease (COPD) (Quercetin)", Clinical Trials, 14 pages, (2012).
Wake Forest University Health Sciences, "Targeting pro-inflammatory cells in idiopathic pulmonary fibrosis: a human trial (IPF)", Clinical Trials, 7 pages, (2017).
Scleroderma Research Foundation, "For patients, current treatments available for scleroderma patients", Scleroderma Research Foundation, pp. 1-2, printed on Feb. 26, 2018.
"Scleroderma, What is it?", National Institute of Arthritis and Musculoskeletal and Skin Diseases, pp. 1-8, printed on Feb. 26, 2018.
Definition of "Progeroid syndromes" printed from Wikipedia, the free encyclopedia on May 25, 2022 found at http://en.wikipedia.org/wiki/Progeroid_syndromes.
Haddadi, G.H. et al., "Hesperidin as radioprotector against radiation-induced lung damage in rat: A histopathological study", Journal of Medical Physics, vol. 42, No. 1, pp. 25-32, (2017).
Wilgus, T.A. et al., "Regulation of scar formation by vascular endothelial growth factor", Laboratory Investigation, vol. 88, pp. 579-590, (2008).
Leeman, K.T. et al., "Lung stem and progenitor cells in tissue homeostasis and disease", Current Topics in Developmental Biology, vol. 107, pp. 207-233, (2014).
Shaw, J.N. et al., "NE-(carbosymethyl)lysine (CML) as a biomarker of oxidative stress in long-lived tissue proteins", Methods in Molecular Biology, vol. 186, pp. 129-137, (2002).
Palmer, J.L. et al., "Combined radiation and burn injury results in exaggerated early pulmonary inflammation", Radiation Research, vol. 180, No. 3, pp. 276-283, (2013).
Meng, A. et al., "Ionizing radiation and busulfan induce premature senescence in murine bone marrow hematopoietic cells", Cancer Research, vol. 63, pp. 5414-5419, (2003).
Formenti, S.C. et al., "Combining radiotherapy and cancer immunotherapy: A paradigm shift", Journal of the National Cancer Institute, vol. 105, issue 4, pp. 256-265, (2013).
Flament, F. et al., "Effect of the sun on visible clinical signs of aging in Caucasian skin", Clinical, Cosmetic and Investigational Dermatology, vol. 6, pp. 221-232, (2013).
Richardson, R.B. et al., "Ionizing radiation and aging: rejuvenating an old idea", Aging, vol. 1, No. 11, pp. 887-902, (2009).
Rohani, A. et al., "A case control study of cardiovascular health in chemical war disabled Iranian victims", Indian Journal of Critical Care Medicine, vol. 14, No. 3, pp. 109-112, (2010).
Cupit-Link, M.C. et al., "Biology of premature ageing in survivors of cancer", ESMO Open Cancer Horizons, vol. 2, pp. 1-8, (2017).

(56) References Cited

OTHER PUBLICATIONS

Smith, R.L. et al., "Premature and accelerated aging: HIV or HAART?", Frontiers in Genetics, vol. 3, article 328, pp. 1-10, (2013).
Zota, A.R. et al., "Associations of cadmium and lead exposure with leukocyte telomere length: Finding from National Health and Nutrition Examination Survey, 1999-2002", American Journal of Epidemiology, vol. 181, No. 2, pp. 127-136, (2015).
White S.S. et al., "An overview of the effects of dioxins and dioxin-like compounds on vertebrates, as documented in human and ecological epidemiology", Journal of Environmental Science and Health, Part C, Environmental Carcinogenesis and Ecotoxicology Reviews, vol. 27, No. 4, pp. 197-211, (2009).
Ribas, J. et al., "Biomechanical strain exacerbates inflammation on a progeria-on-a-chip model", Small, vol. 13, issue 15, pp. 1-3, (2017). Abstract Only D'Orazio, J et al., "UV radiation and the skin", International Journal of Molecular Sciences, vol. 14, pp. 12222-12248, (2013).
Eisenreich, W. et al., "How viral and intracellular bacterial pathogens reprogram the metabolism of host cells to allow their intracellular replication", Frontiers in Cellular and Infection Microbiology, vol. 9, article 42, pp. 1-24, (2019).
Mayer, K.A. et al., "Hijacking the supplies: Metabolism as a novel facet of virus-host interaction", Frontiers in Immunology, vol. 10, article 1533, pp. 1-9, (2019).
"Covid-19: novel coronavirus, tackling coronavirus with WP1122", Moleculin, pp. 1-10, found at www.moleculin.com/covid-19/, (2020).
Wei, C. et al., "uPAR isoform 2 forms a dimer and induces severe kidney disease in mice", The Journal of Clinical Investigation, vol. 129, No. 5, pp. 1946-1959, (2019).
Wei, C. et al., "Circulating CD40 autoantibody and suPAR synergy drives glomerular injury". Annals of Translational Medicine, vol. 3, No. 19, pp. 1-5, (2015).
Reiser, J., "A humanized mouse model of FSGS", Rush University Medical Center, pp. 1-3, printed on Apr. 10, 2020.
Tanji, N. et al., "Expression of advanced glycation end product and their cellular receptor RAGE in diabetic nephropathy and nondiabetic renal disease", Journal of the American Society of Nephrology, vol. 11, No. 9, pp. 1656-1666, (2000).
Oldfield, M.D. et al., "Advanced glycation end products cause epithelial-myofibroblast transdifferentiation via the receptor for advanced glycation end products (RAGE)", The Journal of Clinical Investigation, vol. 108, No. 12, pp. 1853-1863, (2001).
Suzuki, D. et al., "Immunohistochemical evidence for an increased oxidative stress and carbonyl modification of proteins in diabetic glomerular lesions", Journal of the American Society of Nephrology, vol. 10, pp. 822-832, (1999).
Horie, K. et al., "Immunohistochemical colocalization of glycoxidation products and lipid peroxidation products in diabetic renal glomerular lesions. Implication for glycoxidative stress in the pathogenesis of diabetic nephropathy", The Journal of Clinical Investigation, vol. 100, No. 12, pp. 2995-3004, (1997),.
Kushiro, M. et al., "Accumulation of Nsigma-(carboxymethyl)lysine and changes in glomerular extracellular matrix components in Otsuka long-evans tokushima fatty rat: A model of spontaneous NIDDM", Nephron, vol. 79, No. 4, pp. 458-468, (1998). Abstract Only.
Valentijn, F.A. et al., "Cellular senescence in the aging and diseased kidney", Journal of Cell Communication and Signaling, vol. 12, No. 1, pp. 69-82, (2018).
Wang, W-J. et al., "Cellular senescence, senescence-associated secretory phenotype, and chronic kidney disease", Oncotarget, vol. 8, No. 38, pp. 64520-64533, (2017).
Dicarlo, A.L. et al., "Aging in the context of immunological architecture, function and disease outcomes", Trends in Immunology, vol. 30, No. 7, pp. 293-294, (2009).
Stortz, J.A. et al., "Old mice demonstrate organ dysfunction as well as prolonged inflammation, Immunosuppression, and weight loss in a modified surgical sepsis model", Critical Care Medicine, vol. 47, No. 11, pp. e919-e929, (2019).
Cannizzo, E.S. et al., "Oxidative stress, inflamm-aging and immunosenescence", Journal of Proteomics, vol. 74, issue 11, pp. 2313-2323, (2011).
Bourke, C.D. et al., "Immune dysfunction as a cause and consequence of malnutrition", Trends in Immunology, vol. 37, No. 6, pp. 386-398, (2016).
Aranow, C., "Vitamin D and the immune system", Journal of Investigative Medicine, vol. 59, No. 6, pp. 881-886, (2011).
Taneja, V., "Sex hormones determine immune response", Frontiers in Immunology, vol. 9, article 1931, pp. 1-5, (2018).
Bryant, P.A. et al., "Sick and tired: does sleep have a vital role in the immune system?", Nature Reviews Immunology, vol. 4, pp. 457-467, (2004).
Aw, D. et al., "Immunosenescence: emerging challenges for an ageing population", Immunology, vol. 120, pp. 435-446, (2007).
Traore, K. et al., "Do advanced glycation end-products play a role in malaria susceptibility?", Parasite, vol. 23, No. 15, pp. 1-10, (2016).
Duggal, N.A. et al., "Major features of immunesenescence, including reduced thymic output, are ameliorated by high levels of physical activity in adulthood", Aging Cell, vol. 17, No. 2, pp. 1-13, (2018).
Montecino-Rodriguez, E. et al., "Causes, consequences, and reversal of immune system aging", The Journal of Clinical Investigation, vol. 123, No. 3, pp. 958-965, (2013).
Desai, S. et al., "Early immune senescence in HIV disease", Current HIV/AIDS Reports, vol. 7, No. 1, pp. 4-10, (2010).
Vivier, E., et al., "Innate or adaptive immunity? The example of natural killer cells", Science, vol. 331, No. 6013, pp. 44-49, (2011).
Kvell, K., "Thymic senescence", In tech open, pp. 1-11, found at http://dx.doi.org/10.5772/intechopen.87063, (2019).
Palmer, S. et al., "Thymic involution and rising disease incidence with age", Proceedings of the National Academy of Science, vol. 115, No. 8, pp. 1883-1888, (2018).
Wertheimer, T. et al., "Production of BMP4 by endothelial cells is crucial for endogenous thymic regeneration", Science Immunology, vol. 3, No. 19, pp. 1-11, (2018).
"Oxidative stress and cellular senescence in age-related thymic involution", Fight Aging!, pp. 1-4, found at www.fightaging.org/archives/2020/03/oxidative-stress-and-cellular-senescence-in-age-related-thymic-involution/, (2020).
Barbouti, A. et al., "Implications of oxidative stress and cellular senescence in age-related thymus involution", Oxidative Medicine and Cellular Longevity, vol. 2020, article ID 7986071, pp. 1-14, (2020).
El-Torky, M. et al., "Collagens in scar carcinoma of the lung", The American Journal of Pathology, vol. 121 No. 2, pp. 322-326, (1985).
Machahua, C. et al., "Increased AGE-RAGE ratio in idiopathic pulmonary fibrosis", Respiratory Research, vol. 17, No. 1, pp. 1-11, (2016).
Sirica, A.E. et al., "Desmoplastic stroma and cholangiocarcinoma: Clinical implications and therapeutic targeting", Hepatology, vol. 59, No. 6, pp. 2397-2402, (2014).
Toullec, A. et al., "Oxidative stress promotes myofibroblast differentiation and tumour spreading", EMBO Molecular Medicine, vol. 2, pp. 211-230, (2010).
Oya, T. et al., "Methylglyoxal modification of protein", The Journal of Biological Chemistry, vol. 274, No. 26, pp. 18492-18502, (1999).
Extended European Search Report dated Sep. 2, 2022 for European application No. 22157145.8-1111, 22 pages.
Johmura, Y. et al., "Senolysis by glutaminolysis inhibition ameliorates various age-associated disorders", Science, vol. 371, pp. 265-270, (2021).
Jun. 14, 2012, U.S. Appl. No. 12/994,421.
Jul. 21, 2009, PCT/US2009/44951.
Dec. 2, 2010, PCT/US2009/44951.
Apr. 26, 2012, PCT/US2011/053399.
Jul. 2, 2012, U.S. Appl. No. 12/951,768.
Mar. 30, 2012, U.S. Appl. No. 12/951,768.
Jun. 13, 2012, PCT/US2011/061387.
Jun. 27, 2012, PCT/US12/31446.
May 14, 2012, 200980118817.6.
Nov. 8, 2011, 09 751 639.7.

(56) References Cited

OTHER PUBLICATIONS

Jun. 12, 2012, 09751 639.7.
Jul. 20, 2012, U.S. Appl. No. 12/994,421.
Jul. 13, 2012, 10-2012-7026063.
Sep. 10, 2012, U.S. Appl. No. 12/994,421.
Nov. 5, 2012, U.S. Appl. No. 12/951,768.
Nov. 8, 2012, 2009248945.
Aug. 20, 2012, 209513.
Jan. 3, 2013, 09 751 639.7.
Feb. 26, 2013, U.S. Appl. No. 12/994,421.
Dec. 25, 2012, 2010152693.
Mar. 21, 2013, U.S. Appl. No. 12/951,768.
Feb. 28, 2013, 200980118817.6.
Feb. 28, 2013, 10-2010-7026063.
Mar. 27, 2013, U.S. Appl. No. 12/951,768.
Apr. 15, 2013, 2009248945.
May 21, 2013, U.S. Appl. No. 12/994,421.
Apr. 23, 2013, 2010152693.
May 30, 2013, PCT/US2011/061387.
May 22, 2013, 209513.
Jul. 18, 2013, U.S. Appl. No. 12/994,421.
Jul. 26, 2013, 09751639.7.
Apr. 2, 2013, 11775932.3.
Jul. 16, 2013, 2010/012473.
Jul. 29, 2013, U.S. Appl. No. 12/951,768.
Sep. 30, 2013, 10-2010-7026063.
Nov. 15, 2013, U.S. Appl. No. 12/951,768.
Oct. 10, 2013, PCT/US2012/031446.
Nov. 19, 2013, 2011-511734.
Oct. 10, 2013, 200980118817.6.
Dec. 20, 2013, U.S. Appl. No. 12/951,768.
Dec. 23, 2013, 10-2010-7026063.
Jan. 23, 2014, 09751639.7.
Feb. 4, 2014, 2009248945.
Mar. 18, 2014, 2010/012473.
May 7, 2014, 200980118817.6.
May 25, 2014, 209513.
May 26, 2014, 2010152693.
Jun. 17, 2014, 2010/012473.
Jun. 20, 2014, U.S. Pat. No. 2,724,886.
Jun. 22, 2014, 10-2013-7028228.
Jul. 29, 2014, 10-2010-7026063.
Jul. 29, 2014, 10-2012-7026483.
Sep. 3, 2014, U.S. Appl. No. 13/332,976.
Sep. 9, 2014, U.S. Appl. No. 14/247,081.
Sep. 12, 2014, 14170702.4.
Oct. 8, 2014, 200980118817.6.
Nov. 18, 2014, U.S. Appl. No. 13/332,976.
Nov. 18, 2014, U.S. Appl. No. 12/994,421.
Dec. 2, 2014, 209513.
Dec. 3, 2014, 2011-511734.
Jan. 13, 2015, U.S. Appl. No. 14/247,081.
Feb. 2, 2015, U.S. Appl. No. 14/247,081.
Dec. 16, 2014, 2010152693.
Feb. 5, 2015, U.S. Pat. No. 2,724,886.
Feb. 27, 2015, 10-2012-6026483.
Mar. 13, 2015, U.S. Appl. No. 12/994,421.
Mar. 13, 2015, U.S. Appl. No. 13/332,976.
Mar. 27, 2015, U.S. Appl. No. 12/994,421.
Apr. 1, 2015, U.S. Appl. No. 13/332,976.
Mar. 26, 2015, 200980118817.6.
Apr. 23, 2015, 13/332,976.
May 1, 2015, U.S. Appl. No. 13/332,976.
Apr. 27, 2015, 10-2013-7028228.
May 6, 2015, U.S. Appl. No. 14/247,081.
Apr. 20, 2015, 10-2015-7007520.
Jun. 11, 2015, U.S. Appl. No. 13/332,976.
Jul. 10, 2015, U.S. Appl. No. 14/247,081.
Jul. 21, 2015, U.S. Appl. No. 14/278,081.
Jun. 22, 2015, 2015-076575.
Jun. 5, 2015, 2011332143.
Jun. 22, 2015, 2014202548.
Jul. 17, 2015, 14170802.4.
Sep. 10, 2015, U.S. Appl. No. 13/876,157.
Sep. 2, 2015, U.S. Appl. No. 12/994,421.
Sep. 8, 2015, U.S. Pat. No. 2,724,886.
Jul. 27, 2015, MX/a/2013/013310.
Nov. 27, 2015, 10-2015-7007520.
Dec. 10, 2015, 14170802.4.
Jan. 8, 2016, 2014202548.
Jan. 11, 2016, 2011332143.
Jan. 12, 2016, 2015-076575.
Jan. 19, 2016, U.S. Appl. No. 12/994,421.
Jan. 25, 2016, 2011332143.
Mar. 30, 2016, U.S. Appl. No. 13/876,157.
Mar. 31, 2016, PCT/US2015/050154.
Apr. 6, 2016, MX/a/2013/013310.
Apr. 14, 2016, U.S. Pat. No. 2,724,886.
Apr. 28, 2016, 2014202548.
Jun. 20, 2016, 2014202548.
Jun. 15, 2016, 201510303227.8.
Aug. 24, 2016, 2016204196.
Apr. 14, 2016, 240242.
Jul. 19, 2016, 2016-098558.
Jul. 13, 2016, 2015114990.
Oct. 17, 2016, U.S. Appl. No. 13/876,157.
Oct. 26, 2016, U.S. Pat. No. 2,818,647.
Sep. 22, 2016, U.S. Appl. No. 14/974,095.
Dec. 30, 2016, 201510303227.8.
Dec. 29, 2016, 4875/KOLNP/2010.
Jan. 5, 2017, U.S. Appl. No. 13/876,157.
Dec. 2, 2016, PCT/US2016/039076.
Aug. 10, 2016, PCT/US2016/034880.
Feb. 21, 2017, 16198527.0.
Mar. 23, 2017, 11776932.3.
Feb. 20, 2017, U.S. Pat. No. 2,724,886.
May 1, 2017, U.S. Pat. No. 2,724,886.
Jan. 23, 2017, 240242.
Dec. 19, 2016, 2016-098558.
Feb. 15, 2017, MX/a/2013/013310.
Jan. 27, 2017, 2015114990.
Apr. 19, 2017, 2,818,647.
Feb. 13, 2017, U.S. Appl. No. 14/974,095.
May 17, 2017, PCT/US2017/018185.
Jun. 13, 2017, U.S. Appl. No. 14/974,561.
Mar. 30, 2017, PCT/US2015/050154.
Jun. 27, 2017, U.S. Appl. No. 14/974,095.
Nov. 24, 2016, 14170802.4.
May 10, 2017, 2017113349.
May 15, 2017, 201510303227.8.
May 29, 2017, 248652.
Aug. 8, 2017, 2015114990.
Aug. 23, 2017, 11776932.3.
Sep. 22, 2017, U.S. Appl. No. 14/974,095.
Sep. 29, 2017, PCT/US2017/027773.
Oct. 13, 2017, U.S. Pat. No. 2,818,647.
Oct. 18, 2017, 2015114990.
Nov. 15, 2017, U.S. Appl. No. 14/974,561.
Nov. 29, 2017, U.S. Pat. No. 2,818,647.
Nov. 30, 2017, U.S. Appl. No. 14/932,200.
Jan. 11, 2018, U.S. Appl. No. 14/974,095.
Jan. 30, 2018, U.S. Appl. No. 14/974,095.
Feb. 8, 2018, U.S. Appl. No. 14/974,561.
Feb. 21, 2018, U.S. Appl. No. 14/932,200.
Mar. 16, 2018, 11776932.3.
Apr. 30, 2018, 2017-086871.
May 11, 2018, U.S. Appl. No. 14/974,095.
May 14, 2018, U.S. Appl. No. 14/920,737.
May 21, 2018, U.S. Appl. No. 15/511,731.
May 21, 2018, U.S. Appl. No. 15/489,624.
May 29, 2018, U.S. Appl. No. 14/974,561.
Jun. 22, 2018, U.S. Pat. No. 2,818,647.
Jul. 20, 2018, U.S. Pat. No. 2,818,647.

(56) References Cited

OTHER PUBLICATIONS

Aug. 30, 2018, PCT/US2017/018185.
Sep. 5, 2018, U.S. Appl. No. 14/932,200.
Sep. 12, 2018, U.S. Appl. No. 14/920,737.
Sep. 14, 2018, 15772116.8.
Sep. 25, 2018, U.S. Appl. No. 14/974,561.
Oct. 23, 2018, U.S. Appl. No. 15/489,624.
Oct. 25, 2018, PCT/US2017/02773.
Nov. 15, 2018, U.S. Appl. No. 15/511,731.
Nov. 28, 2018, U.S. Appl. No. 15/720,912.
Dec. 6, 2018, 2017113349.
Dec. 13, 2018, U.S. Appl. No. 14/932,200.
Jan. 11, 2019, 17708098.3.
Jan. 23, 2019, U.S. Appl. No. 15/489,624.
Feb. 4, 2019, U.S. Appl. No. 15/863,811.
Feb. 6, 2019, U.S. Appl. No. 14/974,561.
Feb. 11, 2019, U.S. Appl. No. 15/863,784.
Feb. 14, 2019, U.S. Appl. No. 15/511,731.
Mar. 4, 2019, U.S. Appl. No. 14/920,737.
Mar. 12, 2019, U.S. Appl. No. 14/974,561.
Mar. 26, 2019, U.S. Appl. No. 15/720,912.
Apr. 10, 2019, U.S. Appl. No. 15/863,741.
Feb. 25, 2019, 1770898.3.
Dec. 25, 2018, PCT/US2016/039076.
Mar. 20, 2019, U.S. Appl. No. 15/863,828.
Mar. 31, 2019, 2017086871.
Apr. 8, 2019, 2017113349.
Jun. 7, 2019, U.S. Appl. No. 14/932,200.
Jul. 8, 2019, 2017-515740.
Aug. 15, 2019, U.S. Appl. No. 14/920,737.
Jun. 19, 2019, 18184822.7.
Jun. 27, 2019, U.S. Appl. No. 15/511,731.
Jul. 19, 2019, 17708098.3.
Sep. 25, 2019, U.S. Appl. No. 15/863,811.
Apr. 14, 2016, 14160802.4.
Sep. 8, 2017, 11776932.3.
Jan. 19, 2018, 11776932.3.
Feb. 7, 2018, 11776932.3.
Jan. 30, 2019, 15772116.8.
Aug. 30, 2019, 17737078.0.
Sep. 30, 2019, U.S. Appl. No. 15/863,784.
Oct. 7, 2019, U.S. Appl. No. 15/863,828.
Oct. 11, 2019, U.S. Appl. No. 15/953,244.
Oct. 11, 2019, U.S. Appl. No. 15/768,425.
Oct. 15, 2019, U.S. Appl. No. 16/092,743.
Oct. 21, 2019, U.S. Appl. No. 15/511,731.
Oct. 30, 2019, U.S. Appl. No. 15/720,912.
Nov. 1, 2019, U.S. Appl. No. 15/863,811.
Nov. 14, 2019, PCT/US2018/030931.
Nov. 20, 2019, U.S. Appl. No. 14/932,200.
Nov. 21, 2019, U.S. Appl. No. 15/863,784.
Jan. 23, 2019, 18184822.7.
Feb. 4, 2019, 15772116.8.
Feb. 14, 2019, 11776932.3.
Dec. 5, 2019, U.S. Appl. No. 15/863,741.
Dec. 11, 2019, U.S. Appl. No. 15/977,587.
Dec. 11, 2019, 18726656.4.
Dec. 20, 2019, U.S. Appl. No. 15/863,828.
Jan. 13, 2020, U.S. Appl. No. 14/920,737.
Jan. 29, 2020, 2018110885.
Jan. 27, 2020, U.S. Appl. No. 15/511,731.
Feb. 13, 2020, U.S. Appl. No. 15/863,741.
Feb. 7, 2020, U.S. Appl. No. 15/863,784.
Feb. 11, 2020, U.S. Appl. No. 15/863,811.
Jan. 14, 2020, 2017-515740.
Mar. 17, 2020, U.S. Appl. No. 15/768,425.
Mar. 20, 2020, U.S. Appl. No. 15/953,244
Mar. 31, 2020, U.S. Appl. No. 14/920,737.
Mar. 26, 2020, 2017113349.
Mar. 18, 2020, U.S. Appl. No. 16/092,743.
Mar. 5, 2020, 15772116.8.
Mar. 5, 2020, 2018-543120.
Apr. 16, 2020, U.S. Appl. No. 15/863,828.
Apr. 20, 2020, U.S. Appl. No. 15/863,741.
Apr. 3, 2020, 201580056616.3.
May 12, 2020, 2018-519727.
May 18, 2020, U.S. Appl. No. 15/720,912.
May 19, 2020, U.S. Appl. No. 14/932,200.
May 28, 2020, 2018132998.
May 25, 2020, 2018-543120.
May 29, 2020, 19210193.9.
May 28, 2020, U.S. Appl. No. 15/977,587.
Jun. 2, 2020, U.S. Appl. No. 16/077,713.
Jun. 12, 2020, 2015318036.
Jun. 18, 2020, U.S. Appl. No. 15/863,784.
Jun. 3, 2020, 258397.
Jun. 8, 2020, 251210.
Jun. 23, 2020, U.S. Appl. No. 14/920,737.
Jun. 24, 2020, 17737078.0.
Jun. 26, 2020, 201737009367.
Jun. 15, 2020, 2018-566505.
Jul. 13, 2020, 19210193.9.
Dec. 12, 2019, 17708098.3.
Jul. 23, 2020, U.S. Appl. No. 15/720,912.
Jul. 24, 2020, U.S. Appl. No. 15/863,784.
Jul. 20, 2020, U.S. Appl. No. 15/863,811.
Jul. 24, 2020, 15772116.8.
Aug. 4, 2020, U.S. Appl. No. 14/920,737.
Aug. 6, 2020, U.S. Appl. No. 15/953,244.
Aug. 12, 2020, U.S. Appl. No. 16/077,713.
Aug. 4, 2020, 2020-106264.
Aug. 26, 2020, U.S. Appl. No. 15/768,425.
Sep. 9, 2020, U.S. Appl. No. 16/440,747.
Sep. 16, 2020, U.S. Appl. No. 15/863,784.
Sep. 16, 2020, U.S. Appl. No. 15/953,244.
Sep. 29, 2020, U.S. Appl. No. 15/768,425.
Sep. 29, 2020, U.S. Appl. No. 15/863,811.
Sep. 17, 2020, U.S. Appl. No. 15/863,828.
Oct. 13, 2020, U.S. Appl. No. 15/863,741.
Oct. 21, 2020, U.S. Appl. No. 16/311,149.
Oct. 22, 2020, U.S. Appl. No. 15/863,811.
Oct. 27, 2020, U.S. Appl. No. 15/863,828.
Oct. 27, 2020, U.S. Appl. No. 15/863,741.
Nov. 5, 2020, U.S. Appl. No. 15/863,741.
Nov. 6, 2020, U.S. Appl. No. 16/092,743.
Nov. 12, 2020, 15/953,244.
Nov. 9, 2020, U.S. Appl. No. 14/920,737.
Nov. 19, 2020, U.S. Appl. No. 16/228,293.
Nov. 24, 2020, 2020-106264.
Nov. 24, 2020, U.S. Appl. No. 15/768,425.
Dec. 3, 2020, U.S. Appl. No. 15/863,784.
Dec. 9, 2020, U.S. Appl. No. 15/768,425.
Dec. 17, 2020, U.S. Appl. No. 15/863,741.
Dec. 17, 2020, U.S. Appl. No. 15/863,784.
Dec. 17, 2020, U.S. Appl. No. 15/863,828.
Dec. 21, 2020, 2019-230026.
Jan. 8, 2021, 2017219749.
Jan. 13, 2021, U.S. Appl. No. 15/863,741.
Jan. 6, 2021, U.S. Appl. No. 15/720,912.
Jan. 29, 2021, U.S. Appl. No. 16/092,743.
Jan. 12, 2021, 2016800599975.
Feb. 3, 2021, 2016800599975.
Jan. 28, 2021, U.S. Appl. No. 14/920,737.
Feb. 3, 2021, U.S. Appl. No. 15/977,587.
Feb. 10, 2021, U.S. Appl. No. 14/920,737.
Feb. 12, 2021, 2017219749.
Feb. 23, 2021, U.S. Appl. No. 16/077,713.
Mar. 8, 2021, 2201580056616.3.
Mar. 12, 2021, U.S. Appl. No. 15/863,784.
Mar. 15, 2021, U.S. Appl. No. 16/311,149.
Mar. 25, 2021, U.S. Appl. No. 15/863,784.
Mar. 17, 2021, 18184822.7.
Apr. 1, 2021, U.S. Appl. No. 16/228,293.

(56) References Cited

OTHER PUBLICATIONS

Mar. 25, 2021, 18726656.4.
May 12, 2021, 2015318036.
May 18, 2021, 201780024206.X.
May 25, 2021, U.S. Pat. No. 2,961,603.
Mar. 7, 2021, 261006.
May 21, 2021, 19210193.9.
May 21, 2021, U.S. Pat. No. 3,000,815.
Jun. 17, 2021, U.S. Appl. No. 16/311,149.
May 24, 2021, 2018-566505.
Jun. 10, 2021, 2020-085180.
Jun. 29, 2021, U.S. Appl. No. 15/720,912.
Jul. 7, 2021, U.S. Appl. No. 15/720,912.
Jul. 19, 2021, 2017-515740.
Aug. 6, 2021, U.S. Appl. No. 16/077,713.
Aug. 12, 2021, U.S. Appl. No. 15/977,587.
Aug. 30, 2021, U.S. Appl. No. 16/077,713.
Aug. 27, 2021, 2019139256.
Sep. 7, 2021, 2018110885.
Sep. 24, 2021, U.S. Appl. No. 16/311,149.
Sep. 17, 2021, MX/a/2017/003565.
Oct. 7, 2021, U.S. Appl. No. 16/228,293.
Sep. 3, 2021, 201780037571.4.
Sep. 18, 2021, 201580056616.3.
Oct. 20, 2021, U.S. Appl. No. 15/977,587.
Oct. 18, 2021, 2017-515740.
Oct. 28, 2021, U.S. Appl. No. 16/077,713.
Oct. 26, 2021, U.S. Appl. No. 15/720,912.
Oct. 28, 2021, U.S. Appl. No. 16/440,747.
Sep. 30, 2021, 10-2017-7009539.
Oct. 13, 2021, U.S. Pat. No. 3,000,815.
Nov. 15, 2021, U.S. Appl. No. 17/089,999.
Nov. 18, 2021, U.S. Appl. No. 16/311,149.
Dec. 8, 2021, U.S. Appl. No. 16/092,743.
Nov. 18, 2021, 283726.
Dec. 7, 2021, 2018110885.
Dec. 12, 2021, U.S. Appl. No. 16/383,348.
Dec. 6, 2021, 2021-155024.
Nov. 11, 2021, 10-2018-7031932.
Dec. 17, 2021, U.S. Appl. No. 15/720,912.
U.S. Appl. No. 16/228,293, filed Jan. 12, 2022.
Dec. 23, 2021, 15772116.8.
Dec. 1, 2021, 2019-230026.
filed Jan. 18, 2022, U.S. Appl. No. 17/089,999.
Jan. 6, 2022, 262222.
Feb. 1, 2022, U.S. Appl. No. 15/720,912.
Jan. 18, 2022, 20191392556.
Feb. 2, 2022, 251210.
Feb. 14, 2022, 2019-555873.
Feb. 28, 2022, U.S. Appl. No. 16/228,293.
Feb. 16, 2022, MX/a/2017/003565.
Mar. 11, 2022, 19210193.9.
Mar. 18, 2022, U.S. Appl. No. 17/089,999.
Mar. 21, 2022, U.S. Appl. No. 16/610,473.
Mar. 21, 2022, U.S. Appl. No. 16/228,293.
Mar. 10, 2022, 201827014696.
Mar. 16, 2022, 2018251183.
Mar. 11, 2022, U.S. Pat. No. 3,021,150.
Apr. 1, 2022, U.S. Appl. No. 16/077,713.
Apr. 11, 2022, U.S. Appl. No. 16/228,293.
Apr. 8, 2022, 201780024206.X.
Mar. 22, 2022, 2019-560086.
Apr. 27, 2022, 201780037571.4.
May 6, 2022, 201837030621.
May 30, 2022, 10-2017-7009539.
Jun. 13, 2022, U.S. Appl. No. 17/089,999.
Jun. 22, 2022, U.S. Appl. No. 16/228,293.
Jun. 23, 2022, U.S. Appl. No. 15/977,587.
Jun. 27, 2022, U.S. Appl. No. 16/383,348.
May 23, 2022, 16738275.3.
Jun. 30, 2022, U.S. Appl. No. 16/265,875.
Jul. 6, 2022, U.S. Appl. No. 16/440,747.
Jun. 28, 2022, MX/a/2018/009988.
Jun. 27, 2022, 2021-155024.
Jul. 18, 2022, 2019139256.
Jul. 29, 2022, U.S. Appl. No. 17/089,999.
Jul. 23, 2022, P6000510/2018.
Aug. 2, 2022, U.S. Appl. No. 16/228,293.
Jun. 23, 2022, 10-2018-7026021.
Aug. 18, 2022, U.S. Appl. No. 16/092,743.
Jul. 28, 2022, 10-2018-7031932.
Sep. 21, 2022, U.S. Appl. No. 16/610,473.
Sep. 12, 2022, U.S. Pat. No. 3,021,150.
Sep. 2, 2022, MX/a/2018/009988.
Oct. 12, 2022, U.S. Appl. No. 16/228,293.
Oct. 14, 2022 U.S. Appl. No. 17/089,999.
Oct. 14, 2022, U.S. Appl. No. 15/977,587.
Oct. 10, 2022, 201780024206.X.
Sep. 6, 2022, 10-2019-7035140.
Sep. 2, 2022, 22157145.8.
Oct. 27, 2022, U.S. Appl. No. 16/077,713.
Oct. 20, 2022, 2022-128911.
Oct. 31, 2022, U.S. Appl. No. 17/089,999.
Nov. 1, 2022, U.S. Appl. No. 16/228,293.
Nov. 17, 2022, U.S. Appl. No. 16/440,747.
Nov. 24, 2022, 2019139256.
Nov. 10, 2022, PCT/US2021/030184.
Dec. 9, 2022, U.S. Appl. No. 16/779,369.
Dec. 5, 2022, 201780037571.4.
Dec. 15, 2022, U.S. Appl. No. 16/383,348.
Dec. 12, 2022, 2019-560086.
Dec. 29, 2022, U.S. Appl. No. 16/440,747.
Dec. 30, 2022, U.S. Appl. No. 16/265,875.
Jan. 11, 2023, U.S. Appl. No. 16/440,747.
Dec. 26, 2022, 2022-168035.
Dec. 14, 2022, 270285.
Dec. 13, 2022, MX/a/2022/014630.
Jan. 19, 2023, 18184822.7.
Feb. 7, 2023, 17737078.0.
Feb, 28, 2023, U.S. Appl. No. 16/440,747.
Feb. 27, 2023, 2018-566505.
Feb. 21, 2023, 10-2018-7026021.
Mar. 3, 2023, U.S. Appl. No. 16/077,713.
Feb. 24, 2023, MX/a/2018/004545.
Mar. 29, 2023, U.S. Appl. No. 16/610,473.
Mar. 7, 2023, 18726656.4.
Mar. 24, 2023, 18725677.1.
Mar. 30, 2023, U.S. Appl. No. 16/077,713.
Mar. 16, 2023, U.S. Pat. No. 3,057,829.
Apr. 13, 2023, 2022-059633.
Mar. 21, 2023, 262222.
Mar. 24, 2023, 19773968.3.
Apr. 24, 2023, 2021-503581.
May 1, 2023, U.S. Appl. No. 16/440,747.
May 1, 2023, U.S. Appl. No. 15/977,587.
Apr. 29, 2023, 201880044776.X.
Jul. 16, 2021, PCT/US2020/057539.
May 25, 2023, U.S. Appl. No. 16/092,743.
Jun. 7, 2023, U.S. Appl. No. 17/262,684.
Jun. 14, 2023, U.S. Appl. No. 17/209,554.
Jun. 15, 2023, U.S. Appl. No. 18/050,915.
Jun. 19, 2023, 2022-128911.
Jun. 23, 2023, U.S. Appl. No. 16/779,369.
Jun. 22, 2023, PCT/US2021/062606.
Jun. 29, 2023, U.S. Appl. No. 17/177,140.
Jun. 26, 2023, 2021-507529.
Jul. 20, 2023, U.S. Appl. No. 16/077,713.
Jun. 22, 2023, 10-2023-7016986.
Jun. 29, 2023, 10-2018-7031932.
Aug. 10, 2023, U.S. Appl. No. 16/440,747.
Aug. 16, 2023, U.S. Appl. No. 15/977,587.
Aug. 17, 2023, U.S. Appl. No. 16/077,713.
Jul. 31, 2023, 2022-168035.

(56) References Cited

OTHER PUBLICATIONS

Aug. 14, 2023, MX/a/2018/004545.
Jun. 26, 2023, 201780037571.4.
Sep. 21, 2023, U.S. Appl. No. 15/977,587.
Sep. 21, 2023, U.S. Appl. No. 16/440,747.
Sep. 8, 2023 P6000510/2018.
Sep. 4, 2023, 2018-566505.
Jul. 26, 2023, 10-2019-7035140.
Sep. 19, 2023, 201837030621.
Oct. 5, 2023, U.S. Appl. No. 16/077,713.
Dec. 13, 2019, 4875/KOLNP/2010.
Jun. 9, 2021, 201737009367.
Sep. 14, 2023, 2019-230026.
Oct. 20, 2023, U.S. Appl. No. 16/265,875.
Oct. 17, 2023, 2017250301.
Nov. 21, 2023, U.S. Appl. No. 16/440,747.
Dec. 4, 2023, U.S. Appl. No. 15/977,587.
Dec. 4, 2023, 201827014696.
Dec. 12, 2023, U.S. Appl. No. 18/050,915.
Dec. 26, 2023, U.S. Appl. No. 16/610,473.
Jan. 2, 2024, U.S. Appl. No. 16/779,369.
Nov. 29, 2023, 10-2018-7010762.
Feb. 27, 2024, U.S. Appl. No. 17/268,413.
Jan. 2, 2024, 19759765.1.
Feb. 29, 2024, PCT/US2022/075226.
Feb. 19, 2024, 2021-507529.
Mar. 19, 2024, U.S. Appl. No. 17/544,636.
Mar. 31, 2024, U.S. Appl. No. 17/262,684.
Mar. 28, 2024, U.S. Appl. No. 16/779,369.
Mar. 29, 2024, 10-2023-7044845.
May 8, 2024, U.S. Appl. No. 18/050,915.
May 16, 2024, U.S. Appl. No. 18/050,915.
May 7, 2024, U.S. Pat. No. 3,059,803.
Apr. 8, 2024, 22765728.5.
Jun. 4, 2024, U.S. Appl. No. 16/779,369.
Feb. 5, 2024, 2023-64753.
May 31, 2024, U.S. Pat. No. 3,062,082.
May 3, 2024, 18726656.4.
Jun. 26, 2024, U.S. Appl. No. 16/779,369.
Jun. 21, 2024, 10-2023-7016986.
Aug. 12, 2024, U.S. Appl. No. 18/050,915.
Sep. 3, 2024, 283726.
U.S. Appl. No. 18/817,100, filed Aug. 27, 2024.

* cited by examiner

HUMANIZED MONOCLONAL ADVANCED GLYCATION END-PRODUCT ANTIBODY

SEQUENCE LISTING INCORPORATION BY REFERENCE

A Sequence Listing XML file is submitted herewith. This file named "SIWO-024-CON2-US_sequence_listing", created on Oct. 28, 2022, having a file size of 29 KB is hereby incorporated by reference.

BACKGROUND

Advanced glycation end-products (AGEs; also referred to as AGE-modified proteins, or glycation end-products) arise from a non-enzymatic reaction of sugars with protein sidechains (Ando, K. et al., Membrane Proteins of Human Erythrocytes Are Modified by Advanced Glycation End Products during Aging in the Circulation, *Biochem Biophys Res Commun.*, Vol. 258, 123, 125 (1999)). This process begins with a reversible reaction between a reducing sugar and an amino group to form a Schiff base, which proceeds to form a covalently-bonded Amadori rearrangement product. Once formed, the Amadori product undergoes further rearrangement to produce AGEs.

Antibodies that bind to an AGE-modified protein on a cell are known in the art. Examples include those described in U.S. Pat. No. 5,702,704 to Bucala and U.S. Pat. No. 6,380,165 to Al-Abed et al. Non-human anti-AGE antibodies are also commercially available. For example, R&D Systems, Inc. (Minneapolis; MN) sells a murine anti-AGE antibody raised against carboxymethyl lysine conjugated with keyhole limpet hemocyanin. Commercially-available antibodies are designed for laboratory or diagnostic purposes and may contain material that is not suited for in vivo use in animals or humans. These antibodies are not therapeutic antibodies and are not intended for administration to a human subject.

AGEs and AGE-modified cells have been associated with several pathological conditions including diabetic complications, inflammation, retinopathy, nephropathy, stroke, endothelial cell dysfunction, and neurodegenerative disorders (Bierhaus A, "AGEs and their interaction with AGE-receptors in vascular disease and diabetes mellitus. I. The AGE concept," Cardiovasc Res, Vol. 37(3), 586-600 (1998)). The association between AGEs and various pathological conditions, diseases and disorders has led to the identification of AGEs as a therapeutic target. Therapies for targeting and removing AGE-modified cells include the application of ultrasound and the administration of antibodies, including humanized antibodies, that bind to AGEs (see, for example, WO 2009/143411, US 2013/0243785 and US 2016/0215043). Antibody-based immunotherapies are particularly desirable because of their ability to specifically target and kill cells that express the antigen to which the antibody binds while sparing cells that do not express the antigen.

Antibodies are Y-shaped proteins composed of two heavy chains and two light chains. The two arms of the Y shape form the fragment antigen-binding (Fab) region while the base or tail of the Y shape forms the fragment crystallizable (Fc) region of the antibody. Antigen binding occurs at the terminal portion of the fragment antigen-binding region (the tips of the arms of the Y shape) at a location referred to as the paratope, which is a set of complementarity determining regions (also known as CDRs or the hypervariable region). The complementarity determining regions vary among different antibodies and gives a given antibody its specificity for binding to a given antigen. The fragment crystallizable region of the antibody determines the result of antigen binding and may interact with the immune system, such as by triggering the complement cascade or initiating antibody-dependent cell-mediated cytotoxicity (ADCC).

Therapeutic monoclonal antibodies were initially produced in mice using the hybridoma technique. A significant problem with administering murine and other unmodified non-human antibodies to human subjects is the risk of the human immune system attacking the non-human antibodies. Many human patients that receive murine antibodies develop an allergic reaction termed the human anti-mouse antibody response (HAMA response). The HAMA response could be mild, such as a rash, or life-threatening, such as renal failure. In addition, the human immune system will often neutralize the murine antibodies, reducing their half-life and impairing their ability to target the intended antigen.

Non-human antibodies may be made less immunogenic to humans by engineering the antibodies to contain a combination of non-human and human antibody components. The non-human antibody is chosen for its specificity for a desired target antigen. A chimeric antibody may be produced by combining the variable region of a non-human antibody with a human constant region. Chimeric antibodies are approximately 70% human and are less immunogenic than unmodified non-human antibodies. A humanized antibody may be produced by replacing the complementarity determining regions (CDRs) of a human antibody with those of a non-human antibody. Humanized antibodies are approximately 95% human and are less immunogenic than chimeric antibodies due to the inclusion of a greater amount of human antibody components. Humanization is a well-known scientific technique (see, for example, U.S. Pat. No. 5,693,762) and has progressed to the point that custom antibody humanization services are commercially available.

SUMMARY

In a first aspect, the invention is a humanized monoclonal advanced glycation end-product antibody comprising a heavy chain and a light chain. The heavy chain comprises an amino acid sequence having at least 90% sequence identity, preferably at least 95% sequence identity, more preferably at least 98% sequence identity, with at least one amino acid sequence selected from the group consisting of SEQ ID NO: 2, SEQ ID NO: 3, SEQ ID NO: 4 and SEQ ID NO: 5. The light chain comprises an amino acid sequence having at least 90% sequence identity, preferably at least 95% sequence identity, more preferably at least 98% sequence identity, with at least one amino acid sequence selected from the group consisting of SEQ ID NO: 12, SEQ ID NO: 13, SEQ ID NO: 14 and SEQ ID NO: 15. The antibody binds a carboxymethyllysine-modified protein or peptide.

In a second aspect, the invention is a humanized monoclonal advanced glycation end-product antibody comprising a heavy chain, having a heavy chain variable region, and a light chain, having a light chain variable region. The heavy chain variable region comprises an amino acid sequence having at least 90% sequence identity, preferably at least 95% sequence identity, more preferably at least 98% sequence identity, with at least one amino acid sequence selected from the group consisting of SEQ ID NO: 7, SEQ ID NO: 8, SEQ ID NO: 9 and SEQ ID NO: 10. The light chain variable region comprises an amino acid sequence having at least 90% sequence identity, preferably at least 95% sequence identity, more preferably at least 98% sequence identity, with at least one amino acid sequence selected from the group consisting of SEQ ID NO: 17, SEQ ID NO: 18, SEQ ID NO: 19 and SEQ ID NO: 20. The antibody binds a carboxymethyllysine-modified protein or peptide.

In a third aspect, the invention is a humanized monoclonal advanced glycation end-product antibody comprising a heavy chain and a light chain. The heavy chain comprises an amino acid sequence having at least one amino acid sequence selected from the group consisting of SEQ ID NO: 2, SEQ ID NO: 3, SEQ ID NO: 4 and SEQ ID NO: 5. The light chain comprises an amino acid sequence having at least one amino acid sequence selected from the group consisting of SEQ ID NO: 12, SEQ ID NO: 13, SEQ ID NO: 14 and SEQ ID NO: 15. The antibody binds a carboxymethyllysine-modified protein or peptide.

In a fourth aspect, the invention is a humanized monoclonal advanced glycation end-product antibody comprising a heavy chain, having a heavy chain variable region, and a light chain, having a light chain variable region. The heavy chain variable region comprises an amino acid sequence having at least one amino acid sequence selected from the group consisting of SEQ ID NO: 7, SEQ ID NO: 8, SEQ ID NO: 9 and SEQ ID NO: 10. The light chain variable region comprises an amino acid sequence having at least one amino acid sequence selected from the group consisting of SEQ ID NO: 17, SEQ ID NO: 18, SEQ ID NO: 19 and SEQ ID NO: 20. The antibody binds a carboxymethyllysine-modified protein or peptide.

In a fifth aspect, the invention is a composition comprising humanized monoclonal advanced glycation end-product antibody and a pharmaceutically acceptable carrier.

In a sixth aspect, the invention is a method of treating a human subject who has been diagnosed with a pathological condition, disease or disorder associated with AGEs or AGE-modified cells comprising administering to the subject a composition comprising a humanized monoclonal advanced glycation end-product antibody. The antibody comprises a heavy chain comprising an amino acid sequence having at least 90% sequence identity, preferably at least 95% sequence identity, more preferably at least 98% sequence identity, with at least one amino acid sequence selected from the group consisting of SEQ ID NO: 2, SEQ ID NO: 3, SEQ ID NO: 4 and SEQ ID NO: 5. The antibody comprises a light chain comprising an amino acid sequence having at least 90% sequence identity, preferably at least 95% sequence identity, more preferably at least 98% sequence identity, with at least one amino acid sequence selected from the group consisting of SEQ ID NO: 12, SEQ ID NO: 13, SEQ ID NO: 14 and SEQ ID NO: 15.

Definitions

The term "peptide" means a molecule composed of 2-50 amino acids.

The term "protein" means a molecule composed of more than 50 amino acids.

The terms "advanced glycation end-product," "AGE," "AGE-modified protein or peptide," "glycation end-product" and "AGE antigen" refer to modified proteins or peptides that are formed as the result of the reaction of sugars with protein side chains that further rearrange and form irreversible cross-links. This process begins with a reversible reaction between a reducing sugar and an amino group to form a Schiff base, which proceeds to form a covalently-bonded Amadori rearrangement product. Once formed, the Amadori product undergoes further rearrangement to produce AGEs. AGE-modified proteins and antibodies to AGE-modified proteins are described in U.S. Pat. No. 5,702,704 to Bucala and U.S. Pat. No. 6,380,165 to Al-Abed et al. Glycated proteins or peptides that have not undergone the necessary rearrangement to form AGEs, such as N-deoxyfructosyllysine found on glycated albumin, are not AGEs. AGEs may be identified by the presence of AGE modifications (also referred to as AGE epitopes or AGE moieties) such as 2-(2-furoyl)-4(5)-(2-furanyl)-1H-imidazole ("FFI"); 5-hydroxymethyl-1-alkylpyrrole-2-carbaldehyde ("Pyrraline"); 1-alkyl-2-formyl-3,4-diglycosyl pyrrole ("AFGP"), a non-fluorescent model AGE; carboxymethyllysine; carboxyethyllysine; and pentosidine. ALI, another AGE, is described in U.S. Pat. No. 6,380,165.

The terms "advanced glycation end-product antibody", "antibody that binds to an AGE-modified protein on a cell", "anti-AGE antibody" or "AGE antibody" mean an antibody that binds to an AGE-modified protein or peptide, where the protein or peptide which has been AGE-modified is a protein or peptide normally found bound on the surface of a cell. An "advanced glycation end-product antibody", "antibody that binds to an AGE-modified protein on a cell", "anti-AGE antibody" or "AGE antibody" does not include an antibody or other protein which binds with the same specificity and selectivity to both the AGE-modified protein or peptide, and the same non-AGE-modified protein or peptide (that is, the presence of the AGE modification does not increase binding). AGE-modified albumin is not an AGE-modified protein on a cell, because albumin is not a protein normally found bound on the surface of cells. An "advanced glycation end-product antibody", "antibody that binds to an AGE-modified protein on a cell", "anti-AGE antibody" or "AGE antibody" only includes those antibodies which lead to removal, destruction, or death of the cell. Also included are antibodies which are conjugated, for example to a toxin, drug, or other chemical or particle.

The term "humanized antibody" means a genetically engineered antibody in which the complementarity determining regions (CDRs) of a human antibody have been replaced with those of a non-human antibody, and where the antibody variable region amino acid sequence is closer to human than to other species.

The term "variant" means a nucleotide, protein or amino acid sequence different from the specifically identified sequences, wherein one or more nucleotides, proteins or amino acid residues is deleted, substituted or added. Variants may be naturally-occurring allelic variants, or non-naturally-occurring variants. Variants of the identified sequences may retain some or all of the functional characteristics of the identified sequences.

The term "percent (%) sequence identity" is defined as the percentage of amino acid residues in a candidate sequence that are identical to the amino acid residues in a reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways using publicly available computer software such as BLAST, BLAST-2, ALIGN or Megalign (DNASTAR) software. Preferably, % sequence identity values are generated using the sequence comparison computer program ALIGN-2. The ALIGN-2 sequence comparison computer program is publicly available from Genentech, Inc. (South San Francisco, CA), or may be compiled from the source code, which has been filed with user documentation in the U.S. Copyright Office and is registered under U.S. Copyright Registration No. TXU510087. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program ALIGN-2 in that program's alignment of A and B, and where Y is the total number of amino acid residues in B. Where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained using the ALIGN-2 computer program.

DETAILED DESCRIPTION

Figure 1:
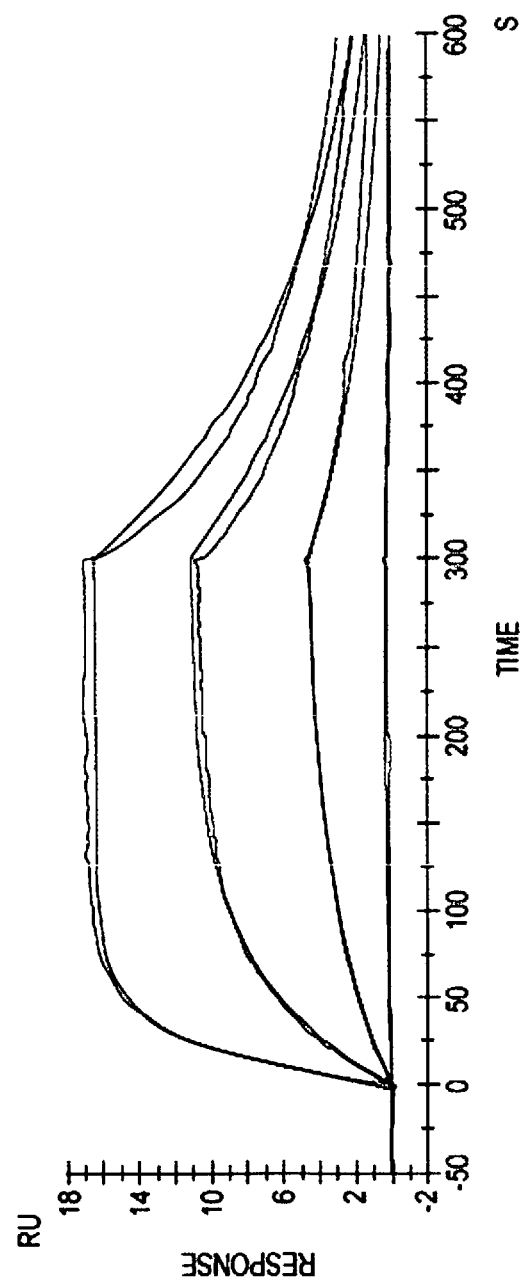
FIG. 1 illustrates the antibody binding of a commercially-available murine anti-AGE antibody.

The present invention is a novel humanized monoclonal antibody that binds to an AGE-modified protein or peptide on a cell. Specifically, the anti-AGE antibody binds to a carboxymethyllysine-modified protein or peptide on a cell. The antibody is suitable for in vivo administration to a human subject and preferably is substantially non-immunogenic to humans. The antibody may optionally be conjugated to a toxin or other agent for inducing cell death. The antibody may also be included in a composition with a pharmaceutically acceptable carrier. The antibody is believed to have superior antigen binding properties as compared to comparable commercially-available non-human anti-AGE antibodies.

The humanized monoclonal advanced glycation end-product antibody includes a heavy chain having a protein sequence selected from the group consisting of SEQ ID NO: 2, SEQ ID NO: 3, SEQ ID NO: 4 and SEQ ID NO: 5 and a light chain having a protein sequence selected from the group consisting of SEQ ID NO: 12, SEQ ID NO: 13, SEQ ID NO: 14 and SEQ ID NO: 15. The variable domains of the humanized heavy chains may have a protein sequence selected from the group consisting of SEQ ID NO: 7, SEQ ID NO: 8, SEQ ID NO: 9 and SEQ ID NO: 10. The variable domains of the humanized light chains may have a protein sequence selected from the group consisting SEQ ID NO: 17, SEQ ID NO: 18, SEQ ID NO: 19 and SEQ ID NO: 20.

The anti-AGE antibody binds to proteins or peptides having a carboxymethyllysine AGE modification. Carboxymethyllysine (also known as N(epsilon)-(carboxymethyl)lysine, N(6)-carboxymethyllysine, 2-Amino-6-(carboxymethylamino)hexanoic acid and CML) is found on proteins or peptides and lipids as a result of oxidative stress and chemical glycation. Carboxymethyllysine-modified proteins or peptides are recognized by the receptor RAGE which is expressed on a variety of cells. Carboxymethyllysine has been well-studied and carboxymethyllysine-related products are commercially available. For example, Cell Biolabs, Inc. sells CML-BSA antigens, CML polyclonal antibodies, CML immunoblot kits, and CML competitive ELISA kits (www.cellbiolabs.com/cml-assays). CML-ovalbumin (CML-OVA) is a preferred control for verifying antibody binding.

The anti-AGE antibody has a low rate of dissociation from the antibody-antigen complex, or $k_d$ (also referred to as $k_{back}$ or off-rate), preferably at most $6\times10^{-3}$, $5\times10^{-3}$, $1\times10^{-3}$, $8\times10^{-4}$, $5\times10^{-4}$, $1\times10^{-4}$, $8\times10^{-5}$, $5\times10^{-5}$ or $1\times10^{-5}$ (sec$^{-1}$). Preferably, the binding properties of the anti-AGE antibody are superior to the murine carboxymethyl lysine monoclonal antibody (Clone 318003) available from R&D Systems, Inc. (Minneapolis, MN; catalog no. MAB3247), illustrated in FIG. 1.

The binding of the humanized antibodies may be evaluated, for example, by dose-dependent binding ELISA or cell-based binding assay. Preferably, the binding of the humanized anti-AGE antibodies is equivalent or superior to the binding of non-human anti-AGE antibodies.

The anti-AGE antibody may destroy AGE-modified cells through antibody-dependent cell-mediated cytotoxicity (ADCC). ADCC is a mechanism of cell-mediated immune defense in which an effector cell of the immune system actively lyses a target cell whose membrane-surface antigens have been bound by specific antibodies. ADCC may be mediated by natural killer (NK) cells, macrophages, neutrophils or eosinophils. The effector cells bind to the Fc portion of the bound antibody. Administration of NK cells, such as NK92 cells (a cell line available from NantKwest, Culver City, CA), together with, or subsequent to, administration of anti-AGE antibodies, can enhance the compliment activity and therefore the effectiveness of the anti-AGE antibodies to kill cells. The anti-AGE antibody may also destroy AGE-modified cells through complement-dependent cytotoxicity (CDC). In CDC, the complement cascade of the immune system is triggered by an antibody binding to a target antigen.

The anti-AGE antibody may optionally be conjugated to an agent that causes the destruction of AGE-modified cells. Examples of such agents include toxins, cytotoxic agents, magnetic nanoparticles and magnetic spin-vortex discs.

A toxin, such as a pore-forming toxin (PFT) (Aroian R. et al., "Pore-Forming Toxins and Cellular Non-Immune Defenses (CNIDs)," *Current Opinion in Microbiology*, 10:57-61 (2007)), conjugated to an anti-AGE antibody may be injected into a patient to selectively target and remove AGE-modified cells. The anti-AGE antibody recognizes and binds to AGE-modified cells. Then, the toxin causes pore formation at the cell surface and subsequent cell removal through osmotic lysis.

Magnetic nanoparticles conjugated to the anti-AGE antibody may be injected into a patient to target and remove AGE-modified cells. The magnetic nanoparticles can be heated by applying a magnetic field in order to selectively remove the AGE-modified cells.

As an alternative, magnetic spin-vortex discs, which are magnetized only when a magnetic field is applied to avoid self-aggregation that can block blood vessels, begin to spin when a magnetic field is applied, causing membrane disruption of target cells. Magnetic spin-vortex discs, conjugated to anti-AGE antibodies specifically target AGE-modified cell types, without removing other cells.

A humanized monoclonal anti-AGE antibody or a variant thereof may include a heavy chain having at least 90%, 91%, 92%, 93%, 94%, 95%, 96%, 97%, 98%, 99%, or 100% sequence identity to the amino acid sequence of SEQ ID NO: 2, SEQ ID NO: 3, SEQ ID NO: 4 or SEQ ID NO: 5, including post-translational modifications thereof. A heavy chain having at least 90%, 91%, 92%, 93%, 94%, 95%, 96%, 97%, 98%, or 99% sequence identity may contain substitutions (e.g., conservative substitutions), insertions, or deletions relative to the reference sequence, but an anti-AGE antibody including that sequence retains the ability to bind to AGE. The substitutions, insertions, or deletions may occur in any portion of the sequence.

A humanized monoclonal anti-AGE antibody or a variant thereof may include a heavy chain variable region having at least 90%, 91%, 92%, 93%, 94%, 95%, 96%, 97%, 98%, 99%, or 100% sequence identity to the amino acid sequence of SEQ ID NO: 7, SEQ ID NO: 8, SEQ ID NO: 9 or SEQ ID NO: 10, including post-translational modifications thereof. A variable region having at least 90%, 91%, 92%, 93%, 94%, 95%, 96%, 97%, 98%, or 99% sequence identity may contain substitutions (e.g., conservative substitutions), insertions, or deletions relative to the reference sequence, but an anti-AGE antibody including that sequence retains the ability to bind to AGE. The substitutions, insertions, or deletions may occur in any portion of the sequence.

A humanized monoclonal anti-AGE antibody or a variant thereof may include a light chain having at least 90%, 91%, 92%, 93%, 94%, 95%, 96%, 97%, 98%, 99%, or 100% sequence identity to the amino acid sequence of SEQ ID NO: 12, SEQ ID NO: 13, SEQ ID NO: 14 or SEQ ID NO: 15, including post-translational modifications thereof. A light chain having at least 90%, 91%, 92%, 93%, 94%, 95%, 96%, 97%, 98%, or 99% sequence identity may contain substitutions (e.g., conservative substitutions), insertions, or deletions relative to the reference sequence, but an anti-AGE antibody including that sequence retains the ability to bind to AGE. The substitutions, insertions, or deletions may occur in any portion of the sequence.

A humanized monoclonal anti-AGE antibody or a variant thereof may include a light chain variable region having at least 90%, 91%, 92%, 93%, 94%, 95%, 96%, 97%, 98%, 99%, or 100% sequence identity to the amino acid sequence of SEQ ID NO: 17, SEQ ID NO: 18, SEQ ID NO: 19 or SEQ ID NO: 20, including post-translational modifications thereof. A variable region having at least 90%, 91%, 92%, 93%, 94%, 95%, 96%, 97%, 98%, or 99% sequence identity may contain substitutions (e.g., conservative substitutions), insertions, or deletions relative to the reference sequence, but an anti-AGE antibody including that sequence retains the ability to bind to AGE. The substitutions, insertions, or deletions may occur in any portion of the sequence.

Antibody fragments may be used in place of whole antibodies. Preferably, the fragments are derived from an antibody composed a heavy chain having a protein sequence selected from the group consisting of SEQ ID NO: 2, SEQ ID NO: 3, SEQ ID NO: 4 and SEQ ID NO: 5 and a light chain having a protein sequence selected from the group consisting of SEQ ID NO: 12, SEQ ID NO: 13, SEQ ID NO: 14 and SEQ ID NO: 15. Antibodies may be broken down into smaller fragments by digestion with enzymes. Papain digestion cleaves the N-terminal side of inter-heavy chain disulfide bridges to produce Fab fragments. Fab fragments include the light chain and one of the two N-terminal domains of the heavy chain (also known as the Fd fragment). Pepsin digestion cleaves the C-terminal side of the inter-heavy chain disulfide bridges to produce F(ab')$_2$ fragments. F(ab')$_2$ fragments include both light chains and the two N-terminal domains linked by disulfide bridges. Pepsin digestion may also form the Fv (fragment variable) and Fc (fragment crystallizable) fragments. The Fv fragment contains the two N-terminal variable domains. The Fc fragment contains the domains which interact with immunoglobulin receptors on cells and with the initial elements of the complement cascade. Pepsin may also cleave immunoglobulin G before the third constant domain of the heavy chain ($C_H3$) to produce a large fragment F(abc) and a small fragment pFc'. Antibody fragments may alternatively be produced recombinantly.

Humanized antibody sequences may be compared to known antibody sequences to predict their efficacy. For example, humanized antibody sequences may be analyzed by eye and/or computer modeling to identify sequences that will most likely retain antigen binding. Humanized antibody sequences may also be screened for the presence of sequences that are known to increase in the possibility of an immunogenic response. For example, presentation of peptide sequences in the groove of MHC Class II molecules leads to activation of $CD8^+$ T-cells and an immunogenic response. In order to reduce this response, antibodies may be designed to avoid the incorporation of "T-cell epitopes" that can activate T-cells by reducing the affinity of binding to the MHC Class II molecules. Residues within the human frameworks or the CDRs may be mutated to the human germline equivalent (a process known as germlining) to remove potential MHC-II epitopes.

The anti-AGE antibody may be obtained by humanizing a murine monoclonal anti-AGE antibody. A murine monoclonal anti-AGE antibody has the heavy chain protein sequence shown in SEQ ID NO: 1 (the protein sequence of the variable domain is shown in SEQ ID NO: 6) and the light chain protein sequence shown in SEQ ID NO: 11 (the protein sequence of the variable domain is shown in SEQ ID NO: 16). The antibody may be made recombinantly in Chinese Hamster Ovary (CHO) cells. The humanized monoclonal antibodies may be purified after synthesis. For example, the antibodies may be purified using MabSelect SuRe Protein A medium (GE Healthcare).

The humanized monoclonal anti-AGE antibodies may be included in a composition with a pharmaceutically acceptable carrier. A "pharmaceutically acceptable carrier" includes any and all solvents, dispersion media, coatings, antibacterial and antifungal agents, isotonic and absorption delaying agents, and the like, compatible with pharmaceutical administration. Preferred examples of such carriers or diluents include water, saline, Ringer's solutions and dextrose solution. Supplementary active compounds can also be incorporated into the compositions. Solutions and suspensions used for parenteral administration can include a sterile diluent, such as water for injection, saline solution, polyethylene glycols, glycerin, propylene glycol or other synthetic solvents; antibacterial agents such as benzyl alcohol or methyl parabens; antioxidants such as ascorbic acid or sodium bisulfite; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injection include sterile aqueous solutions or dispersions for the extemporaneous preparation of sterile injectable solutions or dispersion. Various excipients may be included in pharmaceutical compositions of antibodies suitable for injection. For intravenous administration, suitable carriers include physiological saline, bacteriostatic water, CREMOPHOR EL® (BASF; Parsippany, NJ) or phosphate buffered saline (PBS). In all cases, the composition must be sterile and should be fluid so as to be administered using a syringe. Such compositions should be stable during manufacture and storage and must be preserved against contamination from microorganisms such as bacteria and fungi. Various antibacterial and anti-fungal agents, for example, parabens, chlorobutanol, phenol, ascorbic acid, and thimerosal, can contain microorganism contamination. Isotonic agents such as sugars, polyalcohols, such as mannitol, sorbitol, and sodium chloride can be included in the composition. Compositions that can delay absorption include agents such as aluminum monostearate and gelatin. Sterile injectable solutions can be prepared by incorporating antibodies, and optionally other therapeutic components, in the required amount in an appropriate solvent with one or a combination of ingredients as required, followed by sterilization. Methods of preparation of sterile solids for the preparation of sterile injectable solutions include vacuum drying and freeze-drying to yield a solid.

For administration by inhalation, the antibodies may be delivered as an aerosol spray from a nebulizer or a pressurized container that contains a suitable propellant, for example, a gas such as carbon dioxide. Antibodies may also be delivered via inhalation as a dry powder, for example using the iSPERSE™ inhaled drug delivery platform (PULMATRIX, Lexington, MA).

An appropriate dosage level of each type of antibody will generally be about 0.01 to 500 mg per kg of patient body weight. Preferably, the dosage level will be about 0.1 to about 250 mg/kg; more preferably about 0.5 to about 100 mg/kg. A suitable dosage level may be about 0.01 to 250 mg/kg, about 0.05 to 100 mg/kg, or about 0.1 to 50 mg/kg. Within this range the dosage may be 0.05 to 0.5, 0.5 to 5 or 5 to 50 mg/kg. Antibodies may be administered on a regimen of 1 to 4 times per day, such as once or twice per day. Antibodies typically have a long half-life in vivo, which may reduce the administration regimen to once a day, once a week, once every two or three weeks, once a month, or once every 60 to 90 days.

A subject that receives administration of an anti-AGE antibody may be tested to determine if the antibody has effectively removed AGE-modified cells. The presence of AGE-modified cells may be determined by measuring markers that are associated with AGE modification, such as $p16^{INK4a}$. Administration of antibody and subsequent testing may be repeated until the desired therapeutic result is achieved.

Unit dosage forms may be created to facilitate administration and dosage uniformity. Unit dosage form refers to physically discrete units suited as single dosages for the subject to be treated, containing a therapeutically effective quantity of one or more types of antibodies in association with the required pharmaceutical carrier. Preferably, the unit dosage form is in a sealed container and is sterile.

Any human subject who has been diagnosed with a pathological condition, disease or disorder associated with AGEs or AGE-modified cells may be treated by the methods herein described. Examples of pathological conditions, diseases or disorders that may be treated with the humanized monoclonal anti-AGE antibodies include Alzheimer's disease, amyotrophic lateral sclerosis (ALS or Lou Gehrig's Disease), chronic obstructive pulmonary disease (COPD), Huntington's chorea, idiopathic pulmonary fibrosis, muscular dystrophy (including Becker's, Duchenne, Limb-Girdle and Yamamoto's muscular dystrophy), macular degeneration, cataracts, diabetic retinopathy, Parkinson's disease, progeria (including Werner Syndrome and Hutchinson Gilford progeria), vitiligo, cystic fibrosis, atopic dermatitis, eczema, arthritis (including osteoarthritis, rheumatoid arthritis and juvenile rheumatoid arthritis), atherosclerosis, cancer and metastatic cancer (including, for example, breast cancer, triple negative breast cancer, lung cancer, melanoma, colon cancer, renal cell carcinoma, prostate cancer, cancer of the cervix, bladder cancer, rectal cancer, esophageal cancer, liver cancer, mouth and throat cancer, multiple myeloma, ovarian cancer, stomach cancer, pancreatic cancer and retinal blastoma cancers), cancer therapy-related disability or cancer therapy side effects, hypertension, glaucoma, osteoporosis, sarcopenia, cachexia, stroke, myocardial infarction, atrial fibrillation, transplantation rejection, diabetes mellitus—Type I, diabetes mellitus—Type II, radiation exposure, HIV treatment side effects, chemical weapons exposure, poisoning, inflammation, nephropathy, Lewy body dementia, prion disease (including bovine spongiform encephalopathy, Creutzfeldt-Jakob disease, scrapie, chronic wasting disease, kuru and fatal familial insomnia), lordokyphosis, auto-immune disorders, loss of adipose tissue, psoriasis, Crohn's disease, asthma, the physiological effects of aging (including "cosmetic" effects, such as wrinkling, age spots, hair loss, reduction in subcutaneous adipose tissue and thinning of the skin), idiopathic myopathy (including, for example, idiopathic inflammatory myopathy, idiopathic inflammatory myositis, polymyositis, dermatomyositis, sporadic inclusion body myositis and juvenile myositis), multiple sclerosis, neuromyelitis optica (NMO, Devic's disease or Devic's syndrome), epilepsy and adrenoleukodystrophy (ALD, X-linked adrenoleukodystrophy, X-ALD, cerebral ALD or cALD).

A particularly preferred treatment group includes subjects who have been diagnosed with a pathological condition, disease or disorder associated with AGEs or AGE-modified cells but who are unable to receive conventional treatments. For example, metastatic cancer has been recognized as a condition associated with AGE-modified cells. A patient with metastatic cancer may not be able to undergo cancer treatments such as surgery, radiation therapy or chemotherapy due to other diagnoses, physical conditions or complications. For example, pregnant women cannot receive radiation therapy due to a risk of harm to the fetus. Aged or weakened patients, such as those experiencing cancer cachexia, may not be good candidates for surgery due to a risk of not surviving an invasive procedure. Patients who already have a compromised immune system or a chronic infection may not be able to receive chemotherapy since many chemotherapy drugs harm the immune system.

The anti-AGE antibodies may be used in cell separation processes, such as magnetic cell separation. In magnetic cell separation, the anti-AGE antibodies are attached to magnetic beads through a process called coating. The coated magnetic beads may then specifically bind to AGE-modified cells. The AGE-modified cells that have bound to anti-AGE antibodies coated on magnetic beads will then respond to an applied magnetic field, allowing the AGE-modified cells to be separated from non-AGE-modified cells. Magnetic cell separation may be used to isolate AGE-modified cells from tissue samples and fluid samples. The magnetic beads may be microbeads (0.5-500 μm) or nanoparticles (5-500 nm). Anti-AGE antibodies coated on magnetic beads may also be used in isolation processes such as immunoassays and immunoprecipitation. Similarly, anti-AGE antibodies coated on magnetic beads may be used to specifically target and separate AGE-modified proteins or peptides from tissue samples and fluid samples.

The anti-AGE antibodies may be used in cellular purification processes, such as immunopanning and immunoadsorption. Purification processes are useful in isolating desirable or unwanted cells from tissue cultures, cell cultures or blood. Cellular purification may be used in transplantations, such as a bone marrow transplant, or transfusions, such as a blood transfusion. Cellular purification is especially useful in autologous stem cell transplantation during chemotherapy to remove metastasizing malignant cells and concentrate beneficial stem cells. Immunopanning or immunoadsorption using an anti-AGE antibody may isolate AGE-modified cells from a tissue culture, cell culture or blood sample.

The one-letter amino acid sequence that corresponds to SEQ ID NO: 1 is

MGWTLVFLFLLSVTAGVHSQVQLLQPGAELVKPGASVKLACKASGYLFT
TYWMHWLKQRPGQGLEWIGEISPTNGRAYYNARFKSEATLTVDKSSNTA
YMQLSSLTSEASAVYYCARSFGNYEFAYWGQGTLVTVSVASTKGPSVFP
LAPSSKSTSGGTAALGCLVKDYFPEPVTVSWNSGALTSGVHTFPAVLQS
SGLYSLSSVVTVPSSSLGTQTYICNVNHKPSNTKVDKKVEPKSCDKTHTC
PPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVS
NKALPAPIEKTISKAKGQPREPQVYTLPPSRDELTKNQVSLTCLVKGFY
PSDIAVEWESNGQPENNYKTTPPVLDSDGSFFLYSKLTVDKSRWQQGNV
FSCSVMHEALHNHYTQKSLSLSPGK.

The one-letter amino acid sequence that corresponds to SEQ ID NO: 2 is

MGWTLVFLFLLSVTAGVHSEVQLLESGAEAKKPGASVKLSCKASGYLFT
TYWMHWVHQAPGQRLEWMGEISPTNGRAYYNARFKSRVTITVDKSASTA
YMELSSLRSEDTAVYYCARSFGNYEFAYWGQGTLVTVSSASTKGPSVFP
LAPSSKSTSGGTAALGCLVKDYFPEPVTVSWNSGALTSGVHTFPAVLQS
SGLYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKV
SNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGN
VFSCSVMHEALHNHYTQKSLSLSPGK.

The one-letter amino acid sequence that corresponds to SEQ ID NO: 3 is

MGWTLVFLFLLSVTAGVHSQVQLVQSGAEVKKPGASVKVSCKASGYLFT
TYWMHWVRQAPGQRLEWIGEISPTNGRAYYNARFKSRVTITRDTSASTA
YMELSSLRSEDTAVYYCARSFGNYEFAYWGQGTLVTVSSASTKGPSVFP
LAPSSKSTSGGTAALGCLVKDYFPEPVTVSWNSGALTSGVHTFPAVLQS
SGLYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKV
SNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGN
VFSCSVMHEALHNHYTQKSLSLSPGK.

The one-letter amino acid sequence that corresponds to SEQ ID NO: 4 is

MGWTLVFLFLLSVTAGVHSQVQLVQSGAEVKKPGSSVKVSCKASGYLFT
TYWMHWVRQAPGQGLEWMGEISPTNGRAYYNARFKSRVTITADKSTSTA
YMELSSLRSEDTAVYYCARSFGNYEFAYWGQGTLVTVSSASTKGPSVFP
LAPSSKSTSGGTAALGCLVKDYFPEPVTVSWNSGALTSGVHTFPAVLQS
SGLYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKV
SNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGN
VFSCSVMHEALHNHYTQKSLSLSPGK.

The one-letter amino acid sequence that corresponds to SEQ ID NO: 5 is

MGWTLVFLFLLSVTAGVHSQVQLVQSGAEVKKPGASVKVSCEASGYLFT
TYWMHWVRQAPGQGLEWMGEISPTNGRAYYNARFKSRVTITRDTSINTA
YMELSRLRSDDTAVYYCARSFGNYEFAYWGQGTLVTVSSASTKGPSVFP
LAPSSKSTSGGTAALGCLVKDYFPEPVTVSWNSGALTSGVHTFPAVLQS
SGLYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKV
SNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGN
VFSCSVMHEALHNHYTQKSLSLSPGK.

The one-letter amino acid sequence that corresponds to SEQ ID NO: 6 is

QVQLLQPGAELVKPGASVKLACKASGYLFTTYWMHWLKQRPGQGLEWIG
EISPTNGRAYYNARFKSEATLTVDKSSNTAYMQLSSLTSEASAVYYCAR
SFGNYEFAYWGQGTLVTVSV.

The one-letter amino acid sequence that corresponds to SEQ ID NO: 7 is

EVQLLESGAEAKKPGASVKLSCKASGYLFTTYWMHWVHQAPGQRLEWMG EISPTNGRAYYNARFKSRVTITVDKSASTAYMELSSLRSEDTAVYYCAR SFGNYEFAYWGQGTLVTVSS.

The one-letter amino acid sequence that corresponds to SEQ ID NO: 8 is

QVQLVQSGAEVKKPGASVKVSCKASGYLFTTYWMHWVRQAPGQRLEWIG EISPTNGRAYYNARFKSRVTITRDTSASTAYMELSSLRSEDTAVYYCAR SFGNYEFAYWGQGTLVTVSS.

The one-letter amino acid sequence that corresponds to SEQ ID NO: 9 is

QVQLVQSGAEVKKPGSSVKVSCKASGYLFTTYWMHWVRQAPGQGLEWMG EISPTNGRAYYNARFKSRVTITADKSTSTAYMELSSLRSEDTAVYYCAR SFGNYEFAYWGQGTLVTVSS.

The one-letter amino acid sequence that corresponds to SEQ ID NO: 10 is

QVQLVQSGAEVKKPGASVKVSCEASGYLFTTYWMHWVRQAPGQGLEWMG EISPTNGRAYYNARFKSRVTITRDTSINTAYMELSRLRSDDTAVYYCAR SFGNYEFAYWGQGTLVTVSS.

The one-letter amino acid sequence that corresponds to SEQ ID NO: 11 is

MVSSAQFLGLLLLCFQGTRCDVVMTQTPLSLPVSLGDQASISCRSRQSL VNSNGNTFLQWYLQKPGQSPKLLIYKVSLRFSGVPDRFSGSGSGTDFTL KISRVEAEDLGLYFCSQSTHVPPTFGGGTKLEIKRTVAAPSVFIFPPSD EQLKSGTASVVCLLNNFYPREAKVQWKVDNALQSGNSQESVTEQDSKDS TYSLSSTLTLSKADYEKHKVYACEVTHQGLSSPVTKSFNRGEC.

The one-letter amino acid sequence that corresponds to SEQ ID NO: 12 is

MVSSAQFLGLLLLCFQGTRCDIVMTQTPLSLPVTLGQPASISCRSRQSL VNSNGNTFLQWLQQRPGQPPRLLIYKVSLRFSGVPDRFSGSGAGTDFTL TISRVEAEDVGIYFCSQSTHVPPTFGQGTKVEIKRTVAAPSVFIFPPSD EQLKSGTASVVCLLNNFYPREAKVQWKVDNALQSGNSQESVTEQDSKDS TYSLSSTLTLSKADYEKHKVYACEVTHQGLSSPVTKSFNRGEC.

The one-letter amino acid sequence that corresponds to SEQ ID NO: 13 is

MVSSAQFLGLLLLCFQGTRCDIVMTQTPLSLSVTPGQPASISCRSRQSL VNSNGNTFLQWYLQKPGQSPQLLIYKVSLRFSGVPDRFSGSGSGTDFTL KISRVEPEDVGVYYCSQSTHVPPTFGGGTKVEVKRTVAAPSVFIFPPSD EQLKSGTASVVCLLNNFYPREAKVQWKVDNALQSGNSQESVTEQDSKDS TYSLSSTLTLSKADYEKHKVYACEVTHQGLSSPVTKSFNRGEC.

The one-letter amino acid sequence that corresponds to SEQ ID NO: 14 is

MVSSAQFLGLLLLCFQGTRCDVVMTQSPLSLPVTLGQPASISCRSRQSL VNSNGNTFLQWFQQRPGQSPRRLIYKVSLRFSGVPDRFSGSGSDTDFTL RISRVEAEDVGLYYCSQSTHVPPTFGQGTKLEIKRTVAAPSVFIFPPSD EQLKSGTASVVCLLNNFYPREAKVQWKVDNALQSGNSQESVTEQDSKDS TYSLSSTLTLSKADYEKHKVYACEVTHQGLSSPVTKSFNRGEC.

The one-letter amino acid sequence that corresponds to SEQ ID NO: 15 is

MVSSAQFLGLLLLCFQGTRCDIVMTQTPLSLSVTPGQPASISCRSRQSL VNSNGNTFLQWLLQKPGQPPQLLIYKVSLRFSGVPNRFSGSGSGTDFTL KISRVEAEDVGLYYCSQSTHVPPTFGGGTKVEIKRTVAAPSVFIFPPSD EQLKSGTASVVCLLNNFYPREAKVQWKVDNALQSGNSQESVTEQDSKDS TYSLSSTLTLSKADYEKHKVYACEVTHQGLSSPVTKSFNRGEC.

The one-letter amino acid sequence that corresponds to SEQ ID NO: 16 is

DVVMTQTPLSLPVSLGDQASISCRSRQSLVNSNGNTFLQWYLQKPGQSP KLLIYKVSLRFSGVPDRFSGSGSGTDFTLKISRVEAEDLGLYFCSQSTH VPPTFGGGTKLEIK.

The one-letter amino acid sequence that corresponds to SEQ ID NO: 17 is

DIVMTQTPLSLPVTLGQPASISCRSRQSLVNSNGNTFLQWLQQRPGQPP RLLIYKVSLRFSGVPDRFSGSGAGTDFTLTISRVEAEDVGIYFCSQSTH VPPTFGQGTKVEIK.

The one-letter amino acid sequence that corresponds to SEQ ID NO: 18 is

DIVMTQTPLSLSVTPGQPASISCRSRQSLVNSNGNTFLQWYLQKPGQSP QLLIYKVSLRFSGVPDRFSGSGSGTDFTLKISRVEPEDVGVYYCSQSTH VPPTFGGGTKVEVK.

The one-letter amino acid sequence that corresponds to SEQ ID NO: 19 is

DVVMTQSPLSLPVTLGQPASISCRSRQSLVNSNGNTFLQWFQQRPGQSP RRLIYKVSLRFSGVPDRFSGSGSDTDFTLRISRVEAEDVGLYYCSQSTH VPPTFGQGTKLEIK.

The one-letter amino acid sequence that corresponds to SEQ ID NO: 20 is

DIVMTQTPLSLSVTPGQPASISCRSRQSLVNSNGNTFLQWLLQKPGQPP
QLLIYKVSLRFSGVPNRFSGSGSGTDFTLKISRVEAEDVGLYYCSQSTH
VPPTFGGGTKVEIK.

EXAMPLES

Example 1: Affinity and Kinetics of a Commercially Available Anti-AGE Antibody The affinity and kinetics of a commercially available mouse anti-glycation end-product antibody were studied. An anti-AGE antibody raised against carboxymethyl lysine conjugated with keyhole limpet hemocyanin (Clone 318003) was obtained (R&D Systems, Inc., Minneapolis, MN; catalog no. MAB3247). Nα,Nα-bis(carboxymethyl)-L-lysine trifluoroacetate salt (Sigma-Aldrich, St. Louis, MO) was used as a model substrate for an AGE-modified protein of a cell. Label-free interaction analysis was carried out on a BIACORE™ T200 (GE Healthcare, Pittsburgh, PA), using a Series S sensor chip CM5 (GE Healthcare, Pittsburgh, PA), with Fc1 set as blank, and Fc2 immobilized with the test antibody (molecular weigh of 150,000 Da). The running buffer was a HBS-EP buffer (10 mM HEPES, 150 mM NaCl, 3 mM EDTA and 0.05% P-20, pH of 7.4), at a temperature of 25° C. Software was BIACORE™ T200 evaluation software, version 2.0. A double reference (Fc2-1 and only buffer injection), was used in the analysis, and the data was fitted to a Langmuir 1:1 binding model.

TABLE 1

Experimental set-up of affinity and kinetics analysis

| Association and dissociation | |
|---|---|
| Flow path | Fc1 and Fc2 |
| Flow rate (µl/min.) | 30 |
| Association time (s) | 300 |
| Dissociation time (s) | 300 |
| Sample concentration (µM) | 20 – 5 – 1.25 (×2) – 0.3125 – 0.078 – 0 |

FIG. 1 illustrates a graph of the antibody response versus time. The following values were determined from the analysis: $k_a$(1/Ms)=1.857×10$^3$; $k_d$ (1/s)=6.781×10$^{-3}$; $K_D$ (M)=3.651×10$^{-6}$; $R_{max}$ (RU)=19.52; and Chi$^2$=0.114. Because the Chi$^2$ value of the fitting is less than 10% of $R_{max}$, the fit is reliable.

Example 2: Transient Expression of Murine Monoclonal Anti-AGE Antibody

A murine monoclonal anti-AGE antibody was transfected in Chinese hamster ovary (CHO) cells to express and purify sufficient amount of the antibody for evaluation by enzyme-linked immunosorbent assay (ELISA) and surface plasmon resonance (SPR) analysis. DNA coding for the amino acid sequence of the antibody was synthesized. The DNA was cloned into the mammalian transient expression plasmid pD2610-v13 (DNA2.0).

Suspension-adapted CHO cells (Thermo Fisher, UK) were cultivated at 2.0-3.0×10$^5$ cells/mL at 135 rpm, 8% CO$_2$, 37° C. in ProCHO-4 serum free medium (Lonza, Belgium) supplemented with 8 mM L-glutamine (Thermo Fisher, UK) and 10 mL/L hypoxanthine/thymidine (Thermo Fisher, UK) in 500 mL vented Erlenmeyer flasks (Corning, Netherlands). Maxipreps of the construct were prepared using a PureLink® HiPure plasmid filter maxiprep kit (Thermo Fisher, UK). Vector DNA was quantified using a NanoDrop Lite spectrophotometer.

500 mL of cells at a final density of 1.0×10$^6$ cells/mL were transiently transfected with 1.25 µg/mL of vector DNA and cultured in ProCHO-5 serum free medium (Lonza, Belgium) supplemented with 8 mM L-glutamine (Invitrogen, UK) and 10 mL/L hypoxanthine/thymidine (Invitrogen, UK) in 500 mL vented Erlenmeyer flasks (Corning, Netherlands). Cultures were incubated for 8 days at 37° C., 8% CO$_2$ and 135 rpm, and routinely fed with 7.5% (v/v) Power Feed A (Sartorius, Germany) every 2-3 days before harvesting by centrifugation at 4000 rpm, 4° C. for 40 minutes. Transfection produced 612 mL of antibody.

Figure 2:
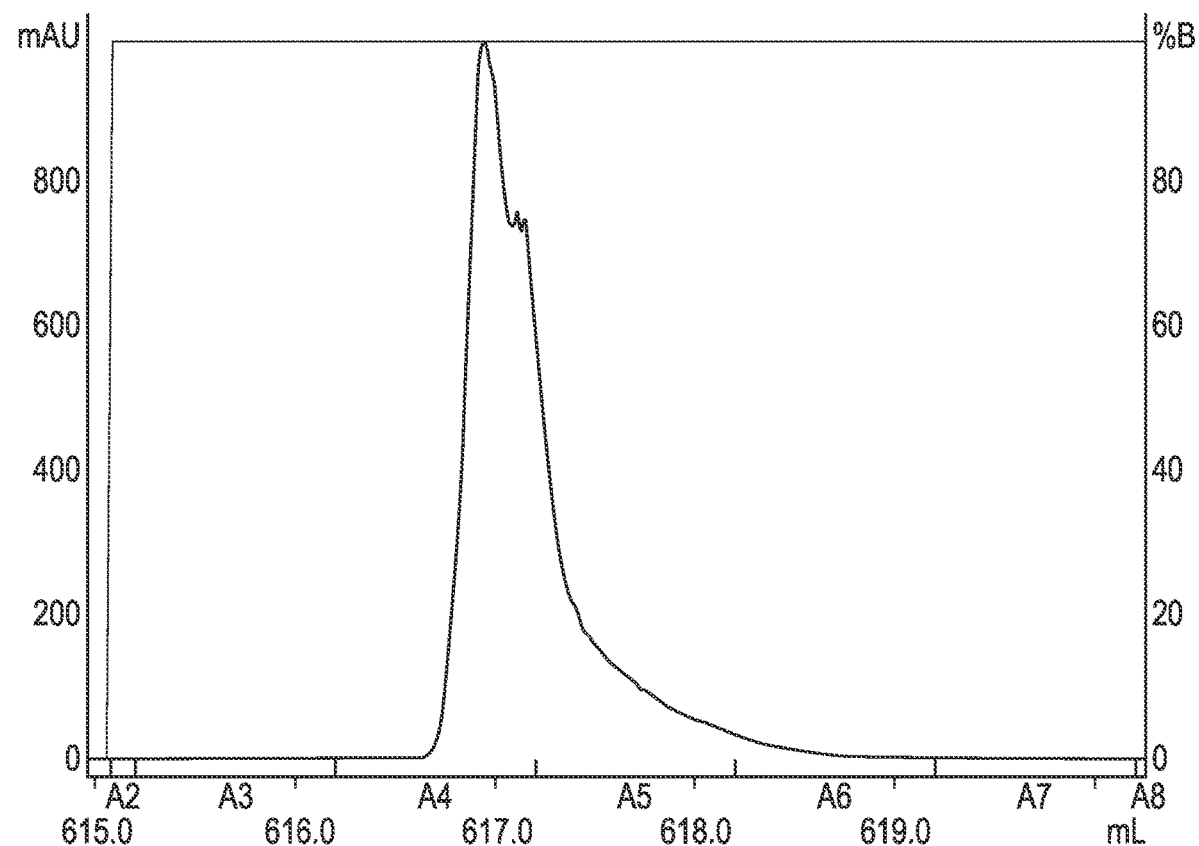
FIG. 2 illustrates a chromatogram of a transfected murine monoclonal anti-AGE antibody.

Antibody purification was performed using AKTA chromatography equipment (GE Healthcare) at room temperature (19° C.). Following centrifugation, filtered (0.22 µm) cell culture supernatant was applied to an AKTA system fitted with a 1 mL HiTrap Protein A column that was equilibrated with wash buffer. After loading, the column was washed with 20 column volumes of wash buffer. Bound antibody was step-eluted with 10 column volumes of elution buffer. FIG. 2 illustrates the chromatogram of the antibody at 280 nm. All eluted fractions were neutralized with Tris pH 9.0 buffer. Eluted fractions corresponding to elution peak were selected for overnight dialysis into PBS at 4° C.

Figure 3:
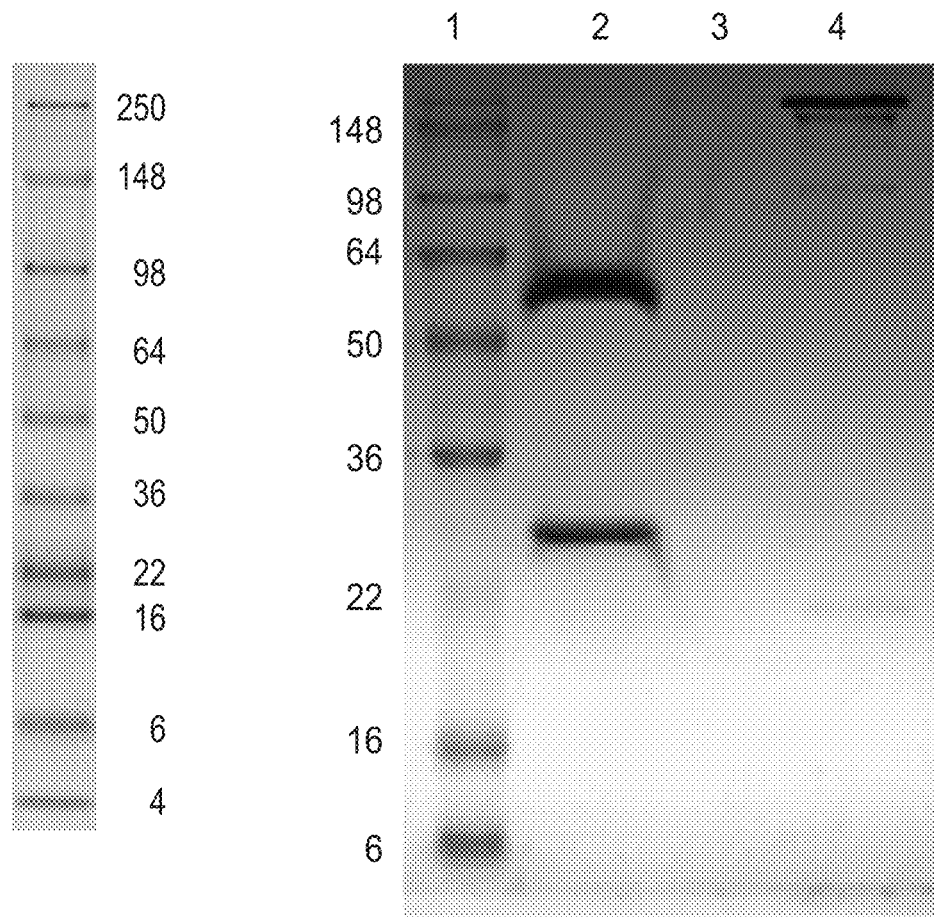
FIG. 3 illustrates a gel electropherogram of a transfected murine monoclonal anti-AGE antibody.

The purity of the antibody was evaluated using sodium dodecyl sulfate polyacrylamide gel electrophoresis (SDS-PAGE). The antibody was found to be >95% pure. FIG. 3 illustrates the gel electropherogram of the antibody. Under reducing conditions, both the heavy and the light chains of the antibody were visible and were observed at the expected molecular weights of approximately 50 and 25 kDa, respectively. Under non-reducing conditions, a single major band was observed. The lack of any major additional bands indicated an absence of antibody aggregates.

The purified antibody concentration was evaluated by spectrophotometry. The antibody was quantified with a NanoDrop Lite spectrophotometer using the extinction coefficient 205,500 M$^{-1}$ cm$^{-1}$ (or 1.0 mg/mL=A280 of 1.37 [assuming a MW=150,000 Da]) as the standard reference for IgG at A280, as per the manufacturer instructions. The 600 mL of transfected murine antibody with a concentration of 0.6 mg/mL was purified to 2.3 mL for a total yield of 1.4 mg antibody.

The binding of the transfected antibody was evaluated by ELISA. 100 ng/well of CML-OVA/N$^\varepsilon$-(Carboxymethyl) lysine-OVA (Circulex, Japan, cat. no. CY-R2053) was immobilized onto a 96 well MaxiSorp® plate in coating buffer (0.05 M NaHCO$_3$ brought to pH 9.5 by the addition of 0.05 M Na$_2$CO$_3$) at 4° C. overnight. The coating buffer was removed and the plate was washed three times with PBS Tween (PBS-T) (0.1% (v/v) Tween 20). 200 µL per well of 3% (w/v) skim milk in PBS was added to each well and agitated for 2 hours at room temperature. The plate was then washed three times with PBS-T.

The antibody was diluted from 1,000 ng/mL to 0.488 ng/mL in incubation buffer (PBS, 1% (w/v) BSA). 100 µL per well of the diluted antibody was added to the plate in triplicate and agitated for two hours at room temperature.

Figure 4:
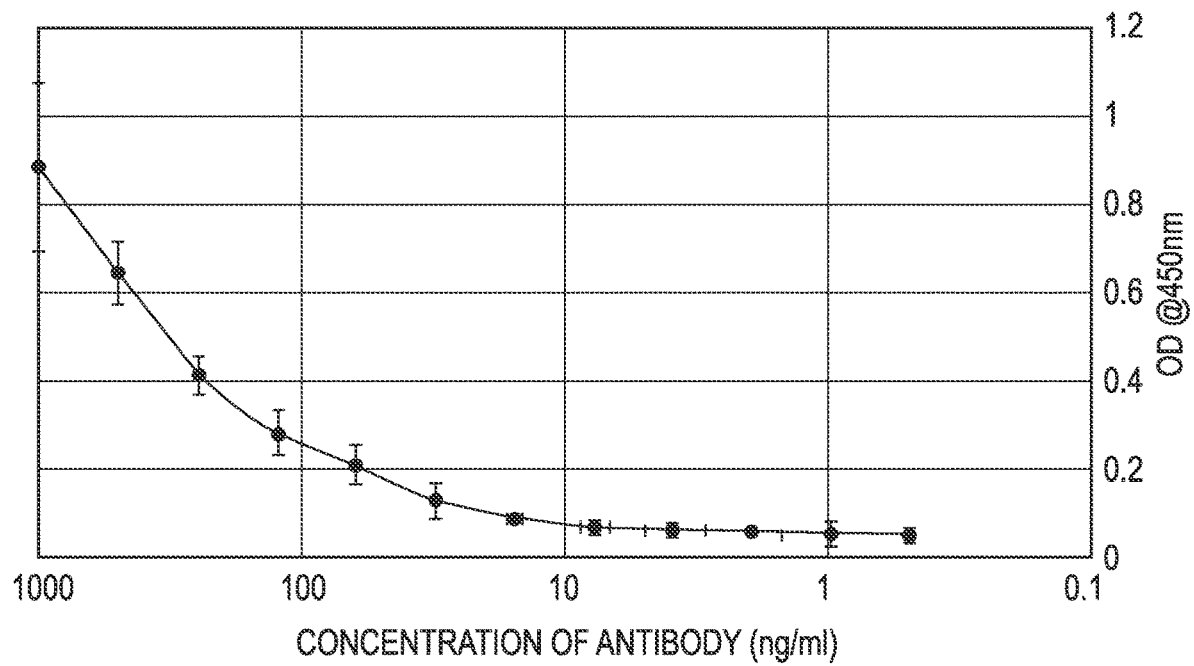
FIG. 4 illustrates the binding of a transfected murine monoclonal anti-AGE antibody to CML-OVA in an enzyme-linked immunosorbent assay.

The wells were washed three times with PBS-T. After washing, 100 µL per well goat anti mouse HRP (Fc specific) (Bio Rad, cat. no. 0300-0108P) diluted to 1:5,000 in incubation buffer was added to all wells and the plate was agitated for one hour at room temperature. The wells were washed three times with PBS-T. After washing, 100 µL of TMB substrate was added to each well and incubated at 37° C. for 10 minutes. 50 μL of 1M HCl was added to each well and the plates were immediately read at 450 nm on a Tecan Sunrise plate reader. FIG. 4 illustrates the ELISA of antibody binding to CML-OVA. The values shown in the graph are the average of triplicate readings.

The ELISA results indicate that the transfected antibody recognizes and binds to CML-OVA protein, a known AGE-modified protein. The results confirm that the antibody sequence is correct and the antibody is active. Similar results would be expected for humanized monoclonal anti-AGE antibodies that include the complementarity determining regions of these murine antibodies.

Example 3: Humanized Antibody Production

A murine anti-AGE antibody was sequenced. The amino acid sequence of the heavy chain is shown in SEQ ID NO: 1 and the amino acid sequence of the light chain is shown in SEQ ID NO: 11. The amino acid sequences of the variable domains of the heavy chain and the light chain are shown in SEQ ID NO: 6 and SEQ ID NO: 16, respectively.

CDR residues of the murine heavy chain were identified using the IMGT and the Kabat numbering systems. The closest human germline gene V-region to the murine heavy chain variable region was determined. Online databases of human IgG sequences were searched for comparison to the murine heavy chain variable domain using BLAST search algorithms, and candidate human variable domains were selected from the top 200 BLAST results. These were reduced to four candidates based on a combination of framework homology, maintaining key framework residues and canonical loop structure.

The CDRs of the murine heavy chain variable domain were grafted into the four acceptor frameworks to produce four humanized heavy chain variable domain variants. The amino acid sequences of the four humanized heavy chain variable domains are shown in SEQ ID NO: 7, SEQ ID NO: 8, SEQ ID NO: 9 and SEQ ID NO: 10. The homology of the humanized heavy chain variable domains was compared to the murine heavy chain variable domain. The results of the homology comparison are shown in Table 2 below:

TABLE 2

Heavy chain variable domain homology

| Humanized heavy chain variable domain | Identical amino acids | Consensus amino acids |
|---|---|---|
| SEQ ID NO: 7 | 82.2% | 87.3% |
| SEQ ID NO: 8 | 81.4% | 89.0% |
| SEQ ID NO: 9 | 81.4% | 90.7% |
| SEQ ID NO: 10 | 79.7% | 88.1% |

In order of homology, SEQ ID NO: 7 is the most similar to the murine heavy chain variable domain, followed by SEQ ID NO: 9, SEQ ID NO: 8 and SEQ ID NO: 10.

CDR residues of the murine light chain were identified using the IMGT and the Kabat numbering systems. The closest human germline gene V-region to the murine light chain variable region was determined. Online databases of human IgK sequences were searched for comparison to the murine light chain variable domain using BLAST search algorithms, and candidate human variable domains were selected from the top 200 BLAST results. These were reduced to four candidates based on a combination of framework homology, maintaining key framework residues and canonical loop structure.

The CDRs of the murine light chain variable domain were grafted into the four acceptor frameworks to produce four humanized light chain variable domain variants. The amino acid sequences of the four humanized light chain variable domains are shown in SEQ ID NO: 17, SEQ ID NO: 18, SEQ ID NO: 19 and SEQ ID NO: 20. The homology of the humanized light chain variable domains was compared to the murine heavy chain variable domain. The results of the homology comparison are shown in Table 3 below:

TABLE 3

Light chain variable domain homology

| Humanized light chain variable domain | Identical amino acids | Consensus amino acids |
|---|---|---|
| SEQ ID NO: 17 | 86.6% | 93.8% |
| SEQ ID NO: 18 | 88.4% | 94.6% |
| SEQ ID NO: 19 | 87.5% | 94.6% |
| SEQ ID NO: 20 | 88.4% | 92.9% |

In order of homology, SEQ ID NO: 18 is the most similar to the murine light chain variable domain, followed by SEQ ID NO: 20, SEQ ID NO: 19 and SEQ ID NO: 17.

The humanized heavy and light chain variable domain variants were checked to determine whether they had been humanized in accordance with the World Health Organization (WHO) definition of a humanized antibody. The WHO considers an antibody to be humanized if the variable region amino acid sequence is closer to human than to other species. SEQ ID NO: 7, SEQ ID NO: 8, SEQ ID NO: 9, SEQ ID NO: 10, SEQ ID NO: 17, SEQ ID NO: 18, SEQ ID NO: 19 and SEQ ID NO: 20 were assessed using the Immunogenetics Information System® (IMGT®) DomainGapAlign tool (Ehrenmann F. et al., "IMGT/3Dstructure-DB and IMGT/DomainGapAlign: a database and a tool for immunoglobulins or antibodies, T cell receptors, MHC, IgSF and MhcSF", Nucleic Acids Research, Vol. 38, D301-307). All humanized variable domains were more human than murine. Accordingly, all humanized variable domains satisfy the WHO definition of humanized antibodies.

The heavy and light chain variable domains of the murine antibody and the eight humanized heavy and light chain variant sequences were screened for MHC II binding peptides to determine if the humanization process had removed peptide sequences with high affinity using in silico algorithms. The human heavy chain germline sequences IGHV1-46 and IGHV1-3 and the human light chain germline sequences IGKV2-30 and IGKV2-29 were also analyzed for comparison. The sequences were screened for the following 8 alleles, which represent over 99% of the world's population and are the standard allele set used for prediction of MHC Class II epitopes: DRB1*01:01; DRB1*03:01; DRB1*04:01; DRB1*07:01; DRB1*08:02; DRB1*11:01; DRB1*13:02; DRB1*15:01.

The murine heavy chain variable domain had two high affinity T-cell epitope cores ($IC_{50}$<50 nM). The human germline sequence IGHV1-46 and SEQ ID NO: 7, SEQ ID NO: 9 and SEQ ID NO: 10 each had one potential T-cell epitope. The human germline sequence IGHV1-3 and SEQ ID NO: 8 each had two potential T-cell epitopes. Since it is unlikely that the human germline sequences would be immunogenic, the potential T-cell epitopes may be an over-prediction of the MHC Class II epitope software. The potential T-cell epitopes are more likely regulatory T-cell epitopes, which would be beneficial to the sequences.

The murine light chain variable domain and SEQ ID NO: 17, SEQ ID NO: 18, SEQ ID NO: 19 and SEQ ID NO: 20 each had two high affinity T-cell epitope cores ($IC_{50}$<50 nM) and one potential T-cell epitope. The human germline sequence IGKV2-30 had no potential T-cell epitopes. The human germline sequence IGKV2-29 had two potential T-cell epitopes. As in the heavy chain variable sequences, the potential T-cell epitopes may be an over-prediction of the MHC Class II epitope software but are more likely beneficial regulatory T-cell epitopes.

Post-translational modifications of the murine and humanized antibodies were studied. The N-linked glycosylation motif NXS/T, where X is any amino acid except proline, was not present in the any of the variable domains. The sequences were also analyzed for the presence of the amino acid motifs SNG, ENN, LNG and LNN, which can be prone to deamidation of asparagines to aspartic acid. The motif SNG was present in the CDR1 of all of the light chains. Although this motif is potentially immunogenic, no substitutions were made since it only occurred in the CDR.

Murine heavy chain and light chain signal peptides were identified. These signal peptides may result in higher levels of expression in Chinese hamster ovary (CHO) cells. The heavy chain signal peptide is included in the murine heavy chain (SEQ ID NO: 1) and the four humanized heavy chains (SEQ ID NO: 2, SEQ ID NO: 3, SEQ ID NO: 4 and SEQ ID NO: 5). The light chain signal peptide is included in the murine light chain (SEQ ID NO: 11) and the four humanized light chains (SEQ ID NO: 12, SEQ ID NO: 13, SEQ ID NO: 14 and SEQ ID NO: 15).

The structures of the variable domain binding sites were modeled using DNASTAR NovaFold, a protein structure prediction software based on I-Tasser. NovaFold utilizes the I-Tasser algorithms that combine threading and ab initio folding technologies to build accurate, full 3D atomic models of proteins with previously unknown structures. Analysis of the protein structures indicated that the combinations of the heavy chain and light variable domains SEQ ID NO: 7-SEQ ID NO: 17, SEQ ID NO: 7-SEQ ID NO: 18, SEQ ID NO: 8-SEQ ID NO: 20 and SEQ ID NO: 9-SEQ ID NO: 18 appear to have the closest structure to the combination of the murine heavy chain and light chain variable domains SEQ ID NO: 5-SEQ ID NO:16. In general, the humanized variants containing the light chain variable domain having the sequence shown in SEQ ID NO: 18 had better structures than those containing other light chain variable domains. Similarly, the humanized variants containing the heavy chain variable domain having the sequence shown in SEQ ID NO: 7 had better structures than those containing other heavy chain variable domains.

Example 4 (Prophetic): Future Antibody Studies

Each of the heavy chain variable domains (SEQ ID NO: 7, SEQ ID NO: 8, SEQ ID NO: 9 and SEQ ID NO: 10) is synthesized in-frame with a human IgG1 isotype constant domain sequence. The entire heavy chain sequence is codon optimized (DNA2.0, USA) and the DNA sequence is verified. The amino acid sequence of the IgG1 constant domain (allotype G1m17,1) is shown below:

ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV

EPKSCDKTHTCPPCPAPELLGGPSVFLFPPKPKDTLMISRTPEVTCVWV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPGK

Each of the light chain variable domains (SEQ ID NO: 17, SEQ ID NO: 18, SEQ ID NO: 19 and SEQ ID NO: 20) is synthesized in-frame with a human IgK isotype constant domain sequence. The entire light chain sequence is codon optimized (DNA2.0, USA) and the DNA sequence is verified. The amino acid sequence of the IgK constant domain (allotype Km3) is shown below:

TVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVT

KSFNRGEC

Each of the variant chains is verified by DNA sequencing analysis. Next, transient transfection and expression of each of the humanized antibodies is carried out. One chimeric antibody is expressed for use as a positive control and contains the murine variable domains and the human Ig constant domains. Sixteen humanized variants are expressed that contain the humanized heavy chain and light chain variable domains and the human Ig constant domains as shown in Table 4 below:

TABLE 4

Chimeric and humanized antibody variant combinations

| Chimeric Antibody | SEQ ID NO: 6-SEQ ID NO: 16 | | | |
|---|---|---|---|---|
| Humanized Variants | SEQ ID NO: 7-<br>SEQ ID NO: 17 | SEQ ID NO: 7-<br>SEQ ID NO: 18 | SEQ ID NO: 7-<br>SEQ ID NO: 19 | SEQ ID NO: 7-<br>SEQ ID NO: 20 |
| | SEQ ID NO: 8-<br>SEQ ID NO: 17 | SEQ ID NO: 8-<br>SEQ ID NO: 18 | SEQ ID NO: 8-<br>SEQ ID NO: 19 | SEQ ID NO: 8-<br>SEQ ID NO: 20 |
| | SEQ ID NO: 9-<br>SEQ ID NO: 17 | SEQ ID NO: 9-<br>SEQ ID NO: 18 | SEQ ID NO: 9-<br>SEQ ID NO: 19 | SEQ ID NO: 9-<br>SEQ ID NO: 20 |
| | SEQ ID NO: 10-<br>SEQ ID NO: 17 | SEQ ID NO: 10-<br>SEQ ID NO: 18 | SEQ ID NO: 10-<br>SEQ ID NO: 19 | SEQ ID NO: 10-<br>SEQ ID NO: 20 |

Example 5 (Prophetic): Treatment of Sarcopenia

An elderly patient is diagnosed with sarcopenia. She is administered a humanized monoclonal anti-AGE antibody having a heavy chain with 99% sequence identity to SEQ ID NO: 2 and a light chain with 99% sequence identity to SEQ ID NO: 12. The antibody is administered intravenously at a dose of 5 mg/kg once per week. The antibody specifically targets and kills cells expressing cell-surface advanced glycation end-products, such as senescent cells. The efficacy of treatment is determined by measuring the patient's levels of $p16^{INK4a}$ before and after administration of the antibody. The patient does not develop an immune response to the antibody. The patient's sarcopenia improves as evidenced by an increase in muscle mass.

Example 6 (Prophetic): Treatment of Osteoarthritis

A patient is diagnosed with osteoarthritis. He is administered a composition comprising a pharmaceutically acceptable carrier and a humanized monoclonal anti-AGE antibody having a heavy chain variable sequence with 98% sequence identity to SEQ ID NO: 7 and a light chain variable region with 98% sequence identity to SEQ ID NO: 18. The antibody is administered orally at a dose of 10 mg/kg once per day. The antibody specifically targets and kills cells expressing cell-surface advanced glycation end-products, such as senescent chondrocytes. The efficacy of treatment is determined by measuring the patient's levels of $p16^{INK4}a$ before and after administration of the composition. The patient does not develop an immune response to the composition containing the antibody. The patient's osteoarthritis improves as evidenced by a decrease in joint pain.

REFERENCES

1. International Application Pub. No. WO 2009/143411 to Gruber (26 Nov. 2009).
2. U.S. Pat. No. 5,702,704 to Bucala (issued Dec. 30, 1997).
3. U.S. Pat. No. 6,380,165 to Al-Abed et al. (issued Apr. 30, 2002).
4. U.S. Pat. No. 6,387,373 to Wright et al. (issued May 14, 2002).
5. U.S. Pat. No. 4,217,344 to Vanlerberghe et al. (issued Aug. 12, 1980).
6. U.S. Pat. No. 4,917,951 to Wallach (issued Apr. 17, 1990).
7. U.S. Pat. No. 4,911,928 to Wallach (issued Mar. 27, 1990).
8. U.S. Patent Application Publication Pub. No. US 2010/226932 to Smith et al. (Sep. 9, 2010).
9. Ando K, et al., "Membrane Proteins of Human Erythrocytes Are Modified by Advanced Glycation End Products During Aging in the Circulation," *Biochemical and Biophysical Research Communications*, Vol. 258, 123-27 (1999).
10. Lindsey J B, et al., "Receptor For Advanced Glycation End-Products (RAGE) and soluble RAGE (sRAGE): Cardiovascular Implications," *Diabetes Vascular Disease Research*, Vol. 6(1), 7-14, (2009).
11. Bierhaus A, "AGEs and their interaction with AGE-receptors in vascular disease and diabetes mellitus. I. The AGE concept," Cardiovasc Res, Vol. 37(3), 586-600 (1998).
12. Meuter A., et al. "Markers of cellular senescence are elevated in murine blastocysts cultured in vitro: molecular consequences of culture in atmospheric oxygen" J Assist Reprod Genet. 2014 Aug. 10. [Epub ahead of print].
13. Baker, D. J. et al., "Clearance of p16Ink4a-positive senescent cells delays ageing-associated disorders", Nature, vol. 479, pp. 232-236, (2011).
14. Jana Hadrabove, et al. "Chicken immunoglobulins for prophylaxis: Effect of inhaled antibodies on inflammatory parameters in rat airways" Journal of Applied Biomedicine (in press; Available online 5 May 2014).
15. Vlassara, H. et al., "High-affinity-receptor-mediated Uptake and Degradation of Glucose-modified Proteins: A Potential Mechanism for the Removal of Senescent Macromolecules", *Proc. Natl. Acad. Sci. USA*, Vol. 82, 5588, 5591 (1985).
16. Roll, P. et al., "Anti-CD20 Therapy in Patients with Rheumatoid Arthritis", *Arthritis & Rheumatism*, Vol. 58, No. 6, 1566-1575 (2008).
17. Kajstura, J. et al., "Myocyte Turnover in the Aging Human Heart", *Circ. Res.*, Vol. 107(11), 1374-86, (2010).
18. de Groot, K. et al., "Vascular Endothelial Damage and Repair in Antineutrophil Cytoplasmic Antibody-Associated Vasculitis", *Arthritis and Rheumatism*, Vol. 56(11), 3847, 3847 (2007).
19. Manesso, E. et al., "Dynamics of β-Cell Turnover: Evidence for β-Cell Turnover and Regeneration from Sources of β-Cells other than β-cell Replication in the HIP Rat", *Am. J. Physiol. Endocrinol. Metab.*, Vol. 297, E323, E324 (2009).
20. Kirstein, M. et al., "Receptor-specific Induction of Insulin-like Growth Factor I in Human Monocytes by Advanced Glycosylation End Product-modified Proteins", *J. Clin. Invest.*, Vol. 90, 439, 439-440 (1992).
21. Murphy, J. F., "Trends in cancer immunotherapy", *Clinical Medical Insights: Oncology*, Vol. 14(4), 67-80 (2010).
22. Virella, G. et al., "Autoimmune Response to Advanced Glycosylation End-Products of Human LDL", *Journal of Lipid Research*, Vol. 44, 487-493 (2003).
23. Ameli, S. et al., "Effect of Immunization With Homologous LDL and Oxidized LDL on Early Atherosclerosis in Hypercholesterolemic Rabbits", Arteriosclerosis, Thrombosis, and Vascular Biology, Vol. 16, 1074 (1996).
24. "Sarcopenia", available online at en.wikipedia.org/wiki/Sarcopenia (Nov. 14, 2014).
25. "What is sarcopenia?", available online at www.iofbonehealth.org/what-sarcopenia (2014).
26. Blahd, W., "Sarcopenia with aging", available online at www.webmd.com/healthy-aging/sarcopenia-with-aging (Aug. 3, 2014).
27. "Keyhole limpet hemocyanin", available online at en.wikipedia.org/wiki/Keyhole_limpet_hemocyanin (Apr. 18, 2014).
28. "CML-BSA Product Data Sheet", available online at www.cellbiolabs.com/sites/default/files/STA-314-cml-bsa.pdf (2010).
29. "CML (N-epsilon-(Carboxymethyl)Lysine) Assays and Reagents", available online at www.cellbiolabs.com/cml-assays (Accessed on Dec. 15, 2014).
30. Cruz-Jentoft, A. J. et al., "Sarcopenia: European consensus on definition and diagnosis", *Age and Ageing*, Vol. 39, pp. 412-423 (Apr. 13, 2010).
31. Rolland, Y. et al., "Sarcopenia: its assessment, etiology, pathogenesis, consequences and future perspectives", *J. Nutr. Health Aging*, Vol. 12(7), pp. 433-450 (2008).
32. Mera, K. et al., "An autoantibody against $N^\varepsilon$-(carboxyethyl)lysine (CEL): Possible involvement in the removal of CEL-modified proteins by macrophages", *Biochemical and Biophysical Research Communications*, Vol. 407, pp. 420-425 (Mar. 12, 2011).

33. Reddy, S. et al., "Nᵉ-(carboxymethyl)lysine is a dominant advanced glycation end product (AGE) antigen in tissue proteins", *Biochemistry*, Vol. 34, pp. 10872-10878 (Aug. 1, 1995).
34. Naylor, R. M. et al., "Senescent cells: a novel therapeutic target for aging and age-related diseases", *Clinical Pharmacology & Therapeutics*, Vol. 93(1), pp. 105-116 (Dec. 5, 2012).
35. Katcher, H. L., "Studies that shed new light on aging", *Biochemistry (Moscow)*, Vol. 78(9), pp. 1061-1070 (2013).
36. Ahmed, E. K. et al., "Protein Modification and Replicative Senescence of WI-38 Human Embryonic Fibroblasts", *Aging Cells*, Vol. 9, 252, 260 (2010).
37. Vlassara, H. et al., "Advanced Glycosylation Endproducts on Erythrocyte Cell Surface Induce Receptor-Mediated Phagocytosis by Macrophages", *J. Exp. Med.*, Vol. 166, 539, 545 (1987).
38. Fielding, R. A., et al., "Sarcopenia: an undiagnosed condition in older adults. Current consensus definition: prevalence, etiology, and consequences", *Journal of the American Medical Directors Association*, Vol. 12(4), pp. 249-256 (May 2011).
39. Maass, D. R. et al., "Alpaca (*Lama pacos*) as a convenient source of recombinant camelid heavy chain antibodies (VHHs)", Journal of Immunological Methods, Vol. 324, No. 1-2, pp. 13-25 (Jul. 31, 2007).
40. Strietzel, C. J. et al., "In vitro functional characterization of feline IgGs", Veterinary Immunology and Immunopathology, Vol. 158, pp. 214-223 (2014).
41. Patel, M. et al., "Sequence of the dog immunoglobulin alpha and epsilon constant region genes", Immunogenetics, Vol. 41, pp. 282-286 (1995).
42. Wagner, B. et al., "The complete map of the Ig heavy chain constant gene region reveals evidence for seven IgG isotypes and for IgD in the horse", The Journal of Immunology, Vol. 173, pp. 3230-3242 (2004).
43. Hamers-Casterman, C. et al., "Naturally occurring antibodies devoid of light chains", Nature, Vol. 363, pp. 446-448 (Jun. 3, 1993).
44. De Genst, E. et al., "Antibody repertoire development in camelids", Developmental & Comparative Immunology, Vol. 30, pp. 187-198 (available online Jul. 11, 2005).
45. Griffin, L. M. et al., "Analysis of heavy and light chain sequences of conventional camelid antibodies from *Camelus dromedarius* and *Camelus bactrianus* species", Journal of Immunological Methods, Vol. 405, pp. 35-46 (available online Jan. 18, 2014).
46. Nguyen, V. K. et al., "Camel heavy-chain antibodies: diverse germline $V_H$H and specific mechanisms enlarge the antigen-binding repertoire", The European Molecular Biology Organization Journal, Vol. 19, No, 5, pp. 921-930 (2000).
47. Muyldermans, S. et al., "Sequence and structure of $V_H$ domain from naturally occurring camel heavy chain immunoglobulins lacking light chains", Protein Engineering, Vol. 7, No. 9, pp. 1129-1135 (1994).
48. Glover, A., "Of mice and men", European Biopharmaceutical Review, Winter 2016, 4 pages (January 2016).
49. "The basic guide to magnetic bead cell separation", Sepmag, available online at www.sepmag.eu/free-basic-guide-magnetic-bead-cell-separation (downloaded Apr. 12, 2017).

What is claimed is:

1. A method of treating cancer in a human subject, comprising:
   administering to the subject a composition comprising a humanized monoclonal advanced glycation end-product antibody, and
   a pharmaceutically acceptable carrier,
   wherein the antibody binds a carboxymethyllysine-modified protein or peptide.

2. The method of claim 1, wherein the antibody comprises a heavy chain comprising an amino acid sequence having at least 90% sequence identity with at least one amino acid sequence selected from the group consisting of SEQ ID NO: 2, SEQ ID NO: 3, SEQ ID NO: 4 and SEQ ID NO: 5, and
   a light chain comprising an amino acid sequence having at least 90% sequence identity with at least one amino acid sequence selected from the group consisting of SEQ ID NO: 12, SEQ ID NO: 13, SEQ ID NO: 14 and SEQ ID NO: 15.

3. The method of claim 1, wherein the antibody comprises,
   a heavy chain, having a heavy chain variable region, and
   a light chain, having a light chain variable region,
   wherein the heavy chain variable region comprises an amino acid sequence having at least 90% sequence identity with at least one amino acid sequence selected from the group consisting of SEQ ID NO: 7, SEQ ID NO: 8, SEQ ID NO: 9 and SEQ ID NO: 10, and
   the light chain variable region comprises an amino acid sequence having at least 90% sequence identity with at least one amino acid sequence selected from the group consisting of SEQ ID NO: 17, SEQ ID NO: 18, SEQ ID NO: 19 and SEQ ID NO: 20.

4. The method of claim 1, wherein the cancer is selected from the group consisting of breast cancer, triple negative breast cancer, lung cancer, melanoma, colon cancer, renal cell carcinoma, cancer of the cervix, bladder cancer, rectal cancer, esophageal cancer, liver cancer, mouth and throat cancer, multiple myeloma, ovarian cancer, stomach cancer and retinal blastoma cancers.

5. The method of claim 1, wherein the antibody is substantially non-immunogenic to humans.

6. The method of claim 1, wherein the antibody has a rate of dissociation ($k_d$) of at most $6 \times 10^{-3}$ ($sec^{-1}$).

7. The method of claim 1, wherein the antibody, comprises
a heavy chain, having a heavy chain variable region, and a light chain, having a light chain variable region,
wherein the heavy chain variable region comprises an amino acid sequence selected from the group consisting of SEQ ID NO: 7, SEQ ID NO: 8, SEQ ID NO: 9 and SEQ ID NO: 10, and
the light chain variable region comprises an amino acid sequence selected from the group consisting of SEQ ID NO: 17, SEQ ID NO: 18, SEQ ID NO: 19 and SEQ ID NO: 20.

8. The method of claim 1, further comprising:
testing the subject for effectiveness of the administration at treating the cancer,
followed by repeating the administering of the antibody.

9. The method of claim 1, wherein the antibody is conjugated to an agent that causes the destruction of AGE-modified cells.

10. The method of claim 9, wherein the agent comprises at least one member selected from the group consisting of toxins, cytotoxic agents, magnetic nanoparticles and magnetic spin-vortex discs.

11. The method of claim 1, wherein the composition is in unit dosage form.

12. The method of claim 1, wherein the composition is in the form of a solution or suspension, for parenteral administration.

13. The method of claim 1, wherein the humanized monoclonal advanced glycation end-product antibody, comprises
a heavy chain, and
a light chain,
wherein the heavy chain comprises an amino acid sequence selected from the group consisting of SEQ ID NO: 2, SEQ ID NO: 3, SEQ ID NO: 4 and SEQ ID NO: 5, and
the light chain comprises an amino acid sequence selected from the group consisting of SEQ ID NO: 12, SEQ ID NO: 13, SEQ ID NO: 14 and SEQ ID NO: 15.

14. The method of claim 1, wherein the composition is sterile.

* * * * *

SEQUENCE LISTING

```
Sequence total quantity: 20
SEQ ID NO: 1            moltype = AA  length = 467
FEATURE                 Location/Qualifiers
source                  1..467
                        mol_type = protein
                        organism = Mus musculus
SEQUENCE: 1
MGWTLVFLFL LSVTAGVHSQ VQLLQPGAEL VKPGASVKLA CKASGYLFTT YWMHWLKQRP   60
GQGLEWIGEI SPTNGRAYYN ARFKSEATLT VDKSSNTAYM QLSSLTSEAS AVYYCARSFG  120
NYEFAYWGQG TLVTVSVAST KGPSVFPLAP SSKSTSGGTA ALGCLVKDYF PEPVTVSWNS  180
GALTSGVHTF PAVLQSSGLY SLSSVVTVPS SSLGTQTYIC NVNHKPSNTK VDKKVEPKSC  240
DKTHTCPPCP APELLGGPSV FLFPPKPKDT LMISRTPEVT CVVVDVSHED PEVKFNWYVD  300
GVEVHNAKTK PREEQYNSTY RVVSVLTVLH QDWLNGKEYK CKVSNKALPA PIEKTISKAK  360
GQPREPQVYT LPPSRDELTK NQVSLTCLVK GFYPSDIAVE WESNGQPENN YKTTPPVLDS  420
DGSFFLYSKL TVDKSRWQQG NVFSCSVMHE ALHNHYTQKS LSLSPGK               467

SEQ ID NO: 2            moltype = AA  length = 467
FEATURE                 Location/Qualifiers
source                  1..467
                        mol_type = protein
                        organism = synthetic construct
REGION                  1..467
                        note = Humanized heavy chain
SEQUENCE: 2
MGWTLVFLFL LSVTAGVHSE VQLLESGAEA KKPGASVKLS CKASGYLFTT YWMHWVHQAP   60
GQRLEWMGEI SPTNGRAYYN ARFKSRVTIT VDKSASTAYM ELSSLRSEDT AVYYCARSFG  120
NYEFAYWGQG TLVTVSSAST KGPSVFPLAP SSKSTSGGTA ALGCLVKDYF PEPVTVSWNS  180
GALTSGVHTF PAVLQSSGLY SLSSVVTVPS SSLGTQTYIC NVNHKPSNTK VDKKVEPKSC  240
DKTHTCPPCP APELLGGPSV FLFPPKPKDT LMISRTPEVT CVVVDVSHED PEVKFNWYVD  300
GVEVHNAKTK PREEQYNSTY RVVSVLTVLH QDWLNGKEYK CKVSNKALPA PIEKTISKAK  360
GQPREPQVYT LPPSRDELTK NQVSLTCLVK GFYPSDIAVE WESNGQPENN YKTTPPVLDS  420
DGSFFLYSKL TVDKSRWQQG NVFSCSVMHE ALHNHYTQKS LSLSPGK               467

SEQ ID NO: 3            moltype = AA  length = 467
FEATURE                 Location/Qualifiers
source                  1..467
                        mol_type = protein
```

```
                              organism = synthetic construct
REGION                        1..467
                              note = Humanized heavy chain
SEQUENCE: 3
MGWTLVFLFL LSVTAGVHSQ VQLVQSGAEV KKPGASVKVS CKASGYLFTT YWMHWVRQAP  60
GQRLEWIGEI SPTNGRAYYN ARFKSRVTIT RDTSASTAYM ELSSLRSEDT AVYYCARSFG 120
NYEFAYWGQG TLVTVSSAST KGPSVFPLAP SSKSTSGGTA ALGCLVKDYF PEPVTVSWNS 180
GALTSGVHTF PAVLQSSGLY SLSSVVTVPS SSLGTQTYIC NVNHKPSNTK VDKKVEPKSC 240
DKTHTCPPCP APELLGGPSV FLFPPKPKDT LMISRTPEVT CVVVDVSHED PEVKFNWYVD 300
GVEVHNAKTK PREEQYNSTY RVVSVLTVLH QDWLNGKEYK CKVSNKALPA PIEKTISKAK 360
GQPREPQVYT LPPSRDELTK NQVSLTCLVK GFYPSDIAVE WESNGQPENN YKTTPPVLDS 420
DGSFFLYSKL TVDKSRWQQG NVFSCSVMHE ALHNHYTQKS LSLSPGK            467

SEQ ID NO: 4                  moltype = AA   length = 467
FEATURE                       Location/Qualifiers
source                        1..467
                              mol_type = protein
                              organism = synthetic construct
REGION                        1..467
                              note = Humanized heavy chain
SEQUENCE: 4
MGWTLVFLFL LSVTAGVHSQ VQLVQSGAEV KKPGSSVKVS CKASGYLFTT YWMHWVRQAP  60
GQGLEWMGEI SPTNGRAYYN ARFKSRVTIT ADKSTSTAYM ELSSLRSEDT AVYYCARSFG 120
NYEFAYWGQG TLVTVSSAST KGPSVFPLAP SSKSTSGGTA ALGCLVKDYF PEPVTVSWNS 180
GALTSGVHTF PAVLQSSGLY SLSSVVTVPS SSLGTQTYIC NVNHKPSNTK VDKKVEPKSC 240
DKTHTCPPCP APELLGGPSV FLFPPKPKDT LMISRTPEVT CVVVDVSHED PEVKFNWYVD 300
GVEVHNAKTK PREEQYNSTY RVVSVLTVLH QDWLNGKEYK CKVSNKALPA PIEKTISKAK 360
GQPREPQVYT LPPSRDELTK NQVSLTCLVK GFYPSDIAVE WESNGQPENN YKTTPPVLDS 420
DGSFFLYSKL TVDKSRWQQG NVFSCSVMHE ALHNHYTQKS LSLSPGK            467

SEQ ID NO: 5                  moltype = AA   length = 467
FEATURE                       Location/Qualifiers
source                        1..467
                              mol_type = protein
                              organism = synthetic construct
REGION                        1..467
                              note = Humanized heavy chain
SEQUENCE: 5
MGWTLVFLFL LSVTAGVHSQ VQLVQSGAEV KKPGASVKVS CEASGYLFTT YWMHWVRQAP  60
GQGLEWMGEI SPTNGRAYYN ARFKSRVTIT RDTSINTAYM ELSRLRSDDT AVYYCARSFG 120
NYEFAYWGQG TLVTVSSAST KGPSVFPLAP SSKSTSGGTA ALGCLVKDYF PEPVTVSWNS 180
GALTSGVHTF PAVLQSSGLY SLSSVVTVPS SSLGTQTYIC NVNHKPSNTK VDKKVEPKSC 240
DKTHTCPPCP APELLGGPSV FLFPPKPKDT LMISRTPEVT CVVVDVSHED PEVKFNWYVD 300
GVEVHNAKTK PREEQYNSTY RVVSVLTVLH QDWLNGKEYK CKVSNKALPA PIEKTISKAK 360
GQPREPQVYT LPPSRDELTK NQVSLTCLVK GFYPSDIAVE WESNGQPENN YKTTPPVLDS 420
DGSFFLYSKL TVDKSRWQQG NVFSCSVMHE ALHNHYTQKS LSLSPGK            467

SEQ ID NO: 6                  moltype = AA   length = 118
FEATURE                       Location/Qualifiers
source                        1..118
                              mol_type = protein
                              organism = Mus musculus
SEQUENCE: 6
QVQLLQPGAE LVKPGASVKL ACKASGYLFT TYWMHWLKQR PGQGLEWIGE ISPTNGRAYY  60
NARFKSEATL TVDKSSNTAY MQLSSLTSEA SAVYYCARSF GNYEFAYWGQ GTLVTVSV   118

SEQ ID NO: 7                  moltype = AA   length = 118
FEATURE                       Location/Qualifiers
source                        1..118
                              mol_type = protein
                              organism = synthetic construct
REGION                        1..118
                              note = Humanized heavy chain variable region
SEQUENCE: 7
EVQLLESGAE AKKPGASVKL SCKASGYLFT TYWMHWVHQA PGQRLEWMGE ISPTNGRAYY  60
NARFKSRVTI TVDKSASTAY MELSSLRSED TAVYYCARSF GNYEFAYWGQ GTLVTVSS   118

SEQ ID NO: 8                  moltype = AA   length = 118
FEATURE                       Location/Qualifiers
source                        1..118
                              mol_type = protein
                              organism = synthetic construct
REGION                        1..118
                              note = Humanized heavy chain variable region
SEQUENCE: 8
QVQLVQSGAE VKKPGASVKV SCKASGYLFT TYWMHWVRQA PGQRLEWIGE ISPTNGRAYY  60
NARFKSRVTI TRDTSASTAY MELSSLRSED TAVYYCARSF GNYEFAYWGQ GTLVTVSS   118

SEQ ID NO: 9                  moltype = AA   length = 118
```

```
FEATURE                 Location/Qualifiers
source                  1..118
                        mol_type = protein
                        organism = synthetic construct
REGION                  1..118
                        note = Humanized heavy chain variable region
SEQUENCE: 9
QVQLVQSGAE VKKPGSSVKV SCKASGYLFT TYWMHWVRQA PGQGLEWMGE ISPTNGRAYY    60
NARFKSRVTI TADKSTSTAY MELSSLRSED TAVYYCARSF GNYEFAYWGQ GTLVTVSS    118

SEQ ID NO: 10           moltype = AA   length = 118
FEATURE                 Location/Qualifiers
source                  1..118
                        mol_type = protein
                        organism = synthetic construct
REGION                  1..118
                        note = Humanized heavy chain variable region
SEQUENCE: 10
QVQLVQSGAE VKKPGASVKV SCEASGYLFT TYWMHWVRQA PGQGLEWMGE ISPTNGRAYY    60
NARFKSRVTI TRDTSINTAY MELSRLRSDD TAVYYCARSF GNYEFAYWGQ GTLVTVSS    118

SEQ ID NO: 11           moltype = AA   length = 239
FEATURE                 Location/Qualifiers
source                  1..239
                        mol_type = protein
                        organism = Mus musculus
SEQUENCE: 11
MVSSAQFLGL LLLCFQGTRC DVVMTQTPLS LPVSLGDQAS ISCRSRQSLV NSNGNTFLQW    60
YLQKPGQSPK LLIYKVSLRF SGVPDRFSGS GSGTDFTLKI SRVEAEDLGL YFCSQSTHVP   120
PTFGGGTKLE IKRTVAAPSV FIFPPSDEQL KSGTASVVCL LNNFYPREAK VQWKVDNALQ   180
SGNSQESVTE QDSKDSTYSL SSTLTLSKAD YEKHKVYACE VTHQGLSSPV TKSFNRGEC    239

SEQ ID NO: 12           moltype = AA   length = 239
FEATURE                 Location/Qualifiers
source                  1..239
                        mol_type = protein
                        organism = synthetic construct
REGION                  1..239
                        note = Humanized light chain
SEQUENCE: 12
MVSSAQFLGL LLLCFQGTRC DIVMTQTPLS LPVTLGQPAS ISCRSRQSLV NSNGNTFLQW    60
LQQRPGQPPR LLIYKVSLRF SGVPDRFSGS GAGTDFTLTI SRVEAEDVGI YFCSQSTHVP   120
PTFGQGTKVE IKRTVAAPSV FIFPPSDEQL KSGTASVVCL LNNFYPREAK VQWKVDNALQ   180
SGNSQESVTE QDSKDSTYSL SSTLTLSKAD YEKHKVYACE VTHQGLSSPV TKSFNRGEC    239

SEQ ID NO: 13           moltype = AA   length = 239
FEATURE                 Location/Qualifiers
source                  1..239
                        mol_type = protein
                        organism = synthetic construct
REGION                  1..239
                        note = Humanized light chain
SEQUENCE: 13
MVSSAQFLGL LLLCFQGTRC DIVMTQTPLS LSVTPGQPAS ISCRSRQSLV NSNGNTFLQW    60
YLQKPGQSPQ LLIYKVSLRF SGVPDRFSGS GSGTDFTLRI SRVEPEDVGV YYCSQSTHVP   120
PTFGGGTKVE VKRTVAAPSV FIFPPSDEQL KSGTASVVCL LNNFYPREAK VQWKVDNALQ   180
SGNSQESVTE QDSKDSTYSL SSTLTLSKAD YEKHKVYACE VTHQGLSSPV TKSFNRGEC    239

SEQ ID NO: 14           moltype = AA   length = 239
FEATURE                 Location/Qualifiers
source                  1..239
                        mol_type = protein
                        organism = synthetic construct
REGION                  1..239
                        note = Humanized light chain
SEQUENCE: 14
MVSSAQFLGL LLLCFQGTRC DVVMTQSPLS LPVTLGQPAS ISCRSRQSLV NSNGNTFLQW    60
FQQRPGQSPR RLIYKVSLRF SGVPDRFSGS GSDTDFTLRI SRVEAEDVGL YYCSQSTHVP   120
PTFGQGTKLE IKRTVAAPSV FIFPPSDEQL KSGTASVVCL LNNFYPREAK VQWKVDNALQ   180
SGNSQESVTE QDSKDSTYSL SSTLTLSKAD YEKHKVYACE VTHQGLSSPV TKSFNRGEC    239

SEQ ID NO: 15           moltype = AA   length = 239
FEATURE                 Location/Qualifiers
source                  1..239
                        mol_type = protein
                        organism = synthetic construct
REGION                  1..239
                        note = Humanized light chain
SEQUENCE: 15
```

```
MVSSAQFLGL LLLCFQGTRC DIVMTQTPLS LSVTPGQPAS ISCRSRQSLV NSNGNTFLQW     60
LLQKPGQPPQ LLIYKVSLRF SGVPNRFSGS GSGTDFTLKI SRVEAEDVGL YYCSQSTHVP    120
PTFGGGTKVE IKRTVAAPSV FIFPPSDEQL KSGTASVVCL LNNFYPREAK VQWKVDNALQ    180
SGNSQESVTE QDSKDSTYSL SSTLTLSKAD YEKHKVYACE VTHQGLSSPV TKSFNRGEC     239

SEQ ID NO: 16           moltype = AA  length = 112
FEATURE                 Location/Qualifiers
source                  1..112
                        mol_type = protein
                        organism = Mus musculus
SEQUENCE: 16
DVVMTQTPLS LPVSLGDQAS ISCRSRQSLV NSNGNTFLQW YLQKPGQSPK LLIYKVSLRF     60
SGVPDRFSGS GSGTDFTLKI SRVEAEDLGL YFCSQSTHVP PTFGGGTKLE IK            112

SEQ ID NO: 17           moltype = AA  length = 112
FEATURE                 Location/Qualifiers
source                  1..112
                        mol_type = protein
                        organism = synthetic construct
REGION                  1..112
                        note = Humanized light chain variable region
SEQUENCE: 17
DIVMTQTPLS LPVTLGQPAS ISCRSRQSLV NSNGNTFLQW LQQRPGQPPR LLIYKVSLRF     60
SGVPDRFSGS GAGTDFTLTI SRVEAEDVGI YFCSQSTHVP PTFGQGTKVE IK            112

SEQ ID NO: 18           moltype = AA  length = 112
FEATURE                 Location/Qualifiers
source                  1..112
                        mol_type = protein
                        organism = synthetic construct
REGION                  1..112
                        note = Humanized light chain variable region
SEQUENCE: 18
DIVMTQTPLS LSVTPGQPAS ISCRSRQSLV NSNGNTFLQW YLQKPGQSPQ LLIYKVSLRF     60
SGVPDRFSGS GSGTDFTLKI SRVEPEDVGV YYCSQSTHVP PTFGGGTKVE VK            112

SEQ ID NO: 19           moltype = AA  length = 112
FEATURE                 Location/Qualifiers
source                  1..112
                        mol_type = protein
                        organism = synthetic construct
REGION                  1..112
                        note = Humanized light chain variable region
SEQUENCE: 19
DVVMTQSPLS LPVTLGQPAS ISCRSRQSLV NSNGNTFLQW FQQRPGQSPR RLIYKVSLRF     60
SGVPDRFSGS GSDTDFTLRI SRVEAEDVGL YYCSQSTHVP PTFGQGTKLE IK            112

SEQ ID NO: 20           moltype = AA  length = 112
FEATURE                 Location/Qualifiers
REGION                  1..112
                        note = Humanized light chain variable region
source                  1..112
                        mol_type = protein
                        organism = synthetic construct
SEQUENCE: 20
DIVMTQTPLS LSVTPGQPAS ISCRSRQSLV NSNGNTFLQW LLQKPGQPPQ LLIYKVSLRF     60
SGVPNRFSGS GSGTDFTLKI SRVEAEDVGL YYCSQSTHVP PTFGGGTKVE IK            112
```